(12) United States Patent
Yen et al.

(10) Patent No.: US 8,859,239 B2
(45) Date of Patent: Oct. 14, 2014

(54) METHODS FOR SMALL RNA SEQUENCING

(75) Inventors: Yun Yen, Arcadia, CA (US); Guihua Sun, Arcadia, CA (US)

(73) Assignee: City of Hope, Duarte, CA (US)

( * ) Notice: Subject to any disclaimer, the term of this patent is extended or adjusted under 35 U.S.C. 154(b) by 64 days.

(21) Appl. No.: 13/506,739

(22) Filed: May 11, 2012

(65) Prior Publication Data
US 2013/0012398 A1 Jan. 10, 2013

Related U.S. Application Data

(60) Provisional application No. 61/519,023, filed on May 13, 2011.

(51) Int. Cl.
*C12P 19/34* (2006.01)
*C12Q 1/68* (2006.01)

(52) U.S. Cl.
CPC ............... *C12Q 1/6869* (2013.01); *C12P 19/34* (2013.01); *C12Q 2600/178* (2013.01)
USPC ....................................................... 435/91.2

(58) Field of Classification Search
None
See application file for complete search history.

(56) References Cited

PUBLICATIONS

Bartel, D. P., "MicroRNAs: Target Recognition and Regulatory Functions," Cell 136:215-233 (2009).
Chiang, H. R., et al., "Mammalian MicroRNAs: Experimental Evaluation of Novel and Previously Annotated Genes," Genes Devel. 24:992-1009 (2010).
Cronn, R., et al., "Multiplex Sequencing of Plant Chloroplast Genomes Using Solexa Sequencing-by-Synthesis Technology," Nucleic Acids Research 36(19):e122 (2008) doi:10.1093/nar/gkn502.
Cummins, J. M., et al., "The Colorectal MicroRNAome," PNAS 103(10):3687-3692 (2006).
De Hoon, M.J.L., et al., "Open Source Clustering Software," Bioinformatics 20(9):1453-1454 (2004).
Ender, C., et al., "A Human SnoRNA with MicroRNA-Like Functions," Mol. Cell 32:519-528 (2008).
Galasso, M., et al., "Non-Coding RNAs: A Key to Future Personalized Molecular Therapy?" Genome Med. 2:12 (2010) doi:10.1186/gm133.
Goff, L. A., et al., "Ago2 Immunoprecipitation Identifies Predicted MicroRNAs in Human Embryonic Stem Cells and Neural Precursors," PLoS One 4(9):e7192 (2009) doi:10.1371/journal.pone.0007192.
Griffiths-Jones, S., "miRBase: microRNA Sequences and Annotation," Curr. Protoc. Bioinform. 29:12.9.1-12.9.10 (2010).
Hafner, M., et al., "Identification of MicroRNAs and Other Small Regulatory RNAs Using cDNA Library Sequencing," Methods 44(1):3-12 (2008).
Kim, V. N., "Biogenesis of Small RNAs in Animals," Nat. Rev. Mol. Cell Biol. 10:126-139 (2009).
Lagos-Quintana, M., et al., "Identification of Novel Genes Coding for Small Expressed RNAs," Science 294:853-858 (2001).
Lau, N. C., et al., "An Abundant Class of Tiny RNAs with Probable Regulatory Roles in *Caenorhabditis elegans*," Science 294:862-858 (2001).
Lee, R., et al., "An Extensive Class of Small RNAs in *Caenorhabditis elegans*," Science 294:864-862 (2001).
Lee., R. C., et al., "The *C. elegans*Heterochronic Gene Lin-4 Encodes Small RNAs with Antisense Complementarity to Lin-14," Cell 75:843-854 (1993).
Levin, J. Z., et al., "Comprehensive Comparative Analysis of Strand-Specific RNA Sequencing Methods," Nat. Methods 7(9):709-715 (2010).
Linsen, S. E.V., et al., "Limitations and Possibilities of Small RNA Digital Gene Expression Profiling," Nat. Methods 6 (7):474-476 (2009).
Lu, C., et al., "Construction of Small RNA cDNA Libraries for Deep Sequencing," Methods 43:110-117 (2007).
Lu, C., et al., "Elucidation of the Small RNA Component of the Transcriptome," Science 309:1567-1569 (2005).
Nagpal, J.K., et al., "Targeting miRNAs for Drug Discovery: A New Paradigm," Curr. Mol. Med. 10:503-510 (2010).
Pasquinelli, A. E., et al., "Conservation of the Sequence and Temporal Expression of Let-7 Heterochronic Regulatory RNA," Nature 408:86-89 (2000).
Pederson, T., et al., "Regulatory RNAs Derived from Transfer RNA?" RNA 16:1865-1869 (2010).
Pfeffer, S., et al., "Cloning of Small RNA Molecules," Curr. Protoc. Mol. Biol. 26.4.1-26.4.18 (2005).
Reinhart, B. J., et al., "The 21-Nucleotide Let-7 RNA Regulates Developmental Timing in *Caenorhabditis elegans*," Nature 403:901-906 (2000).
Riedmann, L. T., et al., "miRNA, siRNA, piRNA and Argonautes," RNA Biol. 7(2):133-139 (2010).
Saldanha, A. J., et al., "Java Treeview—Extensible Visulaization of Microarray Data," Bioinformatics 20 (17):3246-3248 (2004).
Sun, G., et al., "SNPs in Human miRNA Genes Affect Biogenesis and Function," RNA 15:1640-1651 (2009).
Taft, R. J., et al., "Small RNAs Derived from snoRNAs," RNA 15:1233-1240 (2009).
Tang, F., et al., "RNA-Seq Analysis to Capture the Transcriptome Landscape of a Single Cell," Nat. Protoc. 5 (3):516-535 (2010).
Thomson, T., et al., "The Biogenesis and Function PIWI Proteins and piRNAs: Progress and Prospect," Annu. Rev. Cell Dev. Biol. 25:355-376 (2009).

(Continued)

*Primary Examiner* — James Martinell
(74) *Attorney, Agent, or Firm* — Perkins Coie LLP; Patrick D. Morris

(57) ABSTRACT

Next generation sequencing technologies are becoming a preferred method for sequencing nucleic acids and profiling miRNAs. Experimental results disclosed herein show that the most common platform for preparing nucleic acids such as miRNAs for sequencing introduces serious biases. Provided herein are compositions and methods for improved sequencing and miRNA profiling using a set of customized ligation adaptors.

7 Claims, 14 Drawing Sheets

(56) References Cited

PUBLICATIONS

Tian, G. et al. "Sequencing Bias: Comparison of Different Protocols of MicroRNA Library Construction," BMC Biotech. 10:64 (2010).

Wang, W.C., et al., "miRExpress: Analyzing High-Throughput Sequencing Data for Profiling microRNA Expression," BMC Bioinformatics 10:328 (2009) doi:10.1186/1471-2105-10-328.

Wightman, B., et al., "Posttranscriptional Regulation of the Heterochronic Gene Lin-14 by Lin-4 Mediates Temporal Pattern Formation in *C. elegans*," Cell 75:855-862 (1993).

Witten, D., et al., "Ultra-High Throughput Sequencing-Based Small RNA Discovery and Discrete Statistical Biomarker Analysis in a Collection of Cervical Tumours and Matched Controls," BMC Biol. 8:58 (2010).

Wu, H., et al., "miRNA Profiling of Naïve, Effector and Memory CD8 T Cells," PLoS One 2(10):e1020 (2007) doi:10.1371/journal.pone.0001020.

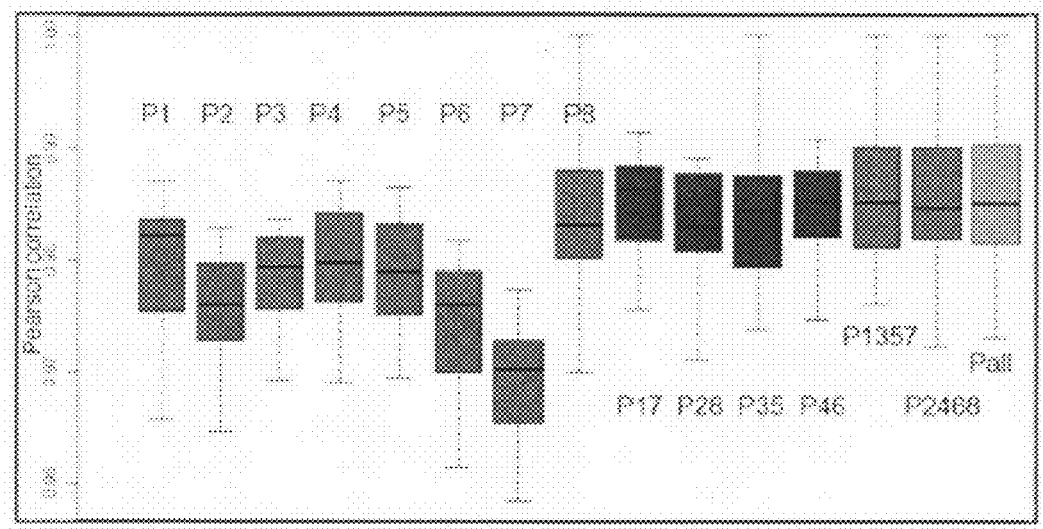

SEQUENCE LISTING

```
<160> NUMBER OF SEQ ID NOS: 70

<210> SEQ ID NO 1
<211> LENGTH: 23
<212> TYPE: RNA
<213> ORGANISM: Artificial Sequence
<220> FEATURE:
<223> OTHER INFORMATION: 5' adaptor for smRNA sequencing

<400> SEQUENCE: 1
guucagaguu cuacaguccg auc                                          23

<210> SEQ ID NO 2
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 2
guucagaguu cuacaguccg aucaaa                                       26

<210> SEQ ID NO 3
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 3
guucagaguu cuacaguccg aucuau                                       26

<210> SEQ ID NO 4
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 4
```

-continued guucagaguu cuacaguccg aucauc                                              26

<210> SEQ ID NO 5
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 5
guucagaguu cuacaguccg aucuug                                              26

<210> SEQ ID NO 6
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 6
guucagaguu cuacaguccg aucgca                                              26

<210> SEQ ID NO 7
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 7
guucagaguu cuacaguccg aucccu                                              26

<210> SEQ ID NO 8
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 8
guucagaguu cuacaguccg auccgc                                              26

<210> SEQ ID NO 9
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 9
guucagaguu cuacaguccg aucggg                                              26

<210> SEQ ID NO 10
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 10
guucagaguu cuacaguccg aucaau                                              26

<210> SEQ ID NO 11
<211> LENGTH: 26
<212> TYPE: RNA

```
<213> ORGANISM: Artificial Sequence
<220> FEATURE:
<223> OTHER INFORMATION: 5' adaptor for smRNA sequencing

<400> SEQUENCE: 11
guucagaguu cuacaguccg aucuac                                              26

<210> SEQ ID NO 12
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 12
guucagaguu cuacaguccg aucaug                                              26

<210> SEQ ID NO 13
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 13
guucagaguu cuacaguccg aucuua                                              26

<210> SEQ ID NO 14
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 14
guucagaguu cuacaguccg aucgcu                                              26

<210> SEQ ID NO 15
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 15
guucagaguu cuacaguccg aucccc                                              26

<210> SEQ ID NO 16
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 16
guucagaguu cuacaguccg auccgg                                              26

<210> SEQ ID NO 17
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 17
guucagaguu cuacaguccg aucgga                                              26
```

```
<210> SEQ ID NO 18
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 18
guucagaguu cuacaguccg aucaac                                          26

<210> SEQ ID NO 19
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 19
guucagaguu cuacaguccg aucuag                                          26

<210> SEQ ID NO 20
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 20
guucagaguu cuacaguccg aucaua                                          26

<210> SEQ ID NO 21
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 21
guucagaguu cuacaguccg aucuuu                                          26

<210> SEQ ID NO 22
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 22
guucagaguu cuacaguccg aucgcc                                          26

<210> SEQ ID NO 23
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 23
guucagaguu cuacaguccg aucccg                                          26

<210> SEQ ID NO 24
<211> LENGTH: 26
<212> TYPE: RNA
<213> ORGANISM: Artificial Sequence
<220> FEATURE:
```

-continued

<223> OTHER INFORMATION: 5' adaptor for smRNA sequencing

<400> SEQUENCE: 24
guucagaguu cuacaguccg auccga                                          26

<210> SEQ ID NO 25
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 25
guucagaguu cuacaguccg aucggu                                          26

<210> SEQ ID NO 26
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 26
guucagaguu cuacaguccg aucaag                                          26

<210> SEQ ID NO 27
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 27
guucagaguu cuacaguccg aucuaa                                          26

<210> SEQ ID NO 28
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 28
guucagaguu cuacaguccg aucauu                                          26

<210> SEQ ID NO 29
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 29
guucagaguu cuacaguccg aucuuc                                          26

<210> SEQ ID NO 30
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 30
guucagaguu cuacaguccg aucgcg                                          26

```
<210> SEQ ID NO 31
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 31
guucagaguu cuacaguccg auccca                                        26

<210> SEQ ID NO 32
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 32
guucagaguu cuacaguccg auccgu                                        26

<210> SEQ ID NO 33
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 33
guucagaguu cuacaguccg aucggc                                        26

<210> SEQ ID NO 34
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 34
guucagaguu cuacaguccg aucgaa                                        26

<210> SEQ ID NO 35
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 35
guucagaguu cuacaguccg aucagu                                        26

<210> SEQ ID NO 36
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 36
guucagaguu cuacaguccg aucacc                                        26

<210> SEQ ID NO 37
<211> LENGTH: 26
<212> TYPE: RNA
<213> ORGANISM: Artificial Sequence
<220> FEATURE:
<223> OTHER INFORMATION: 5' adaptor for smRNA sequencing
```

```
<400> SEQUENCE: 37
guucagaguu cuacaguccg aucucg                                      26

<210> SEQ ID NO 38
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 38
guucagaguu cuacaguccg aucgua                                      26

<210> SEQ ID NO 39
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 39
guucagaguu cuacaguccg auccuu                                      26

<210> SEQ ID NO 40
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 40
guucagaguu cuacaguccg auccac                                      26

<210> SEQ ID NO 41
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 41
guucagaguu cuacaguccg aucugg                                      26

<210> SEQ ID NO 42
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 42
guucagaguu cuacaguccg aucgau                                      26

<210> SEQ ID NO 43
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 43
guucagaguu cuacaguccg aucagc                                      26

<210> SEQ ID NO 44
<211> LENGTH: 26
```

```
<212> TYPE: RNA
<213> ORGANISM: Artificial Sequence
<220> FEATURE:
<223> OTHER INFORMATION: 5' adaptor for smRNA sequencing

<400> SEQUENCE: 44
guucagaguu cuacaguccg aucacg                                              26

<210> SEQ ID NO 45
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 45
guucagaguu cuacaguccg aucuca                                              26

<210> SEQ ID NO 46
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 46
guucagaguu cuacaguccg aucguu                                              26

<210> SEQ ID NO 47
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 47
guucagaguu cuacaguccg auccuc                                              26

<210> SEQ ID NO 48
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 48
guucagaguu cuacaguccg auccag                                              26

<210> SEQ ID NO 49
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 49
guucagaguu cuacaguccg aucuga                                              26

<210> SEQ ID NO 50
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 50
```
guucagaguu cuacaguccg aucgac            26

<210> SEQ ID NO 51
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 51
guucagaguu cuacaguccg aucagg            26

<210> SEQ ID NO 52
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 52
guucagaguu cuacaguccg aucaca            26

<210> SEQ ID NO 53
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 53
guucagaguu cuacaguccg aucucu            26

<210> SEQ ID NO 54
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 54
guucagaguu cuacaguccg aucguc            26

<210> SEQ ID NO 55
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 55
guucagaguu cuacaguccg auccug            26

<210> SEQ ID NO 56
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 56
guucagaguu cuacaguccg auccaa            26

<210> SEQ ID NO 57
<211> LENGTH: 26
<212> TYPE: RNA
<213> ORGANISM: Artificial Sequence

```
<220> FEATURE:
<223> OTHER INFORMATION: 5' adaptor for smRNA sequencing

<400> SEQUENCE: 57
guucagaguu cuacaguccg aucugu                                          26

<210> SEQ ID NO 58
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 58
guucagaguu cuacaguccg aucgag                                          26

<210> SEQ ID NO 59
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 59
guucagaguu cuacaguccg aucaga                                          26

<210> SEQ ID NO 60
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 60
guucagaguu cuacaguccg aucacu                                          26

<210> SEQ ID NO 61
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 61
guucagaguu cuacaguccg aucucc                                          26

<210> SEQ ID NO 62
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 62
guucagaguu cuacaguccg aucgug                                          26

<210> SEQ ID NO 63
<211> LENGTH: 26
<212> TYPE: RNA
```

```
<213> ORGANISM: Artificial Sequence
<220> FEATURE:
<223> OTHER INFORMATION: 5' adaptor for smRNA sequencing

<400> SEQUENCE: 63
guucagaguu cuacaguccg auccua                                          26

<210> SEQ ID NO 64
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 64
guucagaguu cuacaguccg auccau                                          26

<210> SEQ ID NO 65
<211> LENGTH: 26
<212> TYPE: RNA
<213> ORGANISM: Artificial Sequence
<220> FEATURE:
<223> OTHER INFORMATION: 5' adaptor for smRNA sequencing

<400> SEQUENCE: 65
guucagaguu cuacaguccg aucugc                                          26

<210> SEQ ID NO 66
<211> LENGTH: 24
<212> TYPE: RNA
<213> ORGANISM: Artificial Sequence
<220> FEATURE:
<223> OTHER INFORMATION: 3' adaptor for smRNA sequencing

<400> SEQUENCE: 66
aucucguaug ccgucuucug cuug                                            24

<210> SEQ ID NO 67
<211> LENGTH: 21
<212> TYPE: DNA
<213> ORGANISM: Artificial Sequence
<220> FEATURE:
<223> OTHER INFORMATION: Reverse transcription primer

<400> SEQUENCE: 67
caagcagaag acggcatacg a                                               21

<210> SEQ ID NO 68
<211> LENGTH: 44
<212> TYPE: DNA
<213> ORGANISM: Artificial Sequence
<220> FEATURE:
<223> OTHER INFORMATION: Reverse transcription primer

<400> SEQUENCE: 68
aatgatacgg cgaccaccga caggttcaga gttctacagt ccga                      44

<210> SEQ ID NO 69
<211> LENGTH: 20
<212> TYPE: DNA
<213> ORGANISM: Artificial Sequence
<220> FEATURE:
<223> OTHER INFORMATION: Forward PCR primer

<400> SEQUENCE: 69
caagcagaag acggcatacg                                                 20
```

```
<210> SEQ ID NO 70
<211> LENGTH: 20
<212> TYPE: DNA
<213> ORGANISM: Artificial Sequence
<220> FEATURE:
<223> OTHER INFORMATION: Reverse PCR primer

<400> SEQUENCE: 70
aatgatacgg cgaccaccga                                             20
```

METHODS FOR SMALL RNA SEQUENCING

RELATED APPLICATIONS

The present application claims priority to U.S. Provisional Application No. 61/519,023, filed May 13, 2011, the disclosure of which is incorporated by reference herein in its entirety, including drawings.

TABLE SUBMITTED ON COMPACT DISK

Table 2 is contained on a CD-R provided herewith under the file name "54435.8095.US02 Table 2.txt." This file is 194 kb and was created on May 11, 2012. The machine format is IBM-PC and the operating system compatibility is MS-Windows. Two copies of the CD-R containing Table 2 are provided pursuant to 37 C.F.R. §1.52(e)(iii). The complete contents of the CD-R are hereby incorporated by reference herein. Any reference to Table 2 in the specification represents an incorporation by reference of the contents of the file 54435.8095.US02 Table 2.txt at that particular location in the specification.

LENGTHY TABLES

The patent contains a lengthy table section. A copy of the table is available in electronic form from the USPTO web site (http://seqdata.uspto.gov/?pageRequest=docDetail&DocID=US08859239B2). An electronic copy of the table will also be available from the USPTO upon request and payment of the fee set forth in 37 CFR 1.19(b)(3).

SEQUENCE LISTING SUBMITTED ON COMPACT DISK

The sequence listing in computer readable format is contained on a CD-R provided herewith under the file name "Sequence Listing.txt." This file is 15 kb and was created on May 11, 2012. The machine format is IBM-PC and the operating system compatibility is MS-Windows. Two copies of the CD-R containing the sequence listing in computer readable format are provided pursuant to 37 C.F.R. §1.824. The complete contents of the CD-R are hereby incorporated by reference herein. A paper copy of the sequence listing is also provided.

BACKGROUND

Small RNAs (smRNAs) encompass several different classes of non-coding RNAs, including microRNAs (miRNAs), short interfering RNAs (siRNAs), small nucleolar RNAs (snoRNAs), and small nuclear RNAs (snRNAs). Among the endogenous smRNAs, miRNA is the most well studied with regard to both biogenesis and functional mechanism. miRNAs are short RNA molecules that act as post-transcriptional regulators by binding to mRNA and preventing it from being translated. The first miRNA, Lin-4, was identified in *C. elegans* in 1993 (Lee 1993; Wightman 1993). In 2000, a second miRNA, Let-7, was identified and found to be conserved across many species (Pasquinelli 2000; Reinhart 2000). In 2001, it was disclosed that miRNAs probably exist in all species (Lee 2001; Lau 2001; Lagos-Quintana 2001). Since 2001, miRNA research has extended to almost all corners of biological science, with in-depth investigations into miRNA biogenesis and biological functions and the use of miRNA as a therapeutic tool, diagnosis and prognosis marker, and treatment response predictor marker (Galasso 2010; Nagpal 2010; Kim 2009; Bartel 2009). This progression in miRNA study has coincided with the identification and profiling of novel smRNAs in many organisms.

smRNA profiling have traditionally relied on cloning and sequencing of individual RNAs using standard molecular methods. In the most common approach, adaptor oligonucleotides are joined to the 3' and 5' termini of smRNAs, and the ligation products are reverse transcribed and PCR amplified to generate a cDNA library. This procedure represents a significant technical challenge because it requires three gel purification steps. In addition, thousands of clones have to be individually sequenced to identify the smRNA population. This standard protocol is labor intensive, painstaking, and requires large amounts of starting materials, and therefore is not practical for many research or clinical settings (Pfeffer 2005). Although cost can be reduced several fold by concatenating fragments of smRNAs with both adaptors to sequence several clones together, expense is still a major obstacle in thoroughly surveying smRNA populations.

Next generation sequencing (NGS) technology was first applied to smRNA discovery with the use of massive parallel signature sequencing to survey the smRNA library of *Arabidopsis thaliana* (Lu 2005). Since then, many modified smRNA profiling procedures based on NGS have been developed and tested on various platforms (Hafner 2008; Lu 2007; Tang 2010). To date, human miRNAs alone represent 1,048 unique sequence entries in miRBase 16 (Griffiths-Jones 2010). NGS technology has also helped in the discovery of other smRNAs (Lu 2005).

Illumina's NGS technology (Solexa) has been rated one of the two leading protocols for RNA sequencing (Levin 2010). The Solexa platform has gained some advantage over other smRNA profiling protocols with their smRNA cloning protocol v1.5. This protocol, which is summarized in FIG. 1, drastically reduces the difficulties of smRNA cDNA library construction by eliminating the need for gel purification of smRNA/smRNA-adaptors (the most challenging and critical steps in smRNA discovery) and by requiring only about 1 μg of total RNA. However, it has been found that this protocol presents a major artifact in smRNA sequencing experiments. Therefore, there is a need in the art for improved methods of smRNA sequencing.

SUMMARY

Provided herein in certain embodiments are isolated polynucleotides comprising, consisting of, or consisting essentially of a nucleotide sequence selected from the group consisting of SEQ ID NOs:2 to 65.

Provided herein in certain embodiments are compositions comprising one or more isolated polynucleotides each independently comprising, consisting of, or consisting essentially of a nucleotide sequence selected from the group consisting of SEQ ID NOs:2 to 65. In certain of these embodiments, the composition comprises a specific set of two or more isolated polynucleotides each independently comprising, consisting of, or consisting essentially of a nucleotide sequence selected from the group consisting of SEQ ID NOs:2 to 65, and in certain of these embodiments the set is selected from a) a set of polynucleotides representing each of SEQ ID NOs:2-9, b) a set of polynucleotides representing each of SEQ ID NOs: 10-17, c) a set of polynucleotides representing each of SEQ ID NOs:18-25, d) a set of polynucleotides representing each of SEQ ID NOs:26-33, e) a set of polynucleotides representing each of SEQ ID NOs:34-41, f) a set of polynucleotides representing each of SEQ ID NOs:42-49, g) a set of polynucleotides representing each of SEQ ID NOs:50-57, h) a set of polynucleotides representing each of SEQ ID NOs:58-65, i) a set of polynucleotides representing each of SEQ ID NOs: 2-9 and 50-57, j) a set of polynucleotides representing each of SEQ ID NOs:10-17 and 58-65, k) a set of polynucleotides representing each of SEQ ID NOs:18-25 and 34-41, l) a set of polynucleotides representing each of SEQ ID NOs:26-33 and 42-49, m) a set of polynucleotides representing each of SEQ ID NOs:2-9, 18-25, 34-41, and 50-57, n) a set of polynucleotides representing each of SEQ ID NOs:10-17, 26-33, 42-49, 58-65; and o) a set of polynucleotides representing each of SEQ ID NOs:2-65.

Provided herein in certain embodiments are methods of preparing a target nucleic acid for sequencing comprising the steps of: a) ligating a 3' adaptor to the target nucleic acid, wherein the 3' adaptor consists of the nucleotide sequence of SEQ ID NO:66 or is an extended 3' adaptor comprising the nucleotide sequence of SEQ ID NO:66 with one or more nucleotides added to the 5' end; b) ligating a 5' adaptor to the 3' adaptor-target nucleic acid complex of step (a), wherein the 5' adaptor consists of the nucleotide sequence of SEQ ID NO:1 or is an extended 5' adaptor comprising the nucleotide sequence of SEQ ID NO:1 with one or more nucleotides added to the 3' end; c) reverse transcribing the 3' adaptor-target nucleic acid-5' adaptor ligation product of step (b); d) PCR amplifying the reverse transcribed ligation product of step (c); and e) gel purifying the amplified target nucleic acid; provided that at least one of steps (a) and (b) must utilize an extended 3' or 5' adaptor, respectively. In certain of these embodiments, the target nucleic acid is a DNA or RNA molecule, and in certain of these embodiments the target nucleic acid is a smRNA. In certain embodiments, the methods further comprise a step of sequencing the gel purified target nucleic acid of step (e). In certain embodiments, the extended 5' adaptor comprises a nucleotide sequence selected from the group consisting of SEQ ID NOs:2 to 65. In certain embodiments, more than one 3' adaptor and/or more than one 5' adaptor is used for steps (a) and (b), respectively. In certain of these embodiments, step (b) utilizes a pool of 5' adaptors each independently comprising, consisting of, or consisting essentially of the nucleotide sequences of SEQ ID NOs:2 to 65.

BRIEF DESCRIPTION OF THE DRAWINGS

FIG. 8: Pearson correlation among adaptor pools in Test 2. Variation between adaptor pools was greatly reduced in the 16×4 pools (P17, P28, P35, and P46) versus the 8×8 pools (P1 to P8).

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Illumina's v1.5 smRNA preparation protocol ("Illumina protocol") utilizes five main steps: 1) ligation of the 3' adaptor to smRNA, 2) ligation of the 5' adaptor to smRNA, 3) reverse transcription of smRNA with both adaptors to cDNA, 4) PCR amplification of the cDNA, and 5) smRNA gel purification. The default 3' adaptor, which is modified to target smRNAs with a 3' hydroxyl group, corresponds to the surface-bound amplification primer and is required for reverse transcription. The default 5' adaptor, which has the nucleotide sequence set forth in SEQ ID NO:1, is required for amplification of smRNA fragments.

smRNA libraries prepared by the Illumina protocol are loaded onto single-read flowcells for cluster generation. During this process, the smRNA samples are bound to complementary adaptor oligonucleotides grafted onto the surface of an Illumina Genome Analyzer flow cell. These complementary adaptor oligonucleotides bind to either the 5' or 3' adaptors. Unlabeled nucleotides are added to initiate a solid-phase bridge amplification, which results in the formation of double-stranded bridges. The double-stranded molecules are denatured to generate single-stranded templates anchored to the substrate, followed by amplification to generate dense clusters of double-stranded DNA. Sequencing by synthesis (SBS) is then performed to ascertain the sequences of the smRNAs.

One drawback of the Illumina protocol is that the bridge amplification step requires both the 5' and 3' adaptors to be complementary to the complementary adaptor oligonucleotides on the flowcell surface. This creates a problem using bases within the sequences of either adaptor for barcoding.

Due to heterogeneity of the 3'ends of smRNAs, the fact that SBS is more likely to generate errors close to the end of the short reads (Wu 2007; Tian 2010), and the fact that the Illumina protocol specifically requires the pre-adenylated 5' end of the 3' adaptor (which is expensive to make), the 3' end of the 5' adaptor is the choice for multiplexing in the same flowcell for sequencing smRNAs of about 17 to 32 nts in length, such as piRNA, tRNA halves, and snoRNA derived smRNAs (Riedmann 2010; Thomson 2009; Pederson 2010; Ender 2008; Taft 2009).

Figure 1:
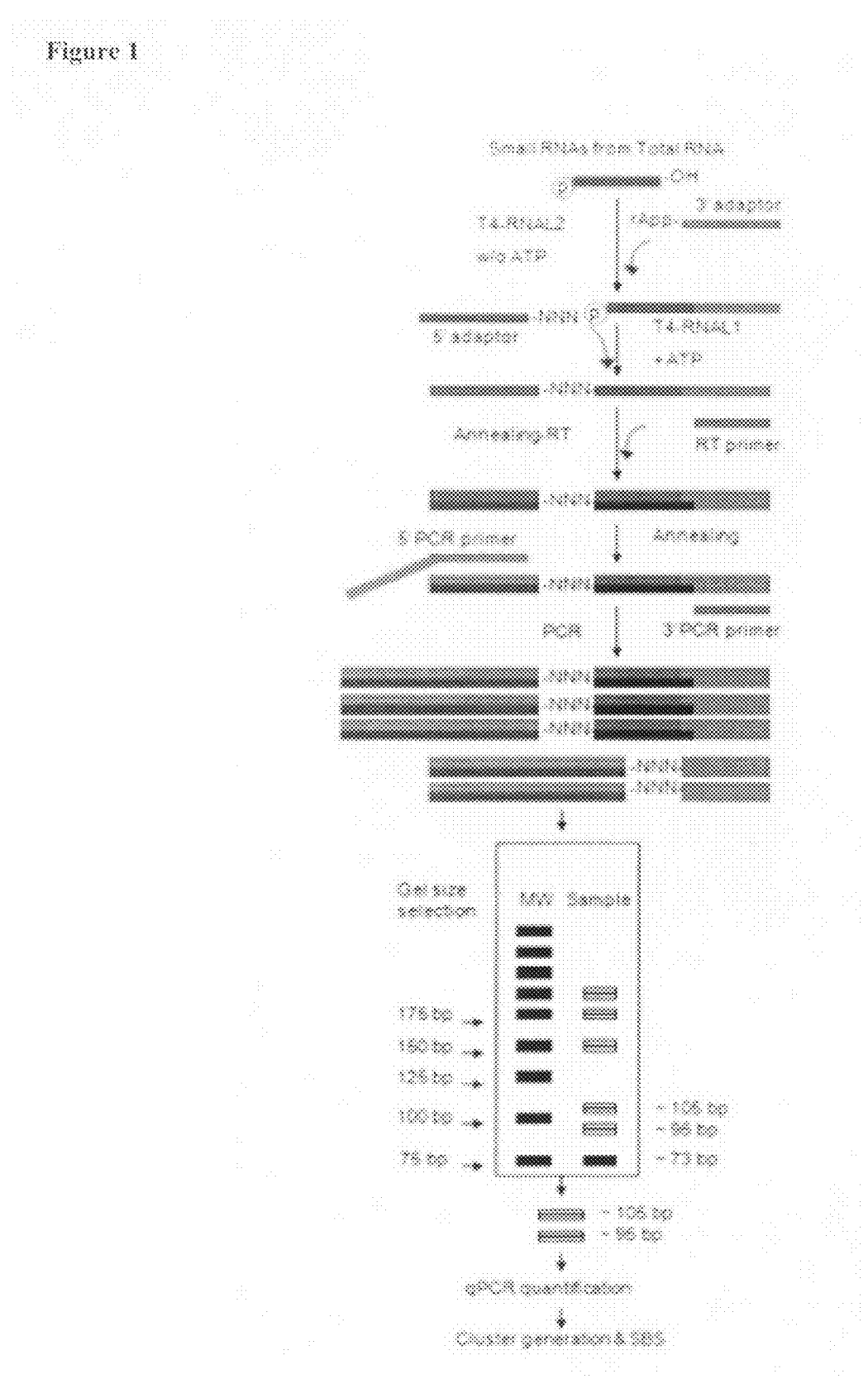
FIG. 1: Diagram of Illumina v1.5 smRNA preparation and sequencing protocol.
Figure 2:
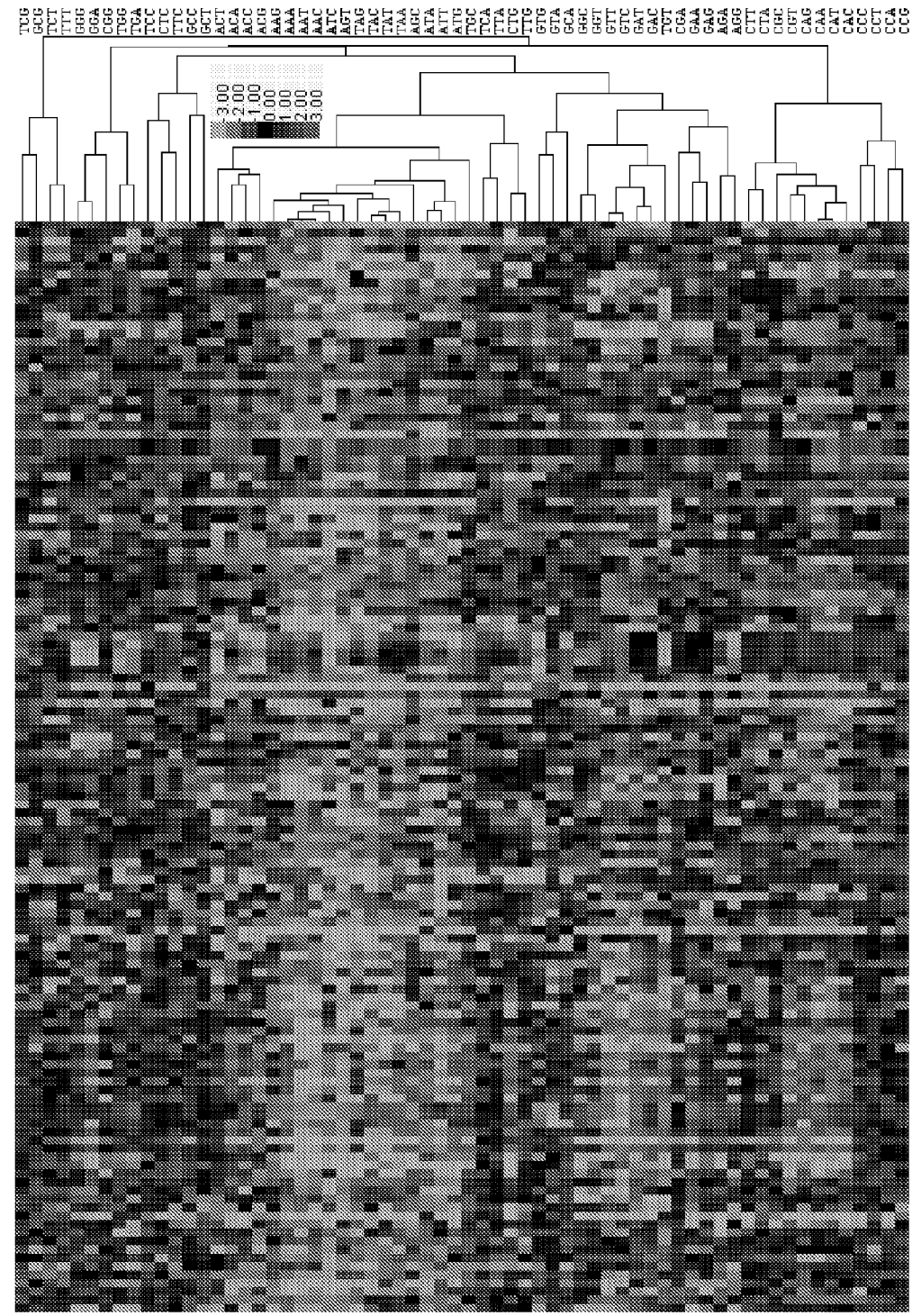
FIG. 2: Heatmap of clustered normalized reads of miRNA population for 64 customized 5' adaptors. Total reads of each adaptor were normalized to a constant and each miRNA was scaled up according to the ratio of constant to the total reads. Normalized reads were Log2 transformed and the value was used to cluster miRNAs as complete linkage and generate the heatmap.
Figure 11:
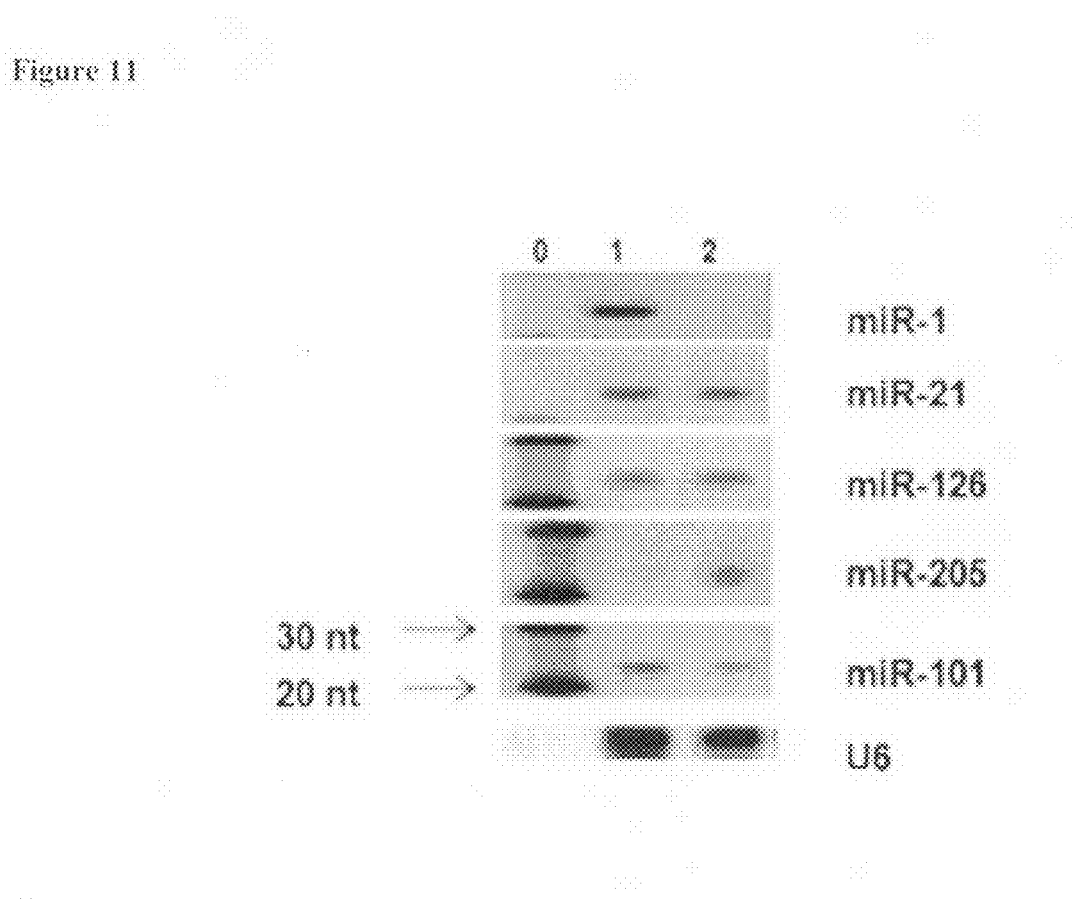
FIG. 11: Northern blot analysis of miR-21, -1, -126, -205, and -101 in human RNA pool and human breast RNA. U6 snRNA was used as RNA loading control. Lane 0: RNA decade marker; Lane 1: human RNA pool; Lane 2: breast RNA.

As disclosed herein, the Illumina protocol was modified by adding three nucleotides (nt) at the 3' end of the default 5' adaptor for multiplexing. 64 different three nt sequences were utilized, representing all possible three nt combinations. The resultant customized 5' adaptors were compared to the default Illumina 5' adaptor for their efficacy in identifying miRNAs from various tissue samples using the Illumina protocol. Significant read biases were observed for each of the adaptor sequences. This kind of bias in smRNA digital gene expression profiling has been reported previously (Linsen 2009). To overcome these biases, the customized 5' adaptors were combined into eight pools of eight adaptors each, four pools of 16 adaptors each, two pools of 32 adaptors each, and one pool of 64 adaptors. Pooling was based on the cluster data for the 64 customized 5' adaptors. The last three nts of the customized 5' adaptors were all found to influence the sequencing results (FIG. 2). Analysis of the pool data showed that pools containing 16, 32, or 64 customized 5' adaptors minimized results bias, and were sufficient to identify all highly expressed miRNAs in various tissue samples (FIGS. 4, 5, and 12-14). Most importantly, subsequent comparison of miRNA sequencing of the same miRNA sample showed that the pooled customized 5' adaptors dramatically reduced result bias as compared to the default 5' adaptor. Use of all pools (8, 16, 32, and 64) resulted in a significant improvement in miRNA population coverage versus the use of the default adaptor alone, and resulted in identification of 893 of the 1,100 human mature miRNA/miRNA* sequences (about 81%) documented in miRBase 15. To further verify the superiority of the pooled adaptors to the default Illumina 5' adaptor, the eight adaptor pools and the default Illumina 5' adaptor were used to sequence miRNA from human breast tissue. The eight adaptor pools produced results that were more consistent with Northern blotting results than those obtained using the default adaptor (FIG. 11).

In summary, the results disclosed herein reveal a significant pitfall in the use of the default 5' adaptor in the Illumina protocol. Sequence results obtained using this adaptor are biased by the short nucleotide fragments being sequenced, and therefore may not reflect the true biological composition of a sequence sample. Coverage and abundance are crucial to the evaluation of miRNA biological function and to the utilization of miRNAs as biomarkers in a clinical setting.

The compositions and methods disclosed herein can be used to overcome various shortcomings associated with Illumina and other next generation sequencing technologies that utilize adaptor sequences ligated to a sequence of interest, and to provide improved sequencing results for target nucleic acids. These target nucleic acids may be DNA or RNA molecules, including for example smRNA molecules. In certain embodiments, the target nucleic acids may be part of a target nucleic acid sample containing two or more target nucleic acids. In these embodiments, the target nucleic acid sample may comprise two or more copies of a single target nucleic acid, or it may comprise one or more copies of two or more different target nucleic acids. For example, a target nucleic acid sample may comprise one or more RNA molecules, DNA molecules, or a mixture thereof (such as a genomic nucleic acid sample).

Provided herein in certain embodiments are isolated polynucleotides for use in identifying, tagging, and sequencing a target nucleic acid. The target nucleic acid may be a DNA molecule or an RNA molecule, and in certain embodiments the target nucleic acid may be a smRNA molecule. In certain embodiments, the isolated polynucleotides consist of or consist essentially of the nucleotide sequence of the default Illumina 5' adaptor (SEQ ID NO:1) with one or more nucleotides added to the 3' end. In certain of these embodiments, the isolated polynucleotides consist of or consist essentially of the nucleotide sequence of SEQ ID NO:1 plus one, two, three, four, five, six, seven, eight, or more than eight nucleotides added to the 3' end. In certain of these embodiments, the isolated polynucleotides comprise, consist of, or consist essentially of a nucleotide sequence as set forth in any of SEQ ID NOs:2-65.

Provided herein in certain embodiments are isolated polynucleotides for use in identifying, tagging, and sequencing a target nucleic acid. The target nucleic acid may be a DNA molecule or an RNA molecule, and in certain embodiments the target nucleic acid may be a smRNA molecule. In certain embodiments, the isolated polynucleotides consist of or consist essentially of the nucleotide sequence of the default Illumina 3' adaptor (SEQ ID NO:66) with one or more nucleotides added to the 5' end. In certain of these embodiments, the isolated polynucleotides consist of or consist essentially of the nucleotide sequence of SEQ ID NO:66 plus one, two, three, four, five, or more than five nucleotides added to the 5' end.

Provided herein in certain embodiments are compositions comprising one or more of the isolated polynucleotides provided herein. In certain embodiments, these compositions comprise four or more, eight or more, 16 or more, 24 or more, 32 or more, 40 or more, 48 or more, 56 or more, or 64 or more of the isolated polynucleotides provided herein. In certain embodiments, the compositions comprise isolated polynucleotides comprising, consisting of, or consisting essentially of each of the nucleotide sequences of 1) SEQ ID NOs:2-9; 2) SEQ ID NOs:10-17; 3) SEQ ID NOs:18-25; 4) SEQ ID NOs:26-33; 5) SEQ ID NOs:34-41; 6) SEQ ID NOs:42-49; 7) SEQ ID NOs:50-57; 8) SEQ ID NOs:58-65; 9) SEQ ID NOs:2-9 and 50-57; 10) SEQ ID NOs:10-17 and 58-65; 11) SEQ ID NOs:18-25 and 34-41; 12) SEQ ID NOs:26-33 and 42-49; 13) SEQ ID NOs:2-9, 18-25, 34-41, and 50-57; 14) SEQ ID NOs:10-17, 26-33, 42-49, 58-65; and 15) SEQ ID NOs:2-65. In certain embodiments, these kits further comprise instructions for use.

Provided herein in certain embodiments is the use of one or more of the isolated polynucleotides or compositions provided herein for the identification, tagging, sequencing, and/or preparation for sequencing of one or more target nucleic acids. The target nucleic acids may be DNA molecules or RNA molecules, and in certain embodiments the target nucleic acids may be smRNA molecules.

Provided herein in certain embodiments are kits comprising one or more of the polynucleotides provided herein. In certain embodiments, these kits comprise four or more, eight or more, 16 or more, 24 or more, 32 or more, 40 or more, 48 or more, 56 or more, or all 64 of the isolated polynucleotides provided herein. In certain embodiments, the kits comprise isolated polynucleotides comprising, consisting of, or consisting essentially of each of the nucleotide sequences of 1) SEQ ID NOs:2-9; 2) SEQ ID NOs:10-17; 3) SEQ ID NOs: 18-25; 4) SEQ ID NOs:26-33; 5) SEQ ID NOs:34-41; 6) SEQ ID NOs:42-49; 7) SEQ ID NOs:50-57; 8) SEQ ID NOs:58-65; 9) SEQ ID NOs:2-9 and 50-57; 10) SEQ ID NOs:10-17 and 58-65; 11) SEQ ID NOs:18-25 and 34-41; 12) SEQ ID NOs:26-33 and 42-49; 13) SEQ ID NOs:2-9, 18-25, 34-41, and 50-57; 14) SEQ ID NOs:10-17, 26-33, 42-49, 58-65; and 15) SEQ ID NOs:2-65. In certain embodiments, these kits further comprise instructions for use.

Provided herein in certain embodiments are methods for improving the Illumina protocol by using one or more of the isolated polynucleotides provided herein in place of the default Illumina 5' adaptor of SEQ ID NO:1 and/or the default Illumina 3' adaptor of SEQ ID NO:66. In certain embodiments, more than one of the isolated polynucleotides provided herein are utilized such that a pool of 5' or 3' adaptors is present in the RNA adaptor ligation mixture. In certain of these embodiments, the 5' and/or 3' adaptor pool comprises eight or more, 16 or more, 24 or more, 32 or more, 40 or more, 48 or more, 56 or more, or 64 or more of the isolated polynucleotides provided herein. In certain of these embodiments, the 5' adaptor pool comprises a combination of isolated polynucleotides comprises, consisting of, or consisting essentially of each of the nucleotide sequences of 1) SEQ ID NOs:2-9; 2) SEQ ID NOs:10-17; 3) SEQ ID NOs:18-25; 4) SEQ ID NOs:26-33; 5) SEQ ID NOs:34-41; 6) SEQ ID NOs: 42-49; 7) SEQ ID NOs:50-57; 8) SEQ ID NOs:58-65; 9) SEQ ID NOs:2-9 and 50-57; 10) SEQ ID NOs:10-17 and 58-65; 11) SEQ ID NOs:18-25 and 34-41; 12) SEQ ID NOs:26-33 and 42-49; 13) SEQ ID NOs:2-9, 18-25, 34-41, and 50-57; 14) SEQ ID NOs:10-17, 26-33, 42-49, 58-65; and 15) SEQ ID NOs:2-65.

Provided herein in certain embodiments are methods for preparing a target nucleic acid for sequencing comprising the steps of 1) ligating a 3' adaptor to the target nucleic acid; 2) ligating a 5' adaptor to the 3' adaptor-target nucleic acid complex; 3) reverse transcribing the 3' adaptor-target nucleic acid-5' adaptor ligation product, 4) PCR amplifying the reverse transcribed ligation product to amplify target nucleic acids bound to adaptor molecules on both ends; and 5) gel purifying the amplified target nucleic acid, wherein one or both of the 3' and 5' adaptors are isolated polynucleotides as provided herein. In certain embodiments, the target nucleic acid is a smRNA molecule. In these embodiments, the methods comprise the steps of 1) ligating a 3' adaptor to the smRNA; 2) ligating a 5' adaptor to the 3' adaptor-smRNA complex; 3) reverse transcribing the 3' adaptor-smRNA-5' adaptor ligation product, 4) PCR amplifying the reverse transcribed ligation product to amplify smRNAs bound to adaptor molecules on both ends; and 5) gel purifying the amplified smRNA, wherein one or both of the 3' and 5' adaptors are isolated polynucleotides as provided herein. As one example, in certain embodiments the 5' adaptor comprises the nucleotide sequence of SEQ ID NO:1 with one or more nucleotides added to the 3' end, and/or the 3' adaptor comprises the nucleotide sequence of SEQ ID NO:66 with one or more nucleotides added to the 5' end. In certain embodiments, a pool of more than one 5' or 3' adaptor is utilized for the ligation step. For example, the ligation step may utilize a pool of adaptors comprising eight or more, 16 or more, 24 or more, 32 or more, 40 or more, 48 or more, 56 or more, or 64 or more of the isolated polynucleotides provided herein. In certain embodiments, the methods of target nucleic acid preparation disclosed herein further comprise the step of actually sequencing the target nucleic acid, for example using Illumina NGS technology.

In certain embodiments of the target nucleic acid preparation methods provided herein wherein the target nucleic acid is smRNA, the primary method steps are carried out according to the Illumina v1.5 smRNA preparation protocol, with the only difference being the substitution or supplementation of the Illumina default 5' and/or 3' adaptors with one or more of the isolated polynucleotides provided herein.

In certain embodiments of the target nucleic acid preparation methods provided herein wherein the target nucleic acid is smRNA, the 3' ligation adaptor ligation step is carried out as follows. The 3' ligation adaptor(s) is diluted in nuclease free water and mixed with the smRNA sample, and this mixture is incubated at 70° C. for two minutes. The mixture is placed on ice, then mixed with T4 RNL2 truncated reaction buffer (NEB), $MgCl_2$, truncated T4 RNA ligase 2 (NEB), and RNase inhibitor and incubated at 22° C. for one hour. In certain embodiments, one or more oligonucleotides complementary to all or part of the 3' ligation adaptor(s) are included in the ligation reaction mixture. In these embodiments, the oligonucleotides hybridize to the 3' adaptors to prevent hybridization of the adaptors to smRNA. In certain of these embodiments, the oligonucleotide may be tagged to facilitate oligonucleotide removal following completion of the 3' ligation adaptor ligation step. Suitable tags include, for example, magnetic beads or biotin. In certain embodiments, the oligonucleotides may comprise all or a portion of the sequence of the default Illumina PCR primers set forth in SEQ ID NOs:67 and 68.

In certain embodiments of the target nucleic acid preparation methods provided herein wherein the target nucleic acid is smRNA, the 5' ligation adaptor ligation step is carried out as follows. The 5' ligation adaptor(s) is pre-heated to 70° C. for two minutes, transferred to ice, and then added to the 3' ligation mixture of the previous paragraph along with ATP and T4 RNA ligase. This mixture is incubated at 20° C. for one hour. In certain embodiments, one or more oligonucleotides complementary to all or part of the 5' ligation adaptor(s) are included in the ligation reaction mixture. In these embodiments, the oligonucleotides hybridize to the 5' adaptors to prevent hybridization of the adaptors to smRNA. In certain of these embodiments, the oligonucleotide may be tagged to facilitate oligonucleotide removal following completion of the 5' ligation adaptor ligation step. Suitable tags include, for example, magnetic beads or biotin. In certain embodiments, the oligonucleotides may comprise all or a portion of the sequence of the default Illumina PCR primers set forth in SEQ ID NOs:67 and 68.

In certain embodiments of the target nucleic acid preparation methods provided herein wherein the nucleic acid is smRNA, the reverse transcription step is carried out as follows. The ligated smRNA sample is mixed with SRA RT primer (Illumina), centrifuged briefly, heated at 70° C. for two minutes, then placed on ice. First strand buffer (Invitrogen), dNTP mix, DTT, and RNase inhibitor are mixed together, then added to the primer-annealed ligated smRNA sample and heated at 48° C. for three minutes. SuperScript II Reverse Transcriptase (Invitrogen) is added to the mixture, followed by incubation at 44° C. for one hour.

In certain embodiments of the target nucleic acid preparation methods provided herein wherein the target nucleic acid is smRNA, the post-reverse transcription PCR amplification step is carried out as follows. Water, Phusion HF buffer (Illumina), primer GX1 (Illumina), primer GX2 (Illumina), dNTP mix, and Phusion DNA polymerase (Illumina) are mixed together, and the reverse transcribed smRNA sample is added to this mixture. PCR amplification is then performed using one 30 second cycle at 98° C., twelve cycles of 10 second at 98° C., 30 seconds at 60° C., and 15 seconds at 72° C., and a ten minute cycle at 72° C., followed by holding the sample at 4° C. In certain embodiments, the number of cycles may be adjusted up or down based on the amount of smRNA in the initial sample.

In certain embodiments of the target nucleic acid preparation methods provided herein wherein the target nucleic acid is smRNA, the target smRNA may undergo one or more additional steps before, during, or after the primary method steps. For example, the target smRNA may undergo one or more isolation, purification, and/or concentrating steps prior to the 3' adaptor ligation step. Similarly, the target smRNA may undergo one or more amplification steps prior to the 3' adaptor ligation step. In certain embodiments, the integrity of the target smRNA molecule may be evaluated before, during, or after any of the primary method steps.

A target nucleic acid for use in the methods disclosed herein may be obtained from any biological sample containing nucleic acids such as DNA, RNA, smRNA, or combinations thereof. The biological sample may be obtained from any species, including a mammalian species such as a human. In certain embodiments, the target nucleic acid sample is obtained from a bodily fluid such as blood or saliva. In other embodiments, the target nucleic acid sample is obtained from a solid tissue sample, including for example a biopsy sample. In certain embodiments wherein the target nucleic acid is an smRNA molecule, the smRNA molecule may be in a sample comprising more than 1 µg of total RNA, and in certain of these embodiments the smRNA sample comprises more than 2 µg, more than 4 µg, more than 6 µg, more than 8 µg, or more than 10 µg of total RNA. In certain embodiments, the smRNA sample comprises 1-10 µg of total RNA.

Provided herein in certain embodiments are methods of diagnosing a disease using the target nucleic acid preparation and sequencing methods provided herein. In these embodiments, nucleic acid samples from a subject are prepared and sequenced using the methods disclosed herein, then compared to one or more reference sequences representing nucleic acid sequences associated with a particular disease. For example, where the nucleic acid samples contain smRNA, the reference sequences may include bacterial or viral smRNA sequences. In these embodiments, identification of a nucleic acid sequence matching one of the reference sequences indicates the presence of a particular disease, including for example a bacterial or viral infection.

The term "comprising" as used herein, particularly with regard to a component of a composition or a step of a method, encompasses compositions and methods consisting of or consisting essentially of the component or step.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1

Evaluation of Three Nucleotide 5' Adaptor Extensions

It has been reported previously that it is possible to add several nts to the 5' adaptor tail for barcoding for miRNA profiling (Witten 2010; Cronn 2008). To evaluate the effect of three nt extensions, 64 different extension sequences (Table 1) were added to the 3' end of the default Illumina 5' adaptor (SEQ ID NO:1) to produce a series of 64 customized 5' adaptors.

TABLE 1

Three nucleotide extensions
(SEQ ID NO: of resulting customized 5' adaptor)

| AAA | AAU | AAC | AAG | GAA | GAU | GAC | GAG |
|---|---|---|---|---|---|---|---|
| (2) | (10) | (18) | (26) | (34) | (42) | (50) | (58) |
| UAU | UAC | UAG | UAA | AGU | AGC | AGG | AGA |
| (3) | (11) | (19) | (27) | (35) | (43) | (51) | (59) |
| AUC | AUG | AUA | AUU | ACC | ACG | ACA | ACU |
| (4) | (12) | (20) | (28) | (36) | (44) | (52) | (60) |
| UUG | UUA | UUU | UUC | UCG | UCA | UCU | UCC |
| (5) | (13) | (21) | (29) | (37) | (45) | (53) | (61) |
| GCA | GCU | GCC | GCG | GUA | GUU | GUC | GUG |
| (6) | (14) | (22) | (30) | (38) | (46) | (54) | (62) |
| CCU | CCC | CCG | CCA | CUU | CUC | CUG | CUA |
| (7) | (15) | (23) | (31) | (39) | (47) | (55) | (63) |
| CGC | CGG | CGA | CGU | CAC | CAG | CAA | CAU |
| (8) | (16) | (24) | (32) | (40) | (48) | (56) | (64) |
| GGG | GGA | GGU | GGC | UGG | UGA | UGU | UGC |
| (9) | (17) | (25) | (33) | (41) | (49) | (57) | (65) |

For Test 1, the 64 customized 5' adaptors were individually ligated with smRNA-3'adaptor molecules and smRNA libraries from eight adaptors pooled together for cluster generation and SBS. smRNA preparation was carried out using the Illumina manufacturer's protocols (Preparing Samples for Small RNA Sequencing Using the Alternative v1.5 Protocol, Small RNA sample prep Kit# FC-102-1009, Illumina Inc.) with minor optimization. Equal amounts of 20 human tissue RNAs from Ambion human total RNA survey panel (AM6000) were mixed as human total RNA pool in order to balance smRNA population and mimic the abundance and 3' and 5' heterogeneity of smRNA sequences. RNA in the pool was derived from adipose, bladder, brain, cervix, colon, esophagus, heart, kidney, liver, lung, ovary, placenta, prostate, skeletal muscle, small intestine, spleen, testes, thymus, thyroid, and trachea tissue. The RNA pool was used for smRNA library construction, cluster generation, and SBS. 1.0 µg of pooled total RNA was ligated to the default Illumina 3' adaptor (SEQ ID NO:66) with T4 RNA ligase 2 and truncated (New England BioLabs) at 22 ° C. for 1 hour; The 3' adaptor-miRNA ligation was then ligated to the default Illumina 5' adapter, one of the 64 customized 5' adaptors, or an 8, 16, 32, or 64 adaptor pool of customized 5' adaptors (0.5 µl of 5 µM per reaction) with T4 RNA ligase I (New England BioLabs) at 20° C. for 1 hour. The resultant smRNA library was reverse transcribed using GX1 (SEQ ID NO:67) as RT primer, then subjected to PCR amplification for 12 cycles using the primers GX1 and GX2 (SEQ ID NO:68). Amplified smRNAs were gel purified using a 6% TBE PAGE gel with size selection (for targeted smRNA of 17-32 nt). The purified library was quantified using qPCR with the forward primer of SEQ ID NO:69 and the reverse primer of SEQ ID NO:70, and the quantified denatured miRNA library was loaded in 1 ml hybridization buffer to a final DNA concentration of 8 pM and used for single read flow cell cluster generation. 42 cycle (42 nt) sequencing was performed using Illumina Genome Analyzer II (GAII).

Raw reads from Test 1 shown in Table 2 (set forth in the file "54435.8095.US00.txt" submitted herewith on CD-R), and the test results are summarized in Table 3. Total reads for each adaptor were normalized to a constant, and each miRNA was scaled up according to the ratio of constant to the total reads. Log2 transformed normalized reads were clustered and used to generate a heatmap (FIG. 2). Serious result biases were introduced by both the customized 5' adaptors and the default 5' adaptor. There were biases in the number of total reads, percentage of reads that were aligned to corresponding genomes, distribution of smRNAs to different categories, coverage of different species in the same smRNA population, and abundance of individual smRNAs. Read counts for some individual miRNAs were different by as much as 200-fold.

To eliminate the possibility that the smRNA reads processing software might be producing the bias, reads were profiled using different miRNA profiling software systems implemented with different data analysis algorithms. Reads from the 8-pool adaptors from lane 1 of Test 1 were profiled using miRExpress and Novoalign.

For Novoalign data processing, image analysis and base calling analysis were performed using the Illumina Genome Analysis Package (OLB v1.6 and CASAVA v1.6). The base calling analysis did not apply the Illumina default chastity filter, which discards about 30 to 40% of the reads with low quality from the first 25 bases being sequenced and generated 42-nt long reads in FASTQ format. Quality control of the reads was done during alignment by Novoalign software that filters out low quality reads by base quality score. Comparison studies showed that this Novoalign filters performed similarly to the Illumina default chastity filter. Reads were separated using Novobarcode software (http://www.novocraft.com), and aligned to human genome hg18 (NCBI build 36.1) using Novoalign software (http://www.novocraft.com) with default settings but for the following modifications: an aligned read requires a minimum of 16 nts in length with good base quality after 3' adapter trimming and a perfect match to the reference genome. A mapping table was created using the human miRNA mature sequences from miRBase 15 and aligned back to the hg18 genome afterwards. If a read was able to be aligned to multiple loci, it was randomly assigned to one locus. To summarize the expression levels of smRNAs, reads of a smRNA falling into the mapped smRNA regions within five base extensions were treated as valid reads and counted. If a smRNA could be mapped to multiple genome loci, the counts at each locus were summed as the total number of reads for that smRNA.

For statistical analysis of the miRNA expression levels, total count of miRNAs in each barcoded sample was scaled to a constant (1.7 million) and log2 transformed with an offset of one. MiRNAs with normalized reads over 6 in at least 10% of the samples were kept for subsequent expression correlation efficiency analysis. Hierarchical clustering with one-Pearson correlation as distance measurement and complete linkage was conducted with Cluster 3.0 and viewed in Java TreeView (de Hoon 2004; Saldanha 2004).

miRExpress software analyzed miRNAs by matching reads directly to pre-miRNA or mature miRNAs sequences (Wang 2009). The default setting was used to count reads that could perfectly match to pre-miRNAs.

Although the rank of miRNAs by read counts in miRExpress and Novoalign was not identical, read counts and abundance rank were comparable between the two programs (Table 4). These results establish that the data analysis algorithm is not a major cause for the sequencing bias.

Table 5 compares the results for the top 20 miRNAs with both the default 5' adaptor and the customized 5' adaptors. These results suggest that the default 5' adaptor is incapable of sequencing certain miRNAs (e.g., miR-1, -145, -215, -126 and -451), but favors others (e.g., miR-20a, -17, -155, -1246 and -146a).

TABLE 5

| Sorted by default 5' adaptor | | | Sorted by average of adaptors pool | | |
|---|---|---|---|---|---|
| miRNA | Pool-avg | Default | miRNA | Pool-avg | Default |
| hsa-miR-21 | 339251 | 1852326 | hsa-miR-143 | 1984995 | 17640 |
| hsa-miR-378 | 178769 | 1201524 | hsa-miR-1 | 429851 | 39 |
| hsa-let-7f | 211659 | 510653 | hsa-miR-21 | 339251 | 1852326 |
| hsa-miR-30e | 50344 | 238220 | hsa-let-7a | 221170 | 182815 |
| hsa-miR-30d | 68551 | 235117 | hsa-let-7f | 211659 | 510653 |
| hsa-miR-101 | 57845 | 194516 | hsa-miR-378 | 178769 | 1201524 |
| hsa-let-7a | 221170 | 182815 | hsa-miR-126 | 169586 | 2 |
| hsa-miR-142-3p | 69620 | 169524 | hsa-miR-30a | 140659 | 425 |
| hsa-miR-148a | 77003 | 167654 | hsa-miR-26a | 137699 | 23823 |
| hsa-miR-20a | 9939 | 138720 | hsa-miR-24 | 123388 | 1815 |
| hsa-miR-155 | 3910 | 118345 | hsa-miR-148a | 77003 | 167654 |
| hsa-miR-103 | 23391 | 97269 | hsa-miR-192 | 71314 | 12660 |
| hsa-miR-17 | 8244 | 75571 | hsa-miR-142-3p | 69620 | 169524 |
| hsa-let-7g | 47101 | 72910 | hsa-miR-30d | 68551 | 235117 |
| hsa-miR-140-3p | 38710 | 67006 | hsa-miR-146b-5p | 67342 | 51686 |
| hsa-miR-146b-5p | 67342 | 51686 | hsa-miR-145 | 67237 | 40 |
| hsa-miR-191 | 22303 | 49626 | hsa-miR-29a | 65488 | 40124 |
| hsa-miR-1246 | 6148 | 49235 | hsa-miR-101 | 57845 | 194516 |
| hsa-miR-146a | 8939 | 45680 | hsa-miR-215 | 57179 | 142 |
| hsa-miR-29a | 65488 | 40124 | hsa-miR-451 | 56674 | 5 |

Figure 3:
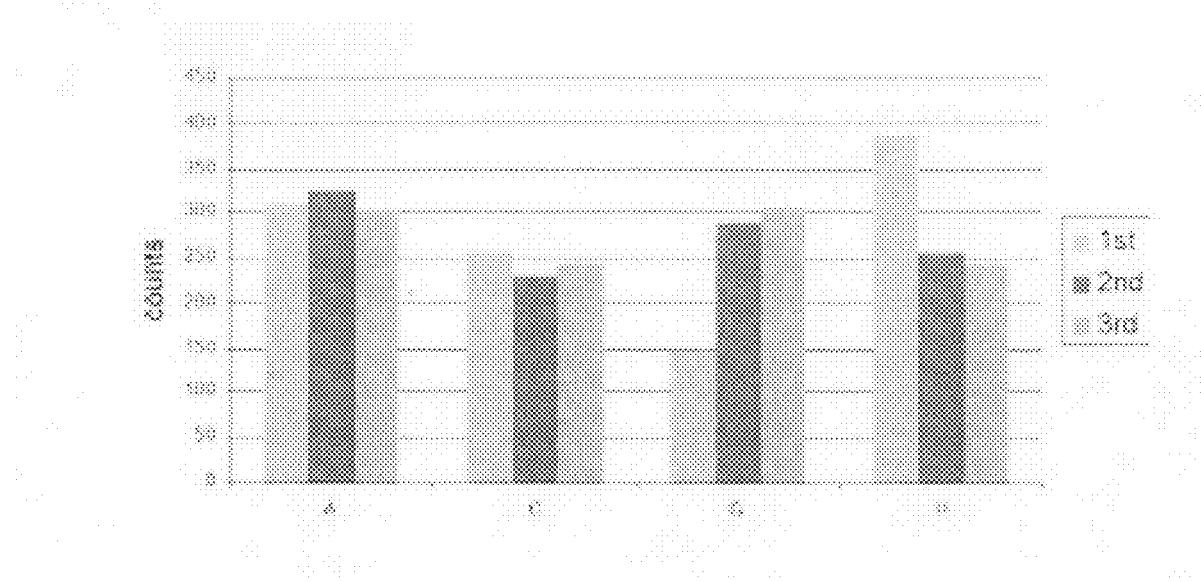
FIG. 3: ACGU distribution of the first three bases in all human miRNAs documented in miRBase 15.

Neither the distribution of the first three nts in the human miRNAs (FIG. 3) nor the secondary structures and thermal dynamic properties of the 64 adaptors (Table 3, columns 2, 3, and 9) were found to have a reasonable correlation with the result bias. Interestingly, the clustered Test 1 results revealed that all three added nts influenced the results. This clustering result was roughly divided into eight groups (FIG. 2). Based on these eight groups, the 64 customized adaptors were organized into eight designed pools of eight adaptors each (P1-P8) with balanced bases at each position. These 8×8 pools were merged to form four pools of 16 adaptors each (P17, P28, P35, and P46), the 16×4 pools were merged to form two pools of 32 adaptors each (P1357 and P2468), and the two 32×2 pools were merged to form a single pool of 64 adaptors (Pall). The pooling strategy is summarized in Table 6.

TABLE 6

|  | P1 | P2 | P3 | P4 | P5 | P6 | P7 | P8 |
|---|---|---|---|---|---|---|---|---|
| 8 × 8 pools | AAA | AAU | AAC | AAG | GAA | GAU | GAC | GAG |
|  | UAU | UAC | UAG | UAA | AGU | AGC | AGG | AGA |
|  | AUC | AUG | AUA | AUU | ACC | ACG | ACA | ACU |
|  | UUG | UUA | UUU | UUC | UCG | UCA | UCU | UCC |

TABLE 6-continued

|  | GCA | GCU | GCC | GCG | GUA | GUU | GUC | GUG |
|---|---|---|---|---|---|---|---|---|
|  | CCU | CCC | CCG | CCA | CUU | CUC | CUG | CUA |
|  | CGC | CGG | CGA | CGU | CAC | CAG | CAA | CAU |
|  | GGG | GGA | GGU | GGC | UGG | UGA | UGU | UGC |

|  | P17 | P28 | P35 | P46 |
|---|---|---|---|---|
| 16 × 4 pools | P1 P7 | P2 P8 | P3 P5 | P4 P6 |
|  | P1357 |  |  | P2468 |
| 32 × 2 pools | P17 P35 |  |  | P28 P46 |
|  |  | Pall |  |  |
| 64 × 1 pool |  | P1357 P2468 |  |  |

Figure 4:
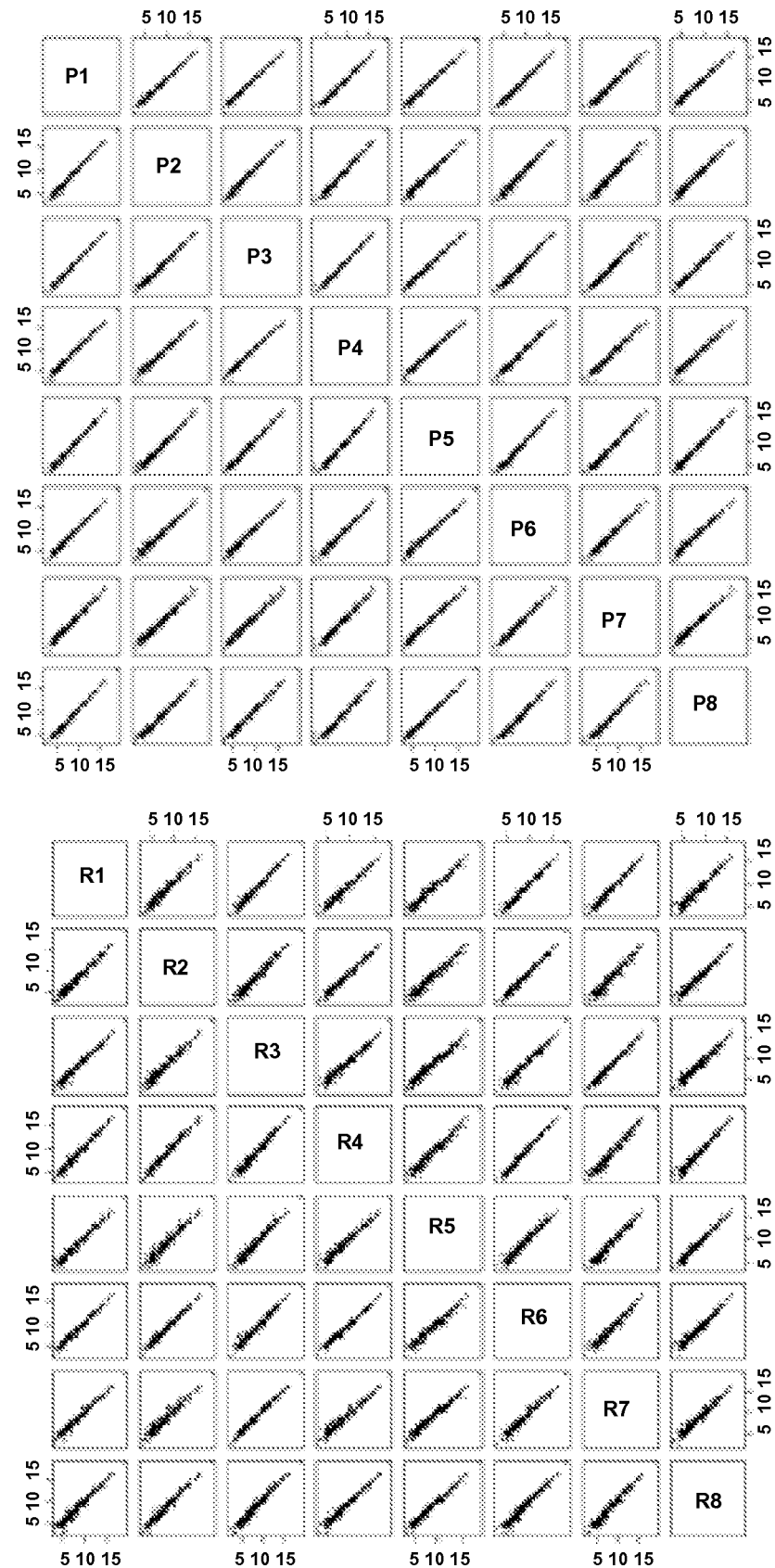
FIG. 4: miRNA expression variation as measured using designed 8×8 adaptor pools (P1 to P8) and randomized adaptor pools (R1 to R8).
Figure 5:
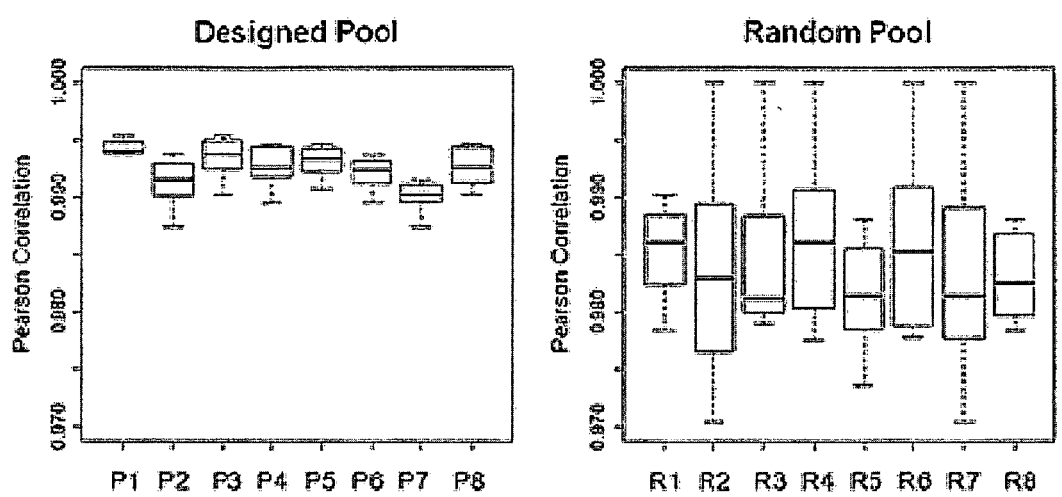
FIG. 5: Pearson correlation of designed 8×8 adaptor pools (P1 to P8) versus randomized adaptor pools (R1 to R8).
Figure 12:
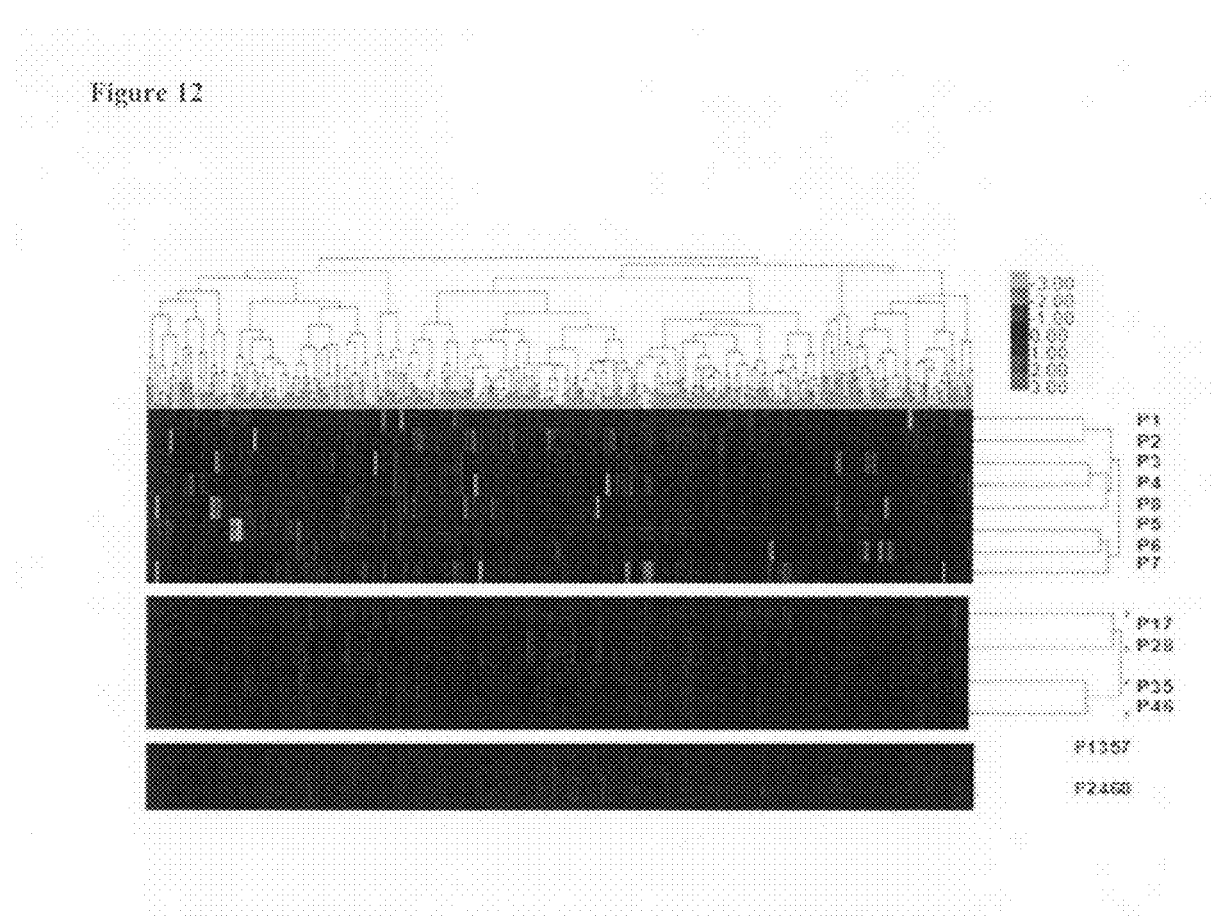
FIG. 12: Heatmaps of 8×8 pools versus 16×4 pools versus 32×2 pools in Test 1. These results indicate that index pooling reduced miRNA expression variation.
Figure 13:
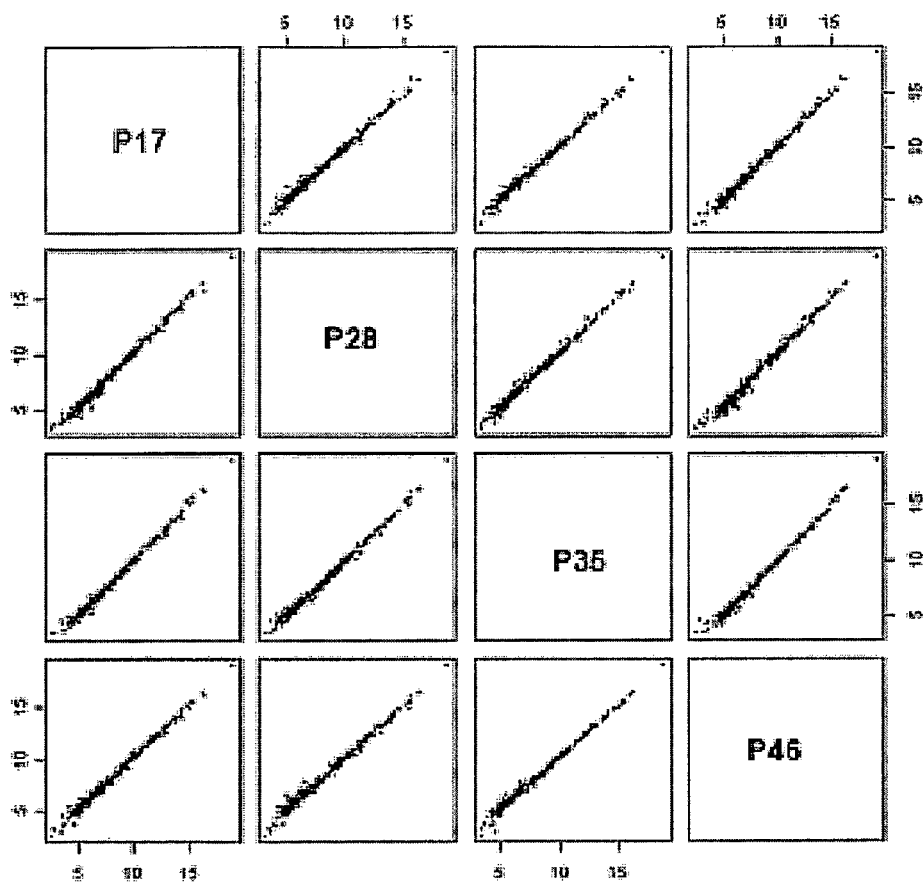
FIG. 13: Re-analyzed data of Test 1. Data was reorganized by 16×4 adaptor pools. These results indicate that miRNA expression between designed pools shows less variation.
Figure 14:
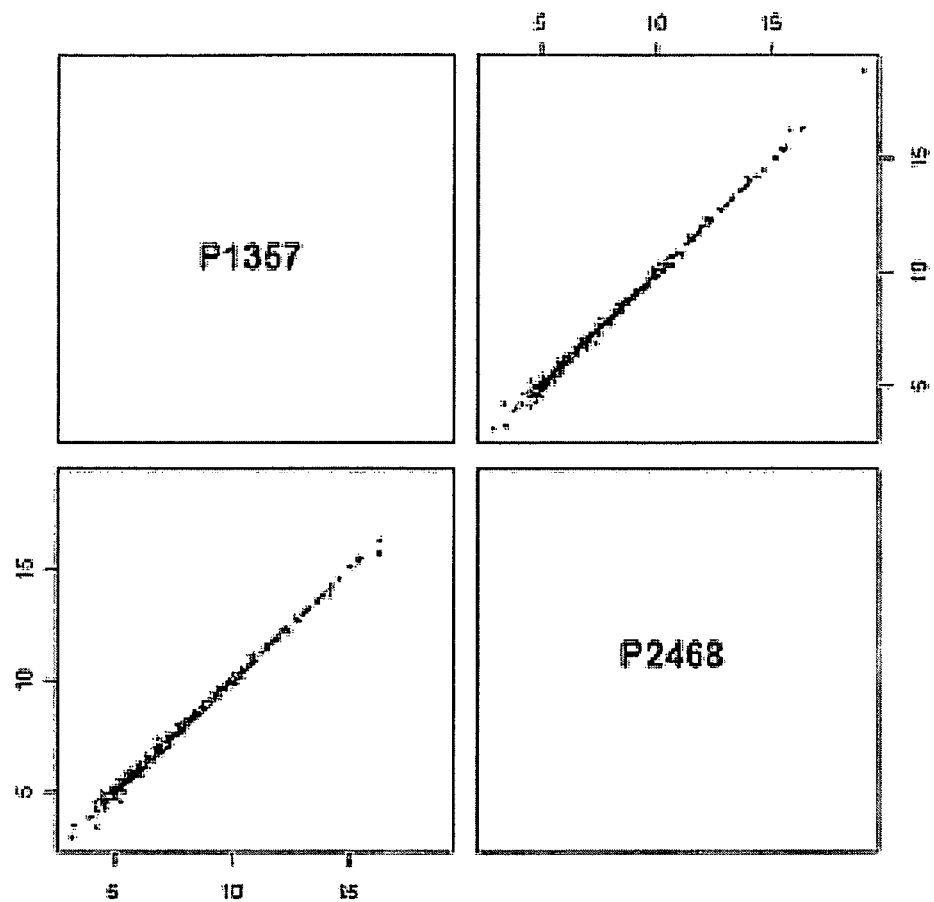
FIG. 14: Re-analyzed data of Test 1. Data was reorganized by 32×2 adaptor pools. These results indicate that miRNA expression between pools shows even less variation.

Correlation efficiency showed that the designed pools of 8 adaptors provided significantly more compact results than randomized pools of 8 adaptors, with the designed pools showing less miRNA expression variation than the randomized pools (FIGS. 4 and 5). Pooled results from Test 1 indicate that index pooling reduced miRNA expression variation, with larger index pools resulting in less miRNA expression bias among same size pools (FIG. 12-14).

Figure 6:
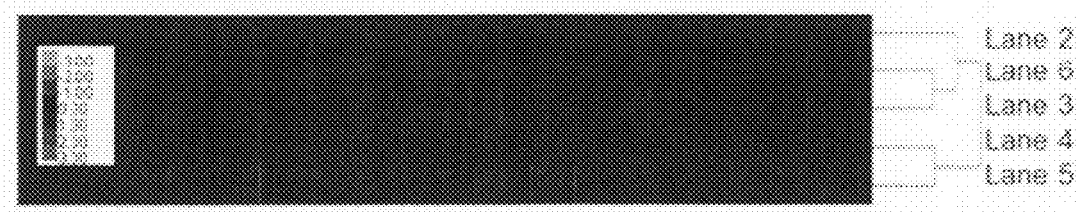
FIG. 6: Heatmap from Test 2. Lanes 2 and 6, duplicate run of 8'8 pools; Lane 3, 16×4 pools; Lane 4, 32×2 pools; Lane 5: 64×1 pool. Total reads of miRNAs in different lanes were normalized and log2 transformed to generate the heatmap.
Figure 7:
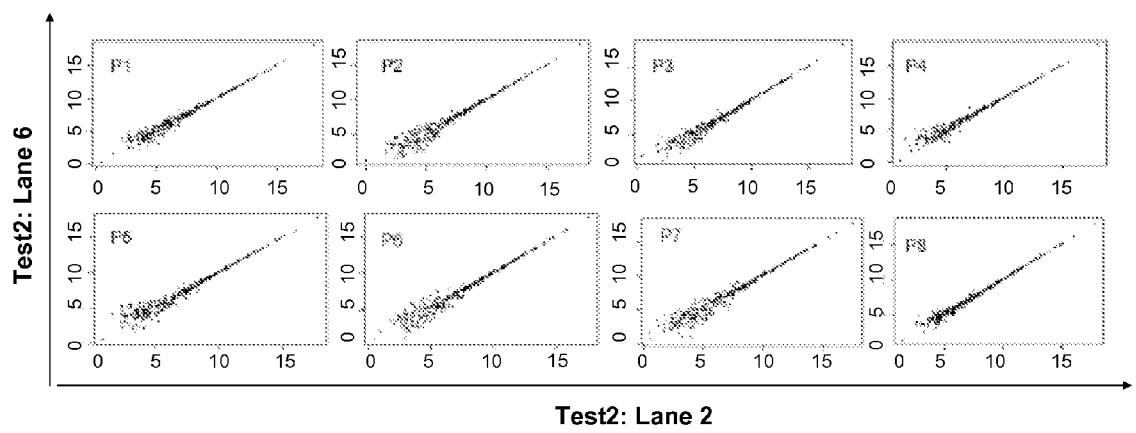
FIG. 7: Normalized, log2 transformed miRNA read counts from Lane 2 (X-axis) and Lane 6 (Y-axis) of Test 2.

For Test 2, the designed adaptor pools were used for 5' adaptor ligation to smRNA-3'adaptors. This approach allowed for the use of one group of 8, 16, 32, or 64 adaptors to barcode one sample. Consistent results were observed across all the adaptor pools (FIGS. 6 and 7, Table 7) The use of pools containing 16 adaptors was sufficient to minimize results bias (FIGS. 8-10), and miRNA expression measurement between the 16, 32, and 64 adaptor pools showed about 99% correlation (FIG. 6). Correlation efficiency using the 16 adaptor pool to run four samples per flowcell versus running one sample was about 0.99. Only about 10% of miRNAs were undetectable in the four sample run compared to the one sample run (Table 8). The 10% missed were typically less abundant miRNAs. Therefore, the use of 16 adaptor pools to barcode four samples per flowcell is sufficient to identify all highly expressed miRNAs with an expression measurement that is comparable to that obtained with one sample per lane.

TABLE 8

| 16 × 4 pool results | miRBase 15 | All in lane 4-Test 2 | P17 in Lane 4-Test 2 | P28 in Lane 4-Test 2 | P35 in Lane 4-Test 2 | P46 in Lane 4-Test 2 |
|---|---|---|---|---|---|---|
| Unique miRNAs | 1100 | 763 | 666 | 664 | 678 | 663 |

Comparison of Test 2 data showed the profiling coverage of miRNAs increased by almost 100% using the pooled adaptors versus the default 5' adaptor (Table 9).

TABLE 9

| Raw read counts | Default adaptor | 64 × 1 pool | 32 × 2 pool | 16 × 4 pool | 8 × 8 pool (Lane 2) | 8 × 8 pool (Lane 6) |
|---|---|---|---|---|---|---|
|  | miRNA coverage measured by unique miRNA sequences (1100 in miRBase 15) | | | | | |
| ≥1 | 461 | 776 | 760 | 763 | 774 | 769 |
| ≥5 | 348 | 636 | 643 | 627 | 625 | 645 |

TABLE 9-continued

| Raw read counts | Default adaptor | 64 × 1 pool | 32 × 2 pool | 16 × 4 pool | 8 × 8 pool (Lane 2) | 8 × 8 pool (Lane 6) |
|---|---|---|---|---|---|---|
|  | miRNA coverage measured by unique miRNA sequences (1100 in miRBase 15) | | | | | |
| ≥10 | 297 | 573 | 583 | 573 | 575 | 579 |
| ≥100 | 189 | 379 | 383 | 364 | 373 | 382 |
| ≥1000 | 93 | 184 | 184 | 171 | 174 | 179 |

Reads from all runs in both Test 1 and Test 2 showed that 893 miRNAs were detected (Table 10). This represents about 81% of the 1,100 human mature miRNA/miRNA* sequences documented in miRBase 15.

TABLE 10

| miRNA raw read counts | miRNA coverage measured by unique miRNA sequences (Test 1 + Test 2) | By % |
|---|---|---|
| ≥1 | 893 | 81.18 |
| ≥5 | 821 | 74.64 |
| ≥10 | 776 | 70.55 |
| ≥100 | 603 | 54.82 |
| ≥1000 | 407 | 37.00 |

The low coverage and bias of the Illumina default adaptor may play a role in detecting low abundance miRNA and miRNA*. The miRNA* family are classified as low abundance strands from the same precursor miRNA. However, in the experiments disclosed herein, the abundance was reversed for 21 pairs of miRNA/miRNA*, with 28 miRNAs detected at less than 10 times the abundance of their corresponding miRNA* (Table 11).

Figure 9A:
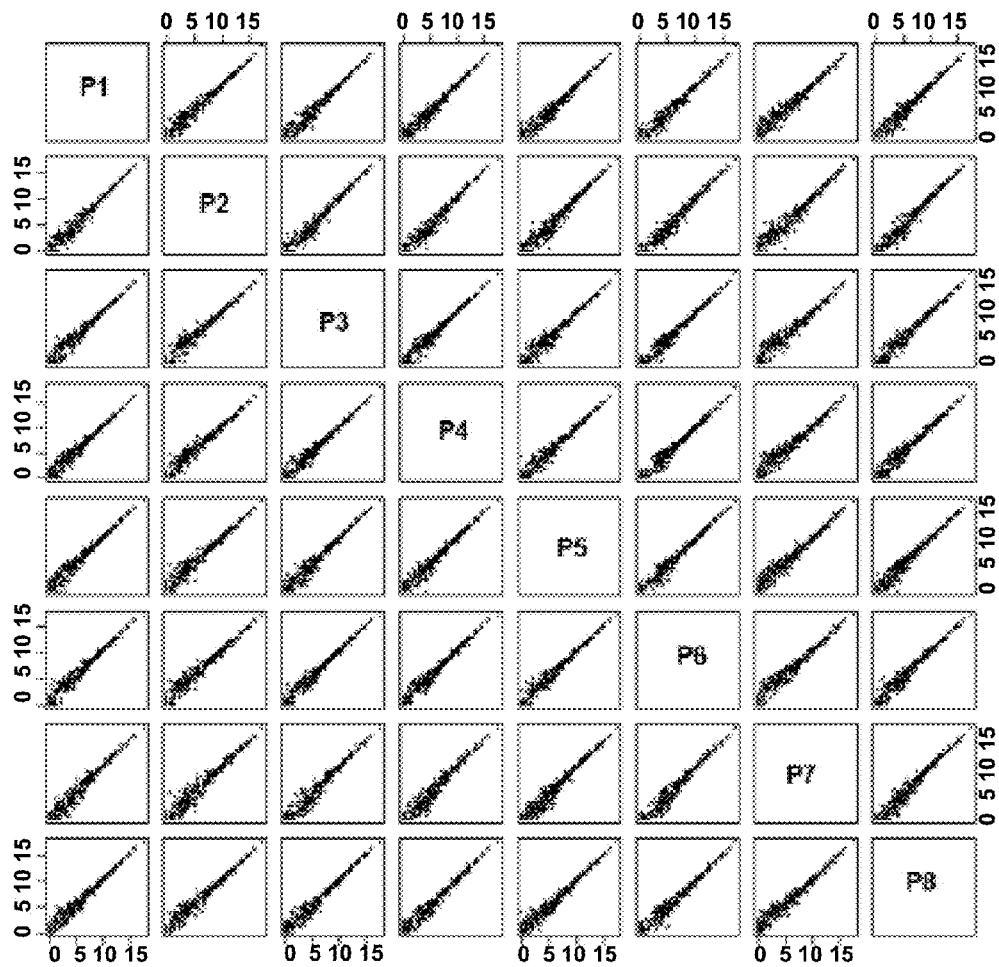
FIG. 9: A. Reproducibility among eight adaptor pools. Normalized, log2 transformed miRNA read counts from Lane 7 of Test 2 using breast RNA were plotted by adaptor pools. B. Heatmap of breast RNA eight adaptor pooling results.
Figure 9B:
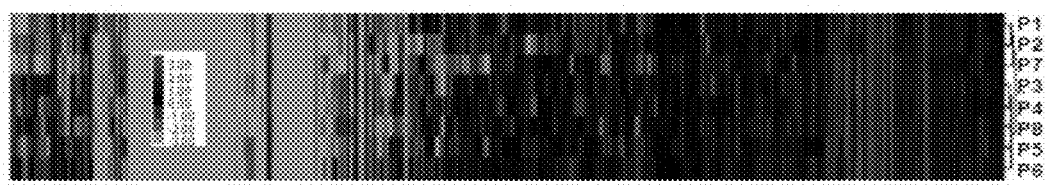
Figure 10:
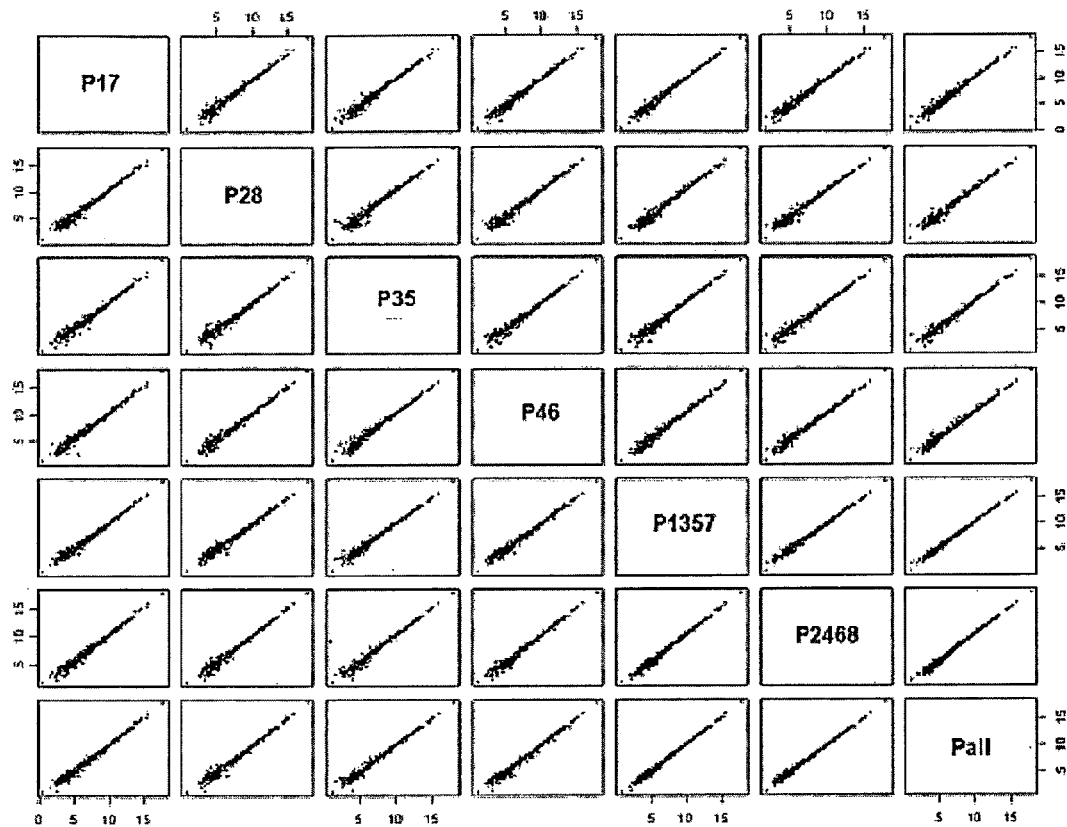
FIG. 10: Reproducibility among 16, 32, and 64 adaptor pools. Normalized, log2 transformed miRNA read counts from Test 2 using breast RNA were plotted by adaptor pools.

To validate the pooling strategy, breast tissue total RNA (#AM6952, Table 7) and human pooled total RNA was sequenced using the eight adaptor pools or the default Illumina 5' adaptor. The results showed consistent performance among the eight adaptor pools (FIG. 9). The relative abundance of miR-21, -1, -126, -101, and -205 in breast RNA and pooled human tissue RNA as measured by normalized read counts is set forth in Table 12. The eight adaptor pools were effective at identifying all five miRNAs in both tissue samples, while the default adaptor over-reported two (miR-21 and miR-101) and was largely ineffective at identifying the other three (miR-1, miR-126, and mi-R205).

TABLE 12

| RNA source 5' Adaptor | Human RNA pool Default | Human RNA pool 8 × 8 pool | Breast RNA 8 × 8 pool |
|---|---|---|---|
| hsa-miR-21 | 1911436 | 368479 | 488594 |
| hsa-miR-1 | 40 | 450370 | 2909 |
| hsa-miR-126 | 2 | 175101 | 222838 |
| hsa-miR-101 | 200723 | 61050 | 77431 |
| hsa-miR-205 | 0 | 5408 | 90397 |

Next, expression levels of miR-21, -1, -126, -101, and -205 in breast RNA versus pooled human tissue RNA were evaluated by Northern blot as previously described (Sun 2009). 20 µg of human pooled total RNA or breast total RNA were loaded onto a 12% PAGE/8M urea gel. Northern blot results were consistent with the eight adaptor pool sequencing results from both breast RNA and pooled human RNA (FIG. 11). However, the Northern blot results were not consistent with the default adaptor sequencing results from pooled RNA tissue. These results further verify the superiority of miRNA tagging and sequencing using the pooled adaptors versus the default Illumina adaptor.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Bartel, Cell 136:215 (2009)
2. Chiang et al., Genes Dev 24:992 (2010)
3. Cronn et al., Nucl Acids Res 36:e122 (2008)
4. Cummins et al., Proc Natl Acad Sci USA 103:3687 (2006)
5. de Hoon et al., Bioinformatics 20:1453 (2004)
6. Ender et al., Mol Cell 32:519 (2008)
7. Galasso et al., Genome Med 2:12 (2010)
8. Goff et al., PLoS One 4:e7192 (2009)
9. Griffiths-Jones, Curr Protoc Bioinformatics Chapter 12, Unit 12.9.1 (2010)
10. Hafner et al., Methods 44:3 (2008)
11. Kim et al., Nat Rev Mol Cell Biol 10:126 (2009)
12. Lagos-Quintana et al., Science 294:853 (2001)
13. Lau et al., Science 294:858 (2001)
14. Lee et al., Cell 75:843 (1993)
15. Lee et al., Science 294:862 (2001)
16. Levin et al., Nat Methods 7:709 (2010)
17. Linsen et al., Nat Methods 6:474 (2009)
18. Lu et al., Science 309:1567 (2005)
19. Lu et al., Methods 43:110 (2007)
20. Nagpal et al., Curr Mol Med 10:503 (2010)
21. Pasquinelli et al., Nature 408:86 (2000)
22. Pederson, RNA 16:1865 (2010)
23. Pfeffer et al., Curr Protoc Mol Biol Chapter 26, Unit 26.4 (2005)
24. Reinhart et al., Nature 403:901 (2000)
25. Riedmann & Schwentner, RNA Biol 7:133 (2010)
26. Saldanha, Bioinformatics 20:3246 (2004)
27. Sun et al., RNA 15:1640 (2009)
28. Taft et al., RNA 15:1233 (2009)
29. Tang et al., Nat Protoc 5:516 (2010)
30. Thomson & Lin, Annu Rev Cell Dev Biol 25:355 (2009)
31. Tian et al., BMC Biotechnol 10:64 (2010)
32. Wang et al., BMC Bioinformatics 10:328 (2009)
33. Wightman et al., Cell 75:855 (1993)
34. Witten et al., BMC Biol 8:58 (2010)
35. Wu et al., PLoS One 2:e1020 (2007)

TABLE 3

| Last 3 nts of custom adaptor | # of secondary structures predicted by QuikFold 3.0 | # of G and C nts in adaptor | # of total reads | # of reads that passed filter of Novoalignment | # of reads that can be aligned to human genome 18 | % of reads that passed filter | Correlation of miRNA with average # of miRNA in all adaptors (linear scale) | Count of miRNAs with same 1st three nts as the last 3 nts of the custom adaptor |
|---|---|---|---|---|---|---|---|---|
| AAA | 5 | 0 | 2,873,823 | 2,602,433 | 1,854,870 | 71.3% | 0.9836 | 47 |
| AAU | 5 | 0 | 2,363,426 | 2,174,865 | 1,577,744 | 72.5% | 0.9852 | 19 |
| AAC | 5 | 1 | 2,443,514 | 2,221,513 | 1,584,608 | 71.3% | 0.9846 | 20 |
| AAG | 5 | 1 | 2,294,143 | 1,650,306 | 1,072,384 | 65.0% | 0.9848 | 21 |
| ACA | 5 | 1 | 2,659,638 | 2,466,420 | 2,065,694 | 83.8% | 0.9716 | 11 |
| ACU | 5 | 1 | 1,865,696 | 1,748,929 | 1,422,241 | 81.3% | 0.9691 | 31 |
| ACC | 5 | 2 | 2,427,509 | 2,022,047 | 1,489,387 | 73.7% | 0.9844 | 12 |
| ACG | 5 | 2 | 2,141,983 | 1,596,426 | 1,264,670 | 79.2% | 0.9899 | 5 |
| AUA | 5 | 0 | 2,943,442 | 2,767,906 | 2,086,642 | 75.4% | 0.9886 | 12 |
| AUU | 5 | 0 | 1,819,682 | 1,715,885 | 1,324,440 | 77.2% | 0.9810 | 8 |
| AUC | 5 | 1 | 2,280,279 | 2,150,454 | 1,464,065 | 68.1% | 0.9663 | 21 |
| AUG | 5 | 1 | 2,005,752 | 1,663,633 | 1,226,855 | 73.7% | 0.9853 | 14 |
| AGA | 7 | 1 | 1,866,123 | 1,496,581 | 1,092,992 | 73.0% | 0.9891 | 23 |
| AGC | 5 | 2 | 4,100,291 | 2,246,985 | 1,615,537 | 71.9% | 0.9845 | 15 |
| AGU | 6 | 1 | 2,266,066 | 2,096,199 | 1,493,172 | 71.2% | 0.9894 | 13 |
| AGG | 3 | 2 | 2,186,275 | 482,034 | 319,862 | 66.4% | 0.9905 | 38 |
| UAA | 1 | 0 | 2,186,275 | 482,034 | 319,862 | 77.8% | 0.9855 | 32 |
| UAU | 1 | 0 | 3,689,221 | 3,421,227 | 2,703,636 | 79.0% | 0.9853 | 19 |
| UAC | 1 | 1 | 3,075,174 | 2,744,694 | 2,193,399 | 79.9% | 0.8707 | 17 |
| UAG | 1 | 1 | 3,090,672 | 2,617,560 | 1,817,026 | 69.4% | 0.9793 | 28 |
| UCA | 1 | 1 | 2,830,564 | 2,587,389 | 1,998,448 | 77.2% | 0.5842 | 24 |
| UCU | 1 | 1 | 1,900,004 | 1,577,456 | 1,148,322 | 72.8% | 0.3917 | 24 |
| UCC | 1 | 2 | 1,733,729 | 1,531,841 | 1,131,036 | 73.8% | 0.5377 | 24 |
| UCG | 1 | 2 | 3,255,088 | 2,672,867 | 1,860,778 | 69.6% | 0.3742 | 12 |
| UUA | 3 | 0 | 2,064,236 | 1,908,719 | 1,541,108 | 80.7% | 0.6899 | 13 |
| UUU | 3 | 0 | 2,869,685 | 2,596,616 | 2,071,204 | 79.8% | 0.7896 | 19 |
| UUC | 3 | 1 | 2,415,109 | 2,267,877 | 1,768,381 | 78.0% | 0.9945 | 25 |
| UUG | 3 | 1 | 2,367,315 | 2,098,963 | 1,685,140 | 80.3% | 0.6990 | 17 |
| UGA | 1 | 1 | 615,726 | 506,892 | 366,514 | 72.3% | 0.9819 | 38 |
| UGC | 1 | 2 | 2,500,231 | 2,034,397 | 1,530,145 | 75.2% | 0.9846 | 21 |
| UGU | 2 | 1 | 2,778,109 | 2,528,513 | 1,826,787 | 72.2% | 0.6044 | 31 |
| UGG | 2 | 2 | 2,295,023 | 1,279,694 | 897,849 | 70.2% | 0.9784 | 43 |
| CAA | 7 | 1 | 2,085,449 | 1,950,978 | 1,443,135 | 74.0% | 0.9846 | 36 |
| CAU | 7 | 1 | 2,577,649 | 2,446,969 | 1,844,074 | 75.4% | 0.9865 | 14 |
| CAC | 7 | 2 | 2,154,266 | 1,979,033 | 1,505,862 | 76.1% | 0.9886 | 15 |
| CAG | 7 | 2 | 2,980,868 | 2,160,044 | 1,528,713 | 70.8% | 0.9818 | 24 |
| CCA | 7 | 2 | 1,947,457 | 1,750,754 | 1,376,395 | 78.6% | 0.9865 | 16 |
| CCU | 7 | 2 | 1,877,313 | 1,701,980 | 1,260,847 | 74.1% | 0.9864 | 19 |

TABLE 3-continued

| Last 3 nts of custom adaptor | # of secondary structures predicted by QuikFold 3.0 | # of G and C nts in adaptor | # of total reads | # of reads that passed filter of Novoalignment | # of reads that can be aligned to human genome 18 | % of reads that passed filter | Correlation of miRNA with average # of miRNA in all adaptors (linear scale) | Count of miRNAs with same 1st three nts as the last 3 nts of the custom adaptor |
|---|---|---|---|---|---|---|---|---|
| CCC | 7 | 3 | 1,765,335 | 1,417,864 | 989,471 | 69.8% | 0.9830 | 13 |
| CCG | 9 | 3 | 1,579,577 | 1,307,675 | 1,032,027 | 78.9% | 0.9909 | 4 |
| CUA | 7 | 1 | 1,846,184 | 1,721,094 | 1,294,698 | 75.2% | 0.9280 | 14 |
| CUU | 7 | 1 | 2,883,730 | 2,695,491 | 2,070,122 | 76.8% | 0.9830 | 14 |
| CUC | 8 | 2 | 2,912,793 | 2,526,398 | 1,849,228 | 73.2% | 0.9913 | 27 |
| CUG | 9 | 2 | 3,648,901 | 3,127,550 | 2,478,456 | 79.2% | 0.8337 | 34 |
| CGA | 3 | 2 | 3,174,936 | 2,740,749 | 1,975,732 | 72.1% | 0.9906 | 3 |
| CGC | 8 | 3 | 3,233,287 | 2,237,951 | 1,629,380 | 72.8% | 0.9894 | 5 |
| CGU | 8 | 2 | 3,043,880 | 2,731,024 | 2,038,981 | 74.7% | 0.9942 | 5 |
| CGG | 1 | 3 | 3,543,206 | 659,906 | 461,155 | 69.9% | 0.9502 | 12 |
| GAA | 4 | 1 | 4,601,179 | 4,100,429 | 2,849,364 | 69.5% | 0.9879 | 15 |
| GAU | 3 | 1 | 4,017,562 | 3,718,452 | 2,681,945 | 72.1% | 0.9914 | 5 |
| GAC | 4 | 2 | 3,865,704 | 3,282,978 | 2,272,584 | 69.2% | 0.9910 | 5 |
| GAG | 3 | 2 | 4,079,254 | 2,397,622 | 1,564,181 | 65.2% | 0.9872 | 9 |
| GCA | 7 | 2 | 3,348,917 | 2,892,130 | 2,310,215 | 79.9% | 0.9460 | 13 |
| GCU | 7 | 2 | 3,741,695 | 3,506,723 | 2,667,236 | 76.1% | 0.9348 | 11 |
| GCC | 7 | 3 | 3,236,164 | 2,627,147 | 1,752,991 | 66.7% | 0.9554 | 7 |
| GCG | 7 | 3 | 4,033,566 | 2,305,468 | 1,704,092 | 73.9% | 0.9737 | 4 |
| GUA | 2 | 1 | 3,131,513 | 1,847,377 | 824,577 | 44.6% | 0.9191 | 2 |
| GUU | 8 | 1 | 3,347,839 | 3,036,625 | 2,037,159 | 67.1% | 0.8761 | 6 |
| GUC | 1 | 2 | 3,048,292 | 2,591,672 | 1,619,189 | 62.5% | 0.9666 | 6 |
| GUG | 4 | 2 | 2,472,107 | 1,896,957 | 1,195,374 | 63.0% | 0.7264 | 23 |
| GGA | 2 | 2 | 3,092,035 | 2,550,386 | 1,405,444 | 55.1% | 0.8136 | 6 |
| GGC | 3 | 3 | 3,190,015 | 1,377,083 | 911,604 | 66.2% | 0.8605 | 10 |
| GGU | 2 | 2 | 2,475,086 | 1,979,666 | 1,212,320 | 61.2% | 0.9597 | 7 |
| GGG | 3 | 3 | 4,653,050 | 1,637,713 | 977,341 | 59.7% | 0.7433 | 19 |

TABLE 4

| Rank | miRNA | AAA | AAT | CTC | CTT | GGG | GTG | TCA | TCC | sum |
|---|---|---|---|---|---|---|---|---|---|---|
| | | | | miRExpress software | | | | | | |
| 1 | hsa-miR-143 | 629047 | 596534 | 264042 | 259410 | 49059 | 100716 | 59682 | 21985 | 1980475 |
| 2 | hsa-miR-378 | 36063 | 53471 | 42317 | 54587 | 16247 | 28919 | 126718 | 57710 | 416032 |
| 3 | hsa-miR-1 | 57848 | 44332 | 39707 | 10420 | 71826 | 135691 | 29183 | 16259 | 405266 |
| 4 | hsa-miR-21 | 56293 | 54594 | 30282 | 46590 | 12227 | 15423 | 73223 | 35705 | 324337 |
| 5 | hsa-miR-30a | 18225 | 21466 | 16951 | 22039 | 9302 | 13824 | 71561 | 25377 | 198745 |
| 6 | hsa-let-7a | 73073 | 55464 | 6234 | 8420 | 8281 | 10661 | 15513 | 5619 | 183265 |
| 7 | hsa-let-7f | 80747 | 61375 | 3623 | 6323 | 4201 | 9192 | 11917 | 4434 | 181812 |
| 8 | hsa-miR-126 | 21192 | 17954 | 10190 | 13560 | 10448 | 25185 | 32341 | 8650 | 139520 |
| 9 | hsa-miR-26a | 18178 | 12543 | 15896 | 37425 | 6207 | 9273 | 16873 | 9698 | 126093 |
| 10 | hsa-miR-148a | 13804 | 11033 | 13926 | 20902 | 12155 | 5385 | 12584 | 2984 | 92773 |
| 11 | hsa-miR-215 | 12043 | 10792 | 13911 | 6560 | 3232 | 17876 | 18218 | 5473 | 88105 |
| 12 | hsa-miR-192 | 11751 | 11388 | 8808 | 6573 | 5710 | 9914 | 19675 | 6537 | 80356 |
| 13 | hsa-miR-101 | 7582 | 8456 | 7582 | 10921 | 3174 | 6450 | 20984 | 10424 | 75573 |
| 14 | hsa-miR-30d | 9416 | 9847 | 7963 | 8538 | 4882 | 8059 | 15766 | 6778 | 71249 |
| 15 | hsa-miR-10b | 9009 | 10431 | 6283 | 7604 | 4005 | 4395 | 19467 | 9012 | 70206 |
| 16 | hsa-miR-451 | 15361 | 10057 | 7584 | 7501 | 2597 | 2635 | 10609 | 6821 | 63165 |
| 17 | hsa-miR-145 | 2744 | 2847 | 10661 | 9089 | 4226 | 7679 | 11457 | 8859 | 57562 |
| 18 | hsa-miR-27b | 8511 | 6649 | 7872 | 9957 | 3741 | 2958 | 9543 | 4668 | 53899 |
| 19 | hsa-miR-140-3p | 7200 | 6803 | 7626 | 10477 | 3511 | 3559 | 6379 | 5750 | 51305 |
| 20 | hsa-miR-24 | 5128 | 3009 | 9244 | 3013 | 7118 | 9415 | 7554 | 4633 | 49114 |
| | | | | Novoalign software | | | | | | |
| 1 | hsa-miR-143 | 619600 | 588860 | 261006 | 257701 | 57043 | 99605 | 60485 | 21845 | 1966145 |
| 2 | hsa-miR-1 | 58842 | 45204 | 39539 | 10656 | 74017 | 137450 | 29480 | 16454 | 411642 |
| 3 | hsa-miR-21 | 56707 | 54428 | 30261 | 46984 | 12404 | 15381 | 73132 | 35673 | 324970 |
| 4 | hsa-miR-378 | 34181 | 51292 | 40421 | 52081 | 16619 | 27345 | 119105 | 54877 | 395921 |
| 5 | hsa-let-7f | 81639 | 62336 | 3727 | 6472 | 4770 | 9475 | 12242 | 4524 | 185185 |
| 6 | hsa-let-7a | 72376 | 55159 | 6190 | 8391 | 8775 | 13750 | 15523 | 5614 | 185778 |
| 7 | hsa-miR-30a | 18195 | 21486 | 16923 | 22285 | 9600 | 13915 | 71336 | 25348 | 199088 |
| 8 | hsa-miR-26a | 17701 | 12617 | 15479 | 38064 | 6365 | 8978 | 16648 | 9446 | 125298 |
| 9 | hsa-miR-126 | 20722 | 17592 | 9962 | 13332 | 10604 | 24737 | 31622 | 8487 | 137058 |
| 10 | hsa-miR-24 | 5094 | 2979 | 9192 | 3026 | 7340 | 9417 | 7490 | 4594 | 49132 |
| 11 | hsa-miR-148a | 13547 | 10840 | 13693 | 20651 | 12760 | 5338 | 12467 | 2945 | 92241 |
| 12 | hsa-miR-215 | 11939 | 13790 | 13676 | 6407 | 3774 | 17552 | 17856 | 5352 | 90346 |
| 13 | hsa-miR-192 | 11557 | 11232 | 8651 | 6496 | 5648 | 9717 | 19311 | 6395 | 79007 |

TABLE 4-continued

| Rank | miRNA | AAA | AAT | CTC | CTT | GGG | GTG | TCA | TCC | sum |
|---|---|---|---|---|---|---|---|---|---|---|
| 14 | hsa-miR-30d | 9362 | 9801 | 7964 | 8616 | 4963 | 8177 | 15716 | 6767 | 71366 |
| 15 | hsa-miR-101 | 7589 | 8328 | 7469 | 10798 | 3144 | 6385 | 20665 | 10339 | 74717 |
| 16 | hsa-miR-146b-5p | 6947 | 6492 | 3325 | 3180 | 8576 | 7638 | 10232 | 1814 | 48204 |
| 17 | hsa-miR-145 | 2685 | 2797 | 10421 | 8912 | 4111 | 7447 | 11085 | 8628 | 56086 |
| 18 | hsa-miR-451 | 15263 | 9893 | 7453 | 7354 | 2578 | 2577 | 10438 | 6706 | 62262 |
| 19 | hsa-miR-10b | 8838 | 10204 | 6145 | 7515 | 4054 | 4383 | 19157 | 8867 | 69163 |
| 20 | hsa-miR-27b | 8140 | 6394 | 7546 | 10720 | 3945 | 2848 | 9217 | 4493 | 53303 |

TABLE 7

| | Human RNA pool adaptors | | | | | | Breast |
|---|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-let-7a | 182815 | 207044 | 201770 | 228567 | 250250 | 229745 | 285909 |
| hsa-let-7a* | 191 | 183 | 156 | 229 | 243 | 178 | 321 |
| hsa-let-7a-2* | 0 | 10 | 14 | 22 | 19 | 13 | 8 |
| hsa-let-7b | 3732 | 38250 | 37832 | 43779 | 45636 | 42083 | 104331 |
| hsa-let-7b* | 7 | 168 | 150 | 202 | 204 | 167 | 305 |
| hsa-let-7c | 4493 | 38771 | 37083 | 42216 | 46566 | 42940 | 42483 |
| hsa-let-7c* | 1 | 2 | 4 | 2 | 5 | 3 | 6 |
| hsa-let-7d | 9918 | 4502 | 4469 | 5067 | 4961 | 4926 | 3779 |
| hsa-let-7d* | 698 | 958 | 929 | 1221 | 1170 | 1079 | 1078 |
| hsa-let-7e | 249 | 8159 | 7300 | 7306 | 6986 | 9357 | 6280 |
| hsa-let-7e* | 0 | 51 | 58 | 78 | 81 | 77 | 47 |
| hsa-let-7f | 510653 | 201473 | 192459 | 203236 | 227113 | 225547 | 159271 |
| hsa-let-7f-1* | 62 | 20 | 20 | 32 | 18 | 16 | 28 |
| hsa-let-7f-2* | 80 | 2 | 6 | 4 | 5 | 5 | 9 |
| hsa-let-7g | 72910 | 42837 | 43556 | 50078 | 53190 | 47164 | 53943 |
| hsa-let-7g* | 43 | 219 | 245 | 315 | 328 | 256 | 167 |
| hsa-let-7i | 5027 | 8012 | 7610 | 8665 | 8993 | 8867 | 9347 |
| hsa-let-7i* | 113 | 304 | 314 | 419 | 420 | 318 | 426 |
| hsa-miR-1 | 39 | 404787 | 408176 | 485549 | 509267 | 450370 | 1790 |
| hsa-miR-100 | 1 | 24727 | 23218 | 27907 | 27055 | 26815 | 6954 |
| hsa-miR-100* | 0 | 38 | 27 | 39 | 33 | 30 | 5 |
| hsa-miR-101 | 194516 | 55392 | 50631 | 59094 | 59555 | 61050 | 47642 |
| hsa-miR-101* | 133 | 369 | 376 | 446 | 444 | 413 | 235 |
| hsa-miR-103 | 97269 | 20956 | 17889 | 14087 | 12536 | 23100 | 8047 |
| hsa-miR-103-2* | 37 | 20 | 14 | 31 | 21 | 20 | 22 |
| hsa-miR-103-as | 0 | 0 | 0 | 0 | 0 | 0 | 0 |
| hsa-miR-105 | 0 | 11 | 8 | 18 | 10 | 7 | 0 |
| hsa-miR-105* | 0 | 0 | 2 | 0 | 0 | 0 | 0 |
| hsa-miR-106a | 394 | 2073 | 2034 | 2465 | 2622 | 2258 | 829 |
| hsa-miR-106a* | 0 | 4 | 11 | 10 | 9 | 13 | 2 |
| hsa-miR-106b | 35123 | 3419 | 3847 | 4164 | 4238 | 3699 | 1679 |
| hsa-miR-106b* | 1664 | 114 | 108 | 154 | 119 | 137 | 136 |
| hsa-miR-107 | 628 | 274 | 282 | 274 | 209 | 308 | 159 |
| hsa-miR-10a | 186 | 26956 | 24934 | 27899 | 28106 | 29258 | 17837 |
| hsa-miR-10a* | 0 | 115 | 112 | 129 | 148 | 136 | 123 |
| hsa-miR-10b | 7 | 40830 | 37049 | 43481 | 43238 | 44884 | 40079 |
| hsa-miR-10b* | 0 | 361 | 326 | 359 | 416 | 368 | 469 |
| hsa-miR-1178 | 0 | 0 | 0 | 0 | 0 | 0 | 0 |
| hsa-miR-1179 | 5 | 77 | 69 | 91 | 81 | 90 | 16 |
| hsa-miR-1180 | 0 | 21 | 17 | 14 | 28 | 31 | 15 |
| hsa-miR-1181 | 0 | 1 | 0 | 0 | 0 | 0 | 0 |
| hsa-miR-1182 | 0 | 0 | 0 | 0 | 0 | 0 | 0 |
| hsa-miR-1183 | 0 | 0 | 0 | 0 | 0 | 0 | 0 |
| hsa-miR-1184 | 0 | 0 | 0 | 0 | 0 | 0 | 0 |
| hsa-miR-1185 | 0 | 26 | 35 | 47 | 48 | 35 | 7 |
| hsa-miR-1193 | 0 | 0 | 0 | 0 | 0 | 0 | 0 |
| hsa-miR-1197 | 0 | 1 | 3 | 0 | 2 | 0 | 0 |
| hsa-miR-1200 | 0 | 0 | 0 | 0 | 0 | 0 | 0 |
| hsa-miR-1201 | 422 | 56 | 55 | 63 | 66 | 91 | 69 |
| hsa-miR-1202 | 0 | 0 | 0 | 0 | 0 | 0 | 0 |
| hsa-miR-1203 | 0 | 0 | 0 | 0 | 0 | 0 | 0 |
| hsa-miR-1204 | 0 | 0 | 0 | 0 | 0 | 0 | 0 |
| hsa-miR-1205 | 0 | 0 | 0 | 0 | 0 | 0 | 0 |
| hsa-miR-1206 | 0 | 0 | 0 | 0 | 0 | 0 | 0 |
| hsa-miR-1207-3p | 0 | 0 | 0 | 0 | 0 | 0 | 0 |
| hsa-miR-1207-5p | 0 | 0 | 0 | 0 | 0 | 0 | 0 |
| hsa-miR-1208 | 0 | 0 | 0 | 0 | 0 | 0 | 0 |
| hsa-miR-122 | 4 | 5808 | 5666 | 6201 | 6163 | 6375 | 81 |
| hsa-miR-122* | 0 | 57 | 56 | 78 | 85 | 66 | 2 |

TABLE 7-continued

| | Human RNA pool adaptors | | | | | | Breast |
|---|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-1224-3p | 0 | 0 | 0 | 1 | 0 | 0 | 0 |
| hsa-miR-1224-5p | 0 | 13 | 12 | 8 | 10 | 10 | 0 |
| hsa-miR-1225-3p | 0 | 1 | 0 | 0 | 0 | 0 | 0 |
| hsa-miR-1225-5p | 0 | 0 | 0 | 2 | 1 | 1 | 2 |
| hsa-miR-1226 | 6 | 1 | 2 | 2 | 6 | 2 | 1 |
| hsa-miR-1226* | 7 | 0 | 0 | 3 | 0 | 0 | 0 |
| hsa-miR-1227 | 0 | 0 | 0 | 0 | 0 | 0 | 0 |
| hsa-miR-1228 | 0 | 1 | 1 | 0 | 1 | 2 | 2 |
| hsa-miR-1228* | 0 | 0 | 1 | 1 | 1 | 0 | 1 |
| hsa-miR-1229 | 1 | 2 | 0 | 4 | 1 | 1 | 0 |
| hsa-miR-1231 | 0 | 1 | 2 | 0 | 2 | 0 | 0 |
| hsa-miR-1233 | 0 | 1 | 1 | 0 | 1 | 0 | 0 |
| hsa-miR-1234 | 1 | 1 | 0 | 0 | 0 | 1 | 0 |
| hsa-miR-1236 | 0 | 0 | 0 | 0 | 0 | 0 | 0 |
| hsa-miR-1237 | 0 | 0 | 0 | 0 | 0 | 0 | 0 |
| hsa-miR-1238 | 0 | 0 | 0 | 0 | 0 | 0 | 0 |
| hsa-miR-124 | 0 | 1249 | 1154 | 1262 | 1285 | 1408 | 2 |
| hsa-miR-124* | 0 | 5 | 1 | 6 | 4 | 5 | 0 |
| hsa-miR-1243 | 5 | 5 | 2 | 0 | 1 | 3 | 2 |
| hsa-miR-1244 | 0 | 3 | 1 | 7 | 1 | 5 | 2 |
| hsa-miR-1245 | 0 | 0 | 1 | 1 | 3 | 1 | 2 |
| hsa-miR-1246 | 49235 | 5920 | 5881 | 6452 | 6358 | 6490 | 37368 |
| hsa-miR-1247 | 0 | 92 | 92 | 112 | 120 | 93 | 46 |
| hsa-miR-1248 | 2 | 28 | 22 | 22 | 19 | 16 | 27 |
| hsa-miR-1249 | 1 | 25 | 26 | 31 | 32 | 29 | 11 |
| hsa-miR-1250 | 0 | 4 | 1 | 1 | 0 | 2 | 0 |
| hsa-miR-1251 | 0 | 110 | 82 | 133 | 128 | 137 | 0 |
| hsa-miR-1252 | 0 | 1 | 2 | 1 | 2 | 0 | 0 |
| hsa-miR-1253 | 0 | 0 | 0 | 0 | 0 | 0 | 0 |
| hsa-miR-1254 | 34 | 1 | 3 | 12 | 7 | 8 | 2 |
| hsa-miR-1255a | 46 | 6 | 12 | 11 | 11 | 5 | 4 |
| hsa-miR-1255b | 6 | 3 | 3 | 11 | 2 | 7 | 3 |
| hsa-miR-1256 | 5 | 0 | 4 | 1 | 0 | 0 | 0 |
| hsa-miR-1257 | 27 | 0 | 0 | 0 | 0 | 0 | 0 |
| hsa-miR-1258 | 0 | 2 | 3 | 1 | 4 | 1 | 2 |
| hsa-miR-1259 | 268 | 38 | 29 | 29 | 30 | 43 | 69 |
| hsa-miR-125a-3p | 0 | 76 | 63 | 69 | 62 | 59 | 46 |
| hsa-miR-125a-5p | 3 | 14695 | 14391 | 16483 | 15940 | 16054 | 8971 |
| hsa-miR-125b | 738 | 30693 | 29479 | 33392 | 32497 | 33293 | 16929 |
| hsa-miR-125b-1* | 0 | 70 | 64 | 65 | 65 | 81 | 59 |
| hsa-miR-125b-2* | 421 | 1017 | 994 | 1074 | 1037 | 1170 | 640 |
| hsa-miR-126 | 2 | 163374 | 163020 | 188443 | 191489 | 175101 | 137109 |
| hsa-miR-126* | 2 | 24037 | 23282 | 29250 | 28209 | 26553 | 25398 |
| hsa-miR-1260 | 5 | 0 | 3 | 0 | 3 | 2 | 1 |
| hsa-miR-1260b | 60 | 14 | 16 | 15 | 11 | 12 | 8 |
| hsa-miR-1261 | 0 | 0 | 0 | 0 | 0 | 0 | 0 |
| hsa-miR-1262 | 0 | 12 | 7 | 11 | 9 | 17 | 12 |
| hsa-miR-1263 | 0 | 0 | 0 | 0 | 0 | 0 | 0 |
| hsa-miR-1264 | 0 | 0 | 1 | 2 | 1 | 2 | 0 |
| hsa-miR-1265 | 0 | 3 | 0 | 0 | 0 | 0 | 0 |
| hsa-miR-1266 | 0 | 5 | 3 | 3 | 4 | 0 | 8 |
| hsa-miR-1267 | 0 | 0 | 0 | 0 | 1 | 0 | 0 |
| hsa-miR-1268 | 504 | 20 | 22 | 30 | 24 | 20 | 9 |
| hsa-miR-1269 | 0 | 14 | 15 | 13 | 14 | 13 | 0 |
| hsa-miR-1270 | 474 | 66 | 47 | 48 | 67 | 74 | 37 |
| hsa-miR-1271 | 0 | 50 | 48 | 58 | 58 | 40 | 39 |
| hsa-miR-1272 | 0 | 0 | 0 | 0 | 0 | 1 | 0 |
| hsa-miR-1273 | 0 | 0 | 0 | 0 | 0 | 0 | 0 |
| hsa-miR-1273c | 5 | 2 | 3 | 5 | 4 | 7 | 4 |
| hsa-miR-1273d | 3 | 0 | 0 | 1 | 0 | 0 | 0 |
| hsa-miR-127-3p | 3 | 1993 | 1787 | 2084 | 2026 | 2092 | 1242 |
| hsa-miR-1274a | 9 | 0 | 0 | 1 | 0 | 0 | 0 |
| hsa-miR-1274b | 40 | 64 | 61 | 70 | 72 | 49 | 23 |
| hsa-miR-1275 | 192 | 25 | 27 | 36 | 23 | 30 | 16 |
| hsa-miR-127-5p | 0 | 343 | 290 | 391 | 386 | 362 | 69 |
| hsa-miR-1276 | 23 | 1 | 0 | 0 | 2 | 1 | 0 |
| hsa-miR-1277 | 79 | 39 | 22 | 37 | 26 | 32 | 4 |
| hsa-miR-1278 | 21 | 1 | 1 | 1 | 1 | 2 | 0 |
| hsa-miR-1279 | 0 | 0 | 0 | 0 | 0 | 0 | 0 |
| hsa-miR-128 | 1231 | 2133 | 2052 | 2282 | 2117 | 2319 | 262 |
| hsa-miR-1280 | 2 | 9 | 8 | 14 | 5 | 14 | 7 |
| hsa-miR-1281 | 0 | 0 | 0 | 0 | 0 | 0 | 0 |
| hsa-miR-1282 | 0 | 0 | 0 | 0 | 0 | 0 | 0 |
| hsa-miR-1283 | 0 | 251 | 238 | 288 | 268 | 276 | 1 |

TABLE 7-continued

| | Human RNA pool | | | | | | Breast |
| | adaptors | | | | | | |
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
|---|---|---|---|---|---|---|---|
| hsa-miR-1284 | 5 | 2 | 1 | 0 | 1 | 0 | 0 |
| hsa-miR-1285 | 412 | 13 | 15 | 21 | 12 | 16 | 13 |
| hsa-miR-1286 | 0 | 0 | 0 | 0 | 1 | 0 | 0 |
| hsa-miR-1287 | 1 | 35 | 31 | 32 | 49 | 30 | 40 |
| hsa-miR-1288 | 0 | 0 | 0 | 0 | 0 | 0 | 0 |
| hsa-miR-1289 | 0 | 1 | 0 | 0 | 0 | 0 | 0 |
| hsa-miR-129* | 3 | 26 | 29 | 28 | 15 | 30 | 0 |
| hsa-miR-1290 | 3 | 0 | 0 | 0 | 1 | 0 | 1 |
| hsa-miR-1291 | 47 | 38 | 13 | 25 | 27 | 18 | 16 |
| hsa-miR-1292 | 162 | 20 | 39 | 31 | 32 | 24 | 29 |
| hsa-miR-1293 | 0 | 0 | 1 | 0 | 0 | 0 | 0 |
| hsa-miR-129-3p | 3 | 84 | 78 | 84 | 98 | 102 | 1 |
| hsa-miR-1294 | 4 | 2 | 1 | 2 | 7 | 3 | 2 |
| hsa-miR-1295 | 0 | 1 | 3 | 1 | 2 | 2 | 6 |
| hsa-miR-129-5p | 4 | 280 | 267 | 306 | 326 | 311 | 3 |
| hsa-miR-1296 | 10 | 50 | 52 | 53 | 65 | 49 | 47 |
| hsa-miR-1297 | 0 | 0 | 0 | 0 | 0 | 0 | 0 |
| hsa-miR-1298 | 0 | 15 | 13 | 16 | 14 | 18 | 0 |
| hsa-miR-1299 | 15 | 51 | 61 | 45 | 63 | 58 | 66 |
| hsa-miR-1301 | 1 | 49 | 45 | 48 | 50 | 50 | 14 |
| hsa-miR-1302 | 0 | 1 | 0 | 0 | 0 | 0 | 0 |
| hsa-miR-1303 | 27 | 7 | 5 | 7 | 8 | 17 | 7 |
| hsa-miR-1304 | 7 | 3 | 1 | 3 | 2 | 3 | 0 |
| hsa-miR-1305 | 0 | 2 | 8 | 6 | 7 | 5 | 5 |
| hsa-miR-1306 | 1 | 0 | 3 | 2 | 3 | 1 | 5 |
| hsa-miR-1307 | 1860 | 328 | 292 | 362 | 324 | 337 | 196 |
| hsa-miR-1308 | 722 | 471 | 506 | 521 | 567 | 519 | 206 |
| hsa-miR-130a | 4 | 2674 | 2388 | 2934 | 2721 | 2777 | 2772 |
| hsa-miR-130a* | 0 | 5 | 2 | 6 | 8 | 6 | 13 |
| hsa-miR-130b | 3376 | 456 | 434 | 625 | 526 | 455 | 217 |
| hsa-miR-130b* | 81 | 85 | 63 | 66 | 63 | 72 | 21 |
| hsa-miR-132 | 77 | 750 | 687 | 834 | 904 | 797 | 686 |
| hsa-miR-132* | 6 | 125 | 110 | 117 | 116 | 119 | 57 |
| hsa-miR-1321 | 0 | 0 | 0 | 0 | 0 | 1 | 0 |
| hsa-miR-1322 | 4 | 1 | 2 | 0 | 0 | 2 | 0 |
| hsa-miR-1323 | 0 | 3503 | 3317 | 2994 | 2327 | 3903 | 8 |
| hsa-miR-1324 | 0 | 0 | 0 | 0 | 0 | 0 | 0 |
| hsa-miR-133a | 2 | 18167 | 18669 | 22360 | 22448 | 19771 | 51 |
| hsa-miR-133b | 0 | 556 | 566 | 637 | 624 | 553 | 2 |
| hsa-miR-134 | 0 | 172 | 171 | 185 | 212 | 192 | 200 |
| hsa-miR-135a | 1 | 9461 | 8663 | 9893 | 7606 | 10424 | 105 |
| hsa-miR-135a* | 0 | 6 | 6 | 4 | 8 | 9 | 0 |
| hsa-miR-135b | 0 | 2934 | 2829 | 3189 | 2875 | 3219 | 357 |
| hsa-miR-135b* | 0 | 20 | 11 | 18 | 17 | 19 | 7 |
| hsa-miR-136 | 0 | 2340 | 1609 | 1993 | 1920 | 2381 | 500 |
| hsa-miR-136* | 1 | 413 | 380 | 489 | 489 | 467 | 170 |
| hsa-miR-137 | 0 | 509 | 472 | 442 | 444 | 548 | 7 |
| hsa-miR-138 | 3027 | 968 | 858 | 1165 | 1119 | 984 | 67 |
| hsa-miR-138-1* | 58 | 27 | 26 | 26 | 27 | 27 | 8 |
| hsa-miR-138-2* | 0 | 8 | 4 | 6 | 5 | 4 | 0 |
| hsa-miR-139-3p | 9 | 125 | 130 | 105 | 116 | 131 | 163 |
| hsa-miR-139-5p | 11 | 1451 | 1370 | 1583 | 1571 | 1574 | 1683 |
| hsa-miR-140-3p | 67006 | 37936 | 34949 | 36311 | 36598 | 41136 | 16014 |
| hsa-miR-140-5p | 3672 | 6850 | 6579 | 8128 | 7884 | 7500 | 5245 |
| hsa-miR-141 | 79 | 6530 | 6644 | 6908 | 7685 | 7532 | 3759 |
| hsa-miR-141* | 0 | 155 | 128 | 159 | 131 | 134 | 152 |
| hsa-miR-142-3p | 169524 | 71892 | 68818 | 82272 | 79112 | 77431 | 8578 |
| hsa-miR-142-5p | 16201 | 2014 | 1877 | 2148 | 2101 | 2323 | 882 |
| hsa-miR-143 | 17640 | 1884521 | 1792761 | 2010306 | 2107243 | 2088207 | 1074889 |
| hsa-miR-143* | 11 | 14298 | 14952 | 19113 | 18944 | 15393 | 4904 |
| hsa-miR-144 | 0 | 1335 | 1046 | 1285 | 1271 | 1455 | 132 |
| hsa-miR-144* | 13 | 7752 | 7376 | 8357 | 8770 | 8522 | 3235 |
| hsa-miR-145 | 40 | 64408 | 62487 | 79740 | 74320 | 68219 | 26847 |
| hsa-miR-145* | 3 | 2495 | 2415 | 2993 | 2747 | 2567 | 1465 |
| hsa-miR-1468 | 1 | 4 | 5 | 4 | 8 | 7 | 1 |
| hsa-miR-1469 | 0 | 0 | 0 | 0 | 0 | 0 | 0 |
| hsa-miR-146a | 45680 | 8759 | 8469 | 9841 | 9877 | 9557 | 9883 |
| hsa-miR-146a* | 0 | 2 | 0 | 4 | 1 | 3 | 4 |
| hsa-miR-146b-3p | 40 | 20 | 10 | 23 | 25 | 23 | 46 |
| hsa-miR-146b-5p | 51686 | 64507 | 64864 | 73443 | 75492 | 70909 | 105601 |
| hsa-miR-147 | 0 | 0 | 0 | 0 | 0 | 0 | 0 |
| hsa-miR-1470 | 0 | 0 | 0 | 0 | 0 | 0 | 0 |
| hsa-miR-1471 | 0 | 0 | 0 | 0 | 0 | 0 | 0 |
| hsa-miR-147b | 0 | 5 | 8 | 9 | 7 | 4 | 13 |

TABLE 7-continued

| | Human RNA pool adaptors | | | | | | Breast |
|---|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-148a | 167654 | 83936 | 69915 | 67362 | 59455 | 92561 | 55496 |
| hsa-miR-148a* | 2741 | 231 | 173 | 236 | 232 | 238 | 257 |
| hsa-miR-148b | 18296 | 12418 | 10163 | 9757 | 8603 | 13625 | 4727 |
| hsa-miR-148b* | 2605 | 303 | 339 | 352 | 366 | 365 | 204 |
| hsa-miR-149 | 22 | 198 | 187 | 269 | 258 | 224 | 126 |
| hsa-miR-149* | 0 | 2 | 2 | 1 | 1 | 4 | 2 |
| hsa-miR-150 | 1 | 2028 | 1981 | 2312 | 2285 | 2182 | 1767 |
| hsa-miR-150* | 0 | 17 | 26 | 37 | 30 | 19 | 6 |
| hsa-miR-151-3p | 4140 | 9265 | 8272 | 9478 | 9542 | 9887 | 6249 |
| hsa-miR-151-5p | 1069 | 9893 | 9391 | 10906 | 10349 | 10836 | 6486 |
| hsa-miR-152 | 881 | 12737 | 10667 | 10744 | 9523 | 13596 | 9459 |
| hsa-miR-153 | 5 | 314 | 247 | 325 | 302 | 316 | 54 |
| hsa-miR-1537 | 0 | 3 | 1 | 2 | 3 | 3 | 0 |
| hsa-miR-1538 | 0 | 1 | 1 | 0 | 0 | 0 | 0 |
| hsa-miR-1539 | 0 | 0 | 0 | 0 | 0 | 0 | 0 |
| hsa-miR-154 | 0 | 65 | 59 | 72 | 72 | 93 | 24 |
| hsa-miR-154* | 0 | 32 | 27 | 17 | 28 | 20 | 4 |
| hsa-miR-155 | 118345 | 3723 | 3704 | 4428 | 4788 | 4169 | 2397 |
| hsa-miR-155* | 477 | 0 | 1 | 1 | 2 | 0 | 0 |
| hsa-miR-15a | 11248 | 2927 | 2588 | 3145 | 3253 | 2998 | 1562 |
| hsa-miR-15a* | 8 | 3 | 3 | 4 | 1 | 6 | 2 |
| hsa-miR-15b | 4272 | 1346 | 1127 | 1151 | 1156 | 1456 | 1012 |
| hsa-miR-15b* | 712 | 92 | 78 | 100 | 95 | 101 | 50 |
| hsa-miR-16 | 25236 | 33304 | 35260 | 36274 | 35048 | 35434 | 22850 |
| hsa-miR-16-1* | 242 | 6 | 12 | 9 | 4 | 6 | 2 |
| hsa-miR-16-2* | 277 | 81 | 97 | 115 | 90 | 77 | 92 |
| hsa-miR-17 | 75571 | 8032 | 7314 | 9397 | 9426 | 8462 | 3575 |
| hsa-miR-17* | 7638 | 396 | 347 | 387 | 360 | 469 | 69 |
| hsa-miR-181a | 14796 | 21358 | 19352 | 24301 | 24133 | 24053 | 7752 |
| hsa-miR-181a* | 977 | 244 | 223 | 282 | 287 | 246 | 53 |
| hsa-miR-181a-2* | 4 | 267 | 221 | 301 | 249 | 267 | 96 |
| hsa-miR-181b | 3623 | 2995 | 2745 | 3337 | 3228 | 3420 | 1302 |
| hsa-miR-181c | 15 | 594 | 605 | 682 | 662 | 698 | 314 |
| hsa-miR-181c* | 4 | 64 | 78 | 75 | 83 | 95 | 45 |
| hsa-miR-181d | 16 | 333 | 312 | 372 | 358 | 373 | 231 |
| hsa-miR-182 | 17542 | 4447 | 3961 | 4784 | 4611 | 4786 | 20534 |
| hsa-miR-182* | 0 | 3 | 0 | 0 | 0 | 0 | 1 |
| hsa-miR-1825 | 0 | 0 | 0 | 0 | 0 | 0 | 0 |
| hsa-miR-1826 | 201 | 209 | 183 | 222 | 226 | 236 | 145 |
| hsa-miR-1827 | 0 | 0 | 0 | 0 | 1 | 0 | 0 |
| hsa-miR-183 | 4237 | 1068 | 920 | 1093 | 972 | 1165 | 3294 |
| hsa-miR-183* | 48 | 3 | 2 | 3 | 4 | 1 | 8 |
| hsa-miR-184 | 178 | 266 | 245 | 274 | 292 | 312 | 47 |
| hsa-miR-185 | 1420 | 917 | 965 | 1062 | 1034 | 1015 | 640 |
| hsa-miR-185* | 21 | 15 | 14 | 11 | 8 | 17 | 8 |
| hsa-miR-186 | 23895 | 10864 | 11534 | 15131 | 14516 | 11876 | 9468 |
| hsa-miR-186* | 242 | 18 | 13 | 13 | 12 | 18 | 7 |
| hsa-miR-187 | 0 | 61 | 66 | 77 | 62 | 76 | 24 |
| hsa-miR-187* | 0 | 6 | 4 | 9 | 4 | 4 | 0 |
| hsa-miR-188-3p | 0 | 5 | 4 | 4 | 1 | 3 | 5 |
| hsa-miR-188-5p | 0 | 66 | 48 | 61 | 48 | 71 | 46 |
| hsa-miR-18a | 9458 | 450 | 481 | 506 | 575 | 498 | 132 |
| hsa-miR-18a* | 105 | 16 | 15 | 22 | 10 | 8 | 14 |
| hsa-miR-18b | 14 | 17 | 10 | 12 | 12 | 21 | 4 |
| hsa-miR-18b* | 0 | 3 | 2 | 1 | 2 | 0 | 0 |
| hsa-miR-190 | 682 | 1085 | 1022 | 1248 | 1277 | 1256 | 529 |
| hsa-miR-1908 | 0 | 1 | 0 | 0 | 1 | 4 | 0 |
| hsa-miR-1909 | 0 | 0 | 0 | 0 | 0 | 0 | 0 |
| hsa-miR-1909* | 0 | 0 | 0 | 0 | 0 | 0 | 0 |
| hsa-miR-190b | 3 | 17 | 16 | 28 | 30 | 22 | 258 |
| hsa-miR-191 | 49626 | 21938 | 20938 | 23858 | 21723 | 24104 | 14960 |
| hsa-miR-191* | 85 | 7 | 9 | 7 | 8 | 10 | 3 |
| hsa-miR-1910 | 0 | 0 | 0 | 0 | 1 | 0 | 0 |
| hsa-miR-1911 | 0 | 12 | 11 | 3 | 13 | 8 | 0 |
| hsa-miR-1911* | 0 | 0 | 0 | 0 | 0 | 0 | 0 |
| hsa-miR-1912 | 0 | 3 | 1 | 5 | 3 | 3 | 0 |
| hsa-miR-1913 | 0 | 0 | 0 | 0 | 1 | 0 | 0 |
| hsa-miR-1914 | 0 | 0 | 0 | 0 | 0 | 0 | 1 |
| hsa-miR-1914* | 0 | 0 | 1 | 0 | 0 | 0 | 0 |
| hsa-miR-1915 | 0 | 0 | 0 | 0 | 0 | 1 | 0 |
| hsa-miR-1915* | 0 | 0 | 0 | 0 | 0 | 0 | 0 |
| hsa-miR-192 | 12660 | 67252 | 64208 | 78702 | 77501 | 72613 | 1512 |
| hsa-miR-192* | 13 | 108 | 96 | 114 | 116 | 86 | 9 |
| hsa-miR-193a-3p | 2 | 321 | 195 | 260 | 226 | 300 | 597 |

TABLE 7-continued

|  | Human RNA pool adaptors | | | | | | Breast |
|---|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-193a-5p | 0 | 274 | 240 | 270 | 305 | 250 | 1038 |
| hsa-miR-193b | 3731 | 1819 | 1714 | 2035 | 1909 | 1997 | 3930 |
| hsa-miR-193b* | 387 | 53 | 61 | 65 | 56 | 69 | 131 |
| hsa-miR-194 | 1023 | 29917 | 30929 | 37348 | 37266 | 32599 | 483 |
| hsa-miR-194* | 23 | 46 | 41 | 43 | 42 | 49 | 1 |
| hsa-miR-195 | 1 | 5404 | 5286 | 4950 | 4646 | 5711 | 8702 |
| hsa-miR-195* | 0 | 24 | 26 | 30 | 34 | 35 | 41 |
| hsa-miR-196a | 59 | 559 | 574 | 687 | 745 | 676 | 623 |
| hsa-miR-196a* | 3 | 1 | 0 | 3 | 2 | 1 | 1 |
| hsa-miR-196b | 0 | 1600 | 1451 | 1723 | 1821 | 1707 | 742 |
| hsa-miR-196b* | 0 | 4 | 2 | 3 | 0 | 5 | 2 |
| hsa-miR-197 | 322 | 1102 | 1084 | 1283 | 1209 | 1109 | 865 |
| hsa-miR-1972 | 0 | 0 | 0 | 0 | 0 | 0 | 0 |
| hsa-miR-1973 | 9 | 9 | 8 | 5 | 6 | 10 | 4 |
| hsa-miR-1975 | 1004 | 3292 | 3615 | 4209 | 4391 | 3345 | 9392 |
| hsa-miR-1976 | 10 | 10 | 4 | 12 | 4 | 6 | 4 |
| hsa-miR-1979 | 1720 | 1998 | 1856 | 2198 | 2246 | 2083 | 14700 |
| hsa-miR-198 | 0 | 0 | 0 | 0 | 0 | 0 | 1 |
| hsa-miR-199a-3p | 5 | 20978 | 20327 | 25304 | 24599 | 23143 | 29779 |
| hsa-miR-199a-5p | 1 | 3977 | 3908 | 4604 | 4598 | 4225 | 5084 |
| hsa-miR-199b-3p | 5 | 20978 | 20327 | 25304 | 24599 | 23143 | 29779 |
| hsa-miR-199b-5p | 0 | 957 | 864 | 1106 | 1119 | 1025 | 2982 |
| hsa-miR-19a | 5598 | 2533 | 2848 | 3908 | 3726 | 2702 | 903 |
| hsa-miR-19a* | 18 | 0 | 1 | 0 | 1 | 1 | 0 |
| hsa-miR-19b | 18432 | 9896 | 10962 | 14056 | 13647 | 10888 | 9189 |
| hsa-miR-19b-1* | 256 | 25 | 22 | 23 | 20 | 21 | 13 |
| hsa-miR-19b-2* | 0 | 0 | 0 | 0 | 0 | 0 | 0 |
| hsa-miR-200a | 5 | 2454 | 2278 | 2445 | 2540 | 2705 | 1661 |
| hsa-miR-200a* | 0 | 44 | 53 | 54 | 49 | 71 | 47 |
| hsa-miR-200b | 2 | 3797 | 3888 | 4427 | 4654 | 4284 | 5020 |
| hsa-miR-200b* | 0 | 410 | 390 | 415 | 381 | 413 | 423 |
| hsa-miR-200c | 155 | 30724 | 29255 | 31830 | 33480 | 34310 | 43316 |
| hsa-miR-200c* | 2 | 7 | 11 | 11 | 12 | 11 | 6 |
| hsa-miR-202 | 0 | 366 | 321 | 280 | 191 | 397 | 1 |
| hsa-miR-202* | 1 | 7203 | 6848 | 8579 | 8374 | 8087 | 86 |
| hsa-miR-203 | 0 | 4340 | 3971 | 4752 | 4447 | 4863 | 1179 |
| hsa-miR-204 | 0 | 689 | 695 | 838 | 784 | 810 | 67 |
| hsa-miR-205 | 0 | 5042 | 4656 | 5518 | 5108 | 5408 | 55620 |
| hsa-miR-205* | 0 | 2 | 1 | 3 | 1 | 0 | 4 |
| hsa-miR-2052 | 0 | 0 | 0 | 0 | 0 | 0 | 0 |
| hsa-miR-2053 | 0 | 0 | 0 | 0 | 0 | 0 | 0 |
| hsa-miR-2054 | 0 | 0 | 0 | 0 | 0 | 0 | 0 |
| hsa-miR-206 | 0 | 13453 | 13591 | 15087 | 16300 | 15006 | 4 |
| hsa-miR-208a | 0 | 64 | 34 | 54 | 43 | 66 | 0 |
| hsa-miR-208b | 0 | 322 | 319 | 343 | 304 | 354 | 0 |
| hsa-miR-20a | 138720 | 9808 | 9528 | 10260 | 10813 | 10890 | 5182 |
| hsa-miR-20a* | 454 | 419 | 476 | 560 | 521 | 420 | 168 |
| hsa-miR-20b | 2 | 1344 | 1204 | 1591 | 1628 | 1459 | 138 |
| hsa-miR-20b* | 0 | 20 | 13 | 18 | 20 | 23 | 3 |
| hsa-miR-21 | 1852326 | 331847 | 313309 | 353783 | 377299 | 368479 | 300625 |
| hsa-miR-21* | 2992 | 117 | 104 | 123 | 126 | 122 | 102 |
| hsa-miR-210 | 5008 | 992 | 971 | 1242 | 1326 | 974 | 254 |
| hsa-miR-211 | 0 | 2 | 1 | 4 | 0 | 3 | 2 |
| hsa-miR-2110 | 29 | 93 | 89 | 60 | 36 | 105 | 53 |
| hsa-miR-2113 | 0 | 0 | 0 | 0 | 0 | 0 | 0 |
| hsa-miR-2114 | 0 | 5 | 7 | 6 | 5 | 8 | 1 |
| hsa-miR-2114* | 0 | 0 | 1 | 1 | 0 | 0 | 0 |
| hsa-miR-2115 | 0 | 3 | 2 | 1 | 3 | 2 | 26 |
| hsa-miR-2115* | 0 | 1 | 7 | 2 | 1 | 2 | 40 |
| hsa-miR-2116 | 1 | 3 | 4 | 4 | 5 | 0 | 1 |
| hsa-miR-2116* | 0 | 2 | 0 | 3 | 3 | 3 | 3 |
| hsa-miR-2117 | 0 | 0 | 0 | 0 | 0 | 0 | 0 |
| hsa-miR-212 | 0 | 25 | 23 | 25 | 28 | 24 | 19 |
| hsa-miR-214 | 0 | 916 | 830 | 776 | 685 | 984 | 1207 |
| hsa-miR-214* | 0 | 167 | 154 | 183 | 207 | 209 | 129 |
| hsa-miR-215 | 142 | 51160 | 49148 | 56830 | 57666 | 56128 | 414 |
| hsa-miR-216a | 2 | 20 | 18 | 25 | 20 | 18 | 7 |
| hsa-miR-216b | 0 | 70 | 63 | 76 | 87 | 74 | 12 |
| hsa-miR-217 | 7 | 62 | 47 | 61 | 54 | 66 | 20 |
| hsa-miR-218 | 1 | 2040 | 2073 | 2559 | 2571 | 2186 | 1055 |
| hsa-miR-218-1* | 0 | 56 | 48 | 63 | 49 | 58 | 58 |
| hsa-miR-218-2* | 0 | 0 | 3 | 2 | 1 | 4 | 0 |
| hsa-miR-219-1-3p | 71 | 2 | 2 | 1 | 2 | 6 | 3 |

TABLE 7-continued

| RNA miRNA | Human RNA pool adaptors | | | | | | Breast |
|---|---|---|---|---|---|---|---|
| | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-219-2-3p | 0 | 902 | 1342 | 1709 | 1858 | 2121 | 2 |
| hsa-miR-219-5p | 30 | 44 | 42 | 53 | 39 | 41 | 1 |
| hsa-miR-22 | 926 | 12597 | 11782 | 13008 | 13488 | 13549 | 11463 |
| hsa-miR-22* | 53 | 866 | 967 | 1293 | 1130 | 948 | 1006 |
| hsa-miR-220a | 0 | 0 | 0 | 0 | 0 | 0 | 0 |
| hsa-miR-220b | 0 | 0 | 0 | 0 | 0 | 0 | 0 |
| hsa-miR-220c | 0 | 0 | 0 | 0 | 0 | 0 | 0 |
| hsa-miR-221 | 285 | 3056 | 3079 | 3686 | 3758 | 3422 | 2113 |
| hsa-miR-221* | 391 | 1229 | 999 | 1015 | 861 | 1312 | 389 |
| hsa-miR-222 | 213 | 7470 | 7604 | 9085 | 8803 | 8291 | 5395 |
| hsa-miR-222* | 75 | 38 | 25 | 39 | 23 | 33 | 10 |
| hsa-miR-223 | 3 | 2838 | 2663 | 3045 | 3179 | 3067 | 1895 |
| hsa-miR-223* | 1 | 94 | 117 | 201 | 183 | 101 | 51 |
| hsa-miR-224 | 0 | 587 | 531 | 684 | 703 | 650 | 997 |
| hsa-miR-224* | 0 | 28 | 30 | 30 | 26 | 34 | 77 |
| hsa-miR-2276 | 22 | 6 | 4 | 6 | 4 | 8 | 3 |
| hsa-miR-2277 | 1 | 4 | 0 | 6 | 1 | 4 | 2 |
| hsa-miR-2278 | 0 | 0 | 0 | 1 | 2 | 0 | 4 |
| hsa-miR-2355 | 0 | 5 | 8 | 9 | 4 | 3 | 7 |
| hsa-miR-23a | 360 | 15888 | 14598 | 17234 | 16789 | 17131 | 21956 |
| hsa-miR-23a* | 3 | 4 | 3 | 0 | 0 | 1 | 3 |
| hsa-miR-23b | 474 | 14755 | 13404 | 15889 | 15851 | 15682 | 5726 |
| hsa-miR-23b* | 6 | 21 | 18 | 17 | 13 | 16 | 6 |
| hsa-miR-24 | 1815 | 116792 | 122743 | 140600 | 135084 | 126140 | 67259 |
| hsa-miR-24-1* | 8 | 276 | 284 | 347 | 304 | 343 | 56 |
| hsa-miR-24-2* | 14 | 584 | 523 | 594 | 525 | 558 | 272 |
| hsa-miR-25 | 7496 | 1904 | 1720 | 1980 | 1914 | 2048 | 1898 |
| hsa-miR-25* | 61 | 30 | 29 | 23 | 10 | 38 | 11 |
| hsa-miR-26a | 23823 | 139238 | 120963 | 131441 | 135641 | 156484 | 139950 |
| hsa-miR-26a-1* | 0 | 4 | 7 | 3 | 1 | 6 | 4 |
| hsa-miR-26a-2* | 58 | 68 | 51 | 77 | 70 | 59 | 63 |
| hsa-miR-26b | 11315 | 37731 | 28997 | 31628 | 32208 | 42694 | 29712 |
| hsa-miR-26b* | 43 | 50 | 54 | 56 | 63 | 61 | 59 |
| hsa-miR-27a | 362 | 19157 | 19019 | 21101 | 22219 | 21482 | 21448 |
| hsa-miR-27a* | 20 | 43 | 42 | 73 | 61 | 49 | 36 |
| hsa-miR-27b | 2465 | 47617 | 43110 | 45439 | 47218 | 52830 | 16131 |
| hsa-miR-27b* | 135 | 633 | 790 | 963 | 965 | 725 | 207 |
| hsa-miR-28-3p | 1396 | 3372 | 2921 | 3435 | 3485 | 3521 | 2162 |
| hsa-miR-28-5p | 1019 | 3040 | 2861 | 3393 | 3391 | 3514 | 3027 |
| hsa-miR-2861 | 0 | 0 | 0 | 0 | 0 | 0 | 0 |
| hsa-miR-2909 | 0 | 0 | 0 | 0 | 0 | 0 | 0 |
| hsa-miR-296-3p | 50 | 4 | 3 | 4 | 5 | 4 | 10 |
| hsa-miR-296-5p | 79 | 32 | 33 | 46 | 46 | 30 | 57 |
| hsa-miR-297 | 0 | 0 | 0 | 0 | 0 | 0 | 0 |
| hsa-miR-298 | 0 | 0 | 0 | 0 | 0 | 0 | 0 |
| hsa-miR-299-3p | 0 | 33 | 31 | 32 | 43 | 40 | 18 |
| hsa-miR-299-5p | 0 | 72 | 78 | 91 | 88 | 71 | 34 |
| hsa-miR-29a | 40124 | 61875 | 60909 | 79815 | 80527 | 67864 | 31795 |
| hsa-miR-29a* | 991 | 294 | 301 | 347 | 369 | 332 | 167 |
| hsa-miR-29b | 14193 | 26166 | 18024 | 24954 | 24981 | 29084 | 5148 |
| hsa-miR-29b-1* | 120 | 16 | 18 | 28 | 32 | 19 | 9 |
| hsa-miR-29b-2* | 147 | 146 | 115 | 155 | 155 | 131 | 87 |
| hsa-miR-29c | 1880 | 3927 | 3550 | 4318 | 4137 | 4173 | 3491 |
| hsa-miR-29c* | 162 | 359 | 397 | 441 | 421 | 380 | 317 |
| hsa-miR-300 | 0 | 0 | 0 | 0 | 0 | 0 | 0 |
| hsa-miR-301a | 421 | 98 | 82 | 92 | 93 | 120 | 10 |
| hsa-miR-301b | 169 | 14 | 13 | 8 | 16 | 5 | 1 |
| hsa-miR-302a | 0 | 2 | 3 | 3 | 2 | 10 | 0 |
| hsa-miR-302a* | 0 | 12 | 5 | 13 | 10 | 12 | 0 |
| hsa-miR-302b | 0 | 4 | 6 | 14 | 9 | 9 | 0 |
| hsa-miR-302b* | 0 | 0 | 0 | 0 | 0 | 2 | 0 |
| hsa-miR-302c | 0 | 2 | 2 | 1 | 1 | 1 | 0 |
| hsa-miR-302c* | 0 | 0 | 0 | 0 | 0 | 0 | 0 |
| hsa-miR-302d | 0 | 3 | 1 | 1 | 1 | 4 | 0 |
| hsa-miR-302d* | 0 | 0 | 0 | 0 | 0 | 0 | 0 |
| hsa-miR-302e | 0 | 0 | 0 | 0 | 0 | 0 | 0 |
| hsa-miR-302f | 0 | 0 | 0 | 0 | 0 | 0 | 0 |
| hsa-miR-3065-3p | 1 | 112 | 102 | 122 | 100 | 116 | 35 |
| hsa-miR-3065-5p | 0 | 114 | 114 | 122 | 119 | 110 | 22 |
| hsa-miR-3074 | 1 | 1 | 0 | 1 | 1 | 2 | 1 |
| hsa-miR-30a | 425 | 134091 | 121854 | 147246 | 139908 | 146572 | 158595 |
| hsa-miR-30a* | 4 | 5542 | 4869 | 5972 | 5456 | 5900 | 8890 |
| hsa-miR-30b | 7820 | 25303 | 23222 | 30378 | 31188 | 28066 | 16765 |

TABLE 7-continued

|  | Human RNA pool adaptors | | | | | | Breast |
|---|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-30b* | 87 | 46 | 53 | 77 | 76 | 50 | 39 |
| hsa-miR-30c | 13867 | 33356 | 32048 | 37747 | 37655 | 35877 | 24196 |
| hsa-miR-30c-1* | 54 | 28 | 31 | 50 | 51 | 25 | 26 |
| hsa-miR-30c-2* | 0 | 367 | 324 | 335 | 330 | 411 | 491 |
| hsa-miR-30d | 235117 | 66258 | 63436 | 72267 | 71041 | 71729 | 54966 |
| hsa-miR-30d* | 450 | 83 | 84 | 90 | 88 | 83 | 74 |
| hsa-miR-30e | 238220 | 47135 | 46880 | 52861 | 55314 | 52193 | 14558 |
| hsa-miR-30e* | 11783 | 6097 | 5381 | 6546 | 6164 | 6665 | 3187 |
| hsa-miR-31 | 0 | 776 | 768 | 823 | 692 | 794 | 654 |
| hsa-miR-31* | 0 | 22 | 31 | 21 | 26 | 31 | 40 |
| hsa-miR-3115 | 2 | 3 | 1 | 2 | 1 | 2 | 2 |
| hsa-miR-3116 | 0 | 0 | 1 | 0 | 2 | 0 | 0 |
| hsa-miR-3117 | 0 | 10 | 7 | 8 | 6 | 6 | 0 |
| hsa-miR-3118 | 0 | 0 | 0 | 0 | 0 | 0 | 0 |
| hsa-miR-3119 | 0 | 0 | 0 | 0 | 0 | 0 | 0 |
| hsa-miR-3120 | 1 | 0 | 0 | 1 | 0 | 2 | 0 |
| hsa-miR-3121 | 4 | 1 | 0 | 0 | 0 | 1 | 1 |
| hsa-miR-3122 | 2 | 0 | 0 | 0 | 0 | 0 | 1 |
| hsa-miR-3123 | 0 | 0 | 0 | 0 | 0 | 0 | 0 |
| hsa-miR-3124 | 0 | 3 | 3 | 1 | 3 | 3 | 2 |
| hsa-miR-3125 | 0 | 2 | 3 | 0 | 1 | 4 | 1 |
| hsa-miR-3126-3p | 0 | 0 | 0 | 2 | 0 | 0 | 0 |
| hsa-miR-3126-5p | 0 | 1 | 0 | 0 | 0 | 3 | 0 |
| hsa-miR-3127 | 15 | 5 | 1 | 2 | 4 | 0 | 1 |
| hsa-miR-3128 | 13 | 0 | 4 | 0 | 0 | 4 | 0 |
| hsa-miR-3129 | 0 | 5 | 3 | 8 | 5 | 7 | 14 |
| hsa-miR-3130-3p | 0 | 0 | 0 | 0 | 0 | 0 | 0 |
| hsa-miR-3130-5p | 7 | 2 | 1 | 0 | 1 | 1 | 1 |
| hsa-miR-3131 | 0 | 0 | 0 | 0 | 0 | 1 | 0 |
| hsa-miR-3132 | 0 | 1 | 0 | 0 | 1 | 0 | 0 |
| hsa-miR-3133 | 5 | 1 | 1 | 2 | 1 | 0 | 2 |
| hsa-miR-3134 | 3 | 1 | 1 | 1 | 0 | 3 | 1 |
| hsa-miR-3135 | 0 | 0 | 0 | 0 | 0 | 0 | 0 |
| hsa-miR-3136 | 8 | 2 | 2 | 0 | 0 | 0 | 0 |
| hsa-miR-3137 | 0 | 0 | 0 | 0 | 0 | 0 | 0 |
| hsa-miR-3138 | 1 | 5 | 3 | 4 | 1 | 0 | 2 |
| hsa-miR-3139 | 1 | 1 | 0 | 0 | 3 | 0 | 0 |
| hsa-miR-3140 | 6 | 2 | 1 | 0 | 3 | 0 | 1 |
| hsa-miR-3141 | 1 | 1 | 1 | 1 | 0 | 0 | 0 |
| hsa-miR-3142 | 0 | 0 | 0 | 0 | 0 | 0 | 0 |
| hsa-miR-3143 | 1 | 1 | 0 | 1 | 1 | 0 | 0 |
| hsa-miR-3144-3p | 0 | 0 | 0 | 1 | 0 | 1 | 1 |
| hsa-miR-3144-5p | 0 | 0 | 0 | 0 | 0 | 2 | 1 |
| hsa-miR-3145 | 0 | 0 | 0 | 0 | 3 | 2 | 0 |
| hsa-miR-3146 | 10 | 3 | 1 | 2 | 2 | 6 | 1 |
| hsa-miR-3147 | 0 | 0 | 0 | 0 | 0 | 0 | 0 |
| hsa-miR-3148 | 0 | 0 | 0 | 0 | 0 | 1 | 0 |
| hsa-miR-3149 | 0 | 1 | 2 | 1 | 1 | 2 | 0 |
| hsa-miR-3150 | 0 | 1 | 0 | 0 | 0 | 0 | 0 |
| hsa-miR-3151 | 0 | 0 | 0 | 0 | 0 | 0 | 0 |
| hsa-miR-3152 | 0 | 0 | 0 | 0 | 0 | 0 | 0 |
| hsa-miR-3153 | 0 | 0 | 0 | 0 | 0 | 0 | 0 |
| hsa-miR-3154 | 0 | 7 | 9 | 13 | 5 | 13 | 2 |
| hsa-miR-3155 | 1 | 0 | 0 | 1 | 0 | 0 | 0 |
| hsa-miR-3156 | 0 | 0 | 0 | 0 | 0 | 1 | 0 |
| hsa-miR-3157 | 1 | 1 | 1 | 1 | 1 | 2 | 2 |
| hsa-miR-3158 | 135 | 3 | 6 | 7 | 10 | 8 | 1 |
| hsa-miR-3159 | 0 | 0 | 0 | 0 | 0 | 0 | 0 |
| hsa-miR-3160 | 0 | 0 | 1 | 0 | 0 | 0 | 0 |
| hsa-miR-3161 | 6 | 0 | 1 | 1 | 0 | 3 | 0 |
| hsa-miR-3162 | 0 | 1 | 0 | 0 | 0 | 0 | 0 |
| hsa-miR-3163 | 0 | 1 | 1 | 1 | 1 | 1 | 1 |
| hsa-miR-3164 | 11 | 3 | 3 | 3 | 7 | 6 | 2 |
| hsa-miR-3165 | 0 | 0 | 0 | 0 | 0 | 0 | 0 |
| hsa-miR-3166 | 0 | 0 | 0 | 0 | 0 | 0 | 1 |
| hsa-miR-3167 | 0 | 2 | 0 | 1 | 1 | 0 | 0 |
| hsa-miR-3168 | 0 | 0 | 0 | 0 | 0 | 0 | 2 |
| hsa-miR-3169 | 0 | 0 | 0 | 0 | 0 | 0 | 0 |
| hsa-miR-3170 | 0 | 0 | 1 | 0 | 0 | 0 | 0 |
| hsa-miR-3171 | 0 | 0 | 1 | 0 | 0 | 1 | 0 |
| hsa-miR-3172 | 22 | 49 | 37 | 44 | 37 | 47 | 188 |
| hsa-miR-3173 | 2 | 0 | 0 | 0 | 0 | 0 | 1 |
| hsa-miR-3174 | 10 | 1 | 1 | 0 | 0 | 0 | 1 |
| hsa-miR-3175 | 0 | 0 | 0 | 0 | 2 | 0 | 1 |

TABLE 7-continued

| | Human RNA pool adaptors | | | | | | Breast |
|---|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-3176 | 14 | 2 | 1 | 5 | 7 | 4 | 1 |
| hsa-miR-3177 | 9 | 3 | 5 | 5 | 4 | 5 | 0 |
| hsa-miR-3178 | 0 | 0 | 0 | 0 | 0 | 0 | 0 |
| hsa-miR-3179 | 3 | 2 | 0 | 0 | 0 | 1 | 1 |
| hsa-miR-3180-3p | 7 | 1 | 0 | 2 | 0 | 0 | 1 |
| hsa-miR-3180-5p | 0 | 0 | 1 | 0 | 2 | 0 | 0 |
| hsa-miR-3181 | 2 | 0 | 0 | 1 | 0 | 1 | 0 |
| hsa-miR-3182 | 0 | 0 | 0 | 0 | 0 | 0 | 0 |
| hsa-miR-3183 | 0 | 0 | 0 | 0 | 0 | 0 | 0 |
| hsa-miR-3184 | 2 | 0 | 0 | 0 | 0 | 0 | 0 |
| hsa-miR-3185 | 0 | 0 | 0 | 0 | 0 | 0 | 0 |
| hsa-miR-3186-3p | 0 | 0 | 0 | 0 | 0 | 0 | 0 |
| hsa-miR-3186-5p | 0 | 0 | 0 | 0 | 0 | 1 | 0 |
| hsa-miR-3187 | 6 | 3 | 1 | 3 | 0 | 3 | 0 |
| hsa-miR-3188 | 6 | 8 | 10 | 13 | 9 | 7 | 2 |
| hsa-miR-3189 | 0 | 0 | 0 | 2 | 0 | 0 | 0 |
| hsa-miR-3190-3p | 3 | 1 | 0 | 1 | 1 | 2 | 1 |
| hsa-miR-3190-5p | 3 | 1 | 0 | 1 | 1 | 2 | 1 |
| hsa-miR-3191 | 2 | 0 | 0 | 0 | 0 | 0 | 0 |
| hsa-miR-3192 | 1 | 1 | 1 | 2 | 1 | 0 | 2 |
| hsa-miR-3193 | 0 | 0 | 0 | 0 | 0 | 1 | 1 |
| hsa-miR-3194 | 10 | 3 | 2 | 5 | 2 | 2 | 5 |
| hsa-miR-3195 | 0 | 1 | 0 | 0 | 0 | 1 | 2 |
| hsa-miR-3196 | 0 | 2 | 1 | 0 | 3 | 0 | 2 |
| hsa-miR-3197 | 0 | 0 | 0 | 0 | 0 | 0 | 0 |
| hsa-miR-3198 | 0 | 0 | 0 | 0 | 0 | 1 | 0 |
| hsa-miR-3199 | 0 | 6 | 6 | 3 | 2 | 5 | 9 |
| hsa-miR-32 | 5470 | 2098 | 1462 | 1838 | 1996 | 2306 | 1090 |
| hsa-miR-32* | 68 | 26 | 24 | 24 | 29 | 11 | 13 |
| hsa-miR-3200 | 1 | 37 | 39 | 52 | 34 | 51 | 6 |
| hsa-miR-3201 | 0 | 0 | 0 | 0 | 0 | 0 | 0 |
| hsa-miR-3202 | 0 | 1 | 0 | 0 | 1 | 0 | 0 |
| hsa-miR-320a | 1244 | 6971 | 7889 | 7436 | 7785 | 7380 | 9423 |
| hsa-miR-320b | 51 | 417 | 465 | 390 | 409 | 449 | 2305 |
| hsa-miR-320c | 34 | 281 | 247 | 266 | 256 | 296 | 1932 |
| hsa-miR-320d | 46 | 314 | 284 | 321 | 258 | 359 | 2160 |
| hsa-miR-320e | 6 | 9 | 10 | 13 | 4 | 9 | 58 |
| hsa-miR-323-3p | 0 | 51 | 42 | 56 | 46 | 45 | 11 |
| hsa-miR-323-5p | 0 | 0 | 2 | 0 | 1 | 0 | 0 |
| hsa-miR-323b-3p | 0 | 22 | 12 | 24 | 24 | 24 | 1 |
| hsa-miR-323b-5p | 0 | 0 | 1 | 0 | 0 | 0 | 1 |
| hsa-miR-324-3p | 81 | 88 | 92 | 92 | 102 | 95 | 109 |
| hsa-miR-324-5p | 271 | 177 | 187 | 189 | 174 | 183 | 127 |
| hsa-miR-325 | 0 | 0 | 0 | 0 | 0 | 0 | 0 |
| hsa-miR-326 | 0 | 21 | 21 | 19 | 20 | 16 | 16 |
| hsa-miR-328 | 10 | 234 | 256 | 318 | 319 | 224 | 99 |
| hsa-miR-329 | 0 | 130 | 98 | 100 | 107 | 108 | 43 |
| hsa-miR-330-3p | 255 | 263 | 217 | 154 | 144 | 284 | 46 |
| hsa-miR-330-5p | 299 | 46 | 33 | 32 | 42 | 44 | 13 |
| hsa-miR-331-3p | 281 | 134 | 178 | 143 | 156 | 135 | 88 |
| hsa-miR-331-5p | 223 | 30 | 24 | 38 | 47 | 26 | 25 |
| hsa-miR-335 | 0 | 2630 | 2223 | 2454 | 2057 | 2932 | 4406 |
| hsa-miR-335* | 1 | 533 | 585 | 687 | 626 | 570 | 505 |
| hsa-miR-337-3p | 0 | 323 | 326 | 405 | 308 | 339 | 200 |
| hsa-miR-337-5p | 0 | 270 | 247 | 249 | 226 | 301 | 111 |
| hsa-miR-338-3p | 0 | 707 | 633 | 705 | 767 | 764 | 49 |
| hsa-miR-338-5p | 0 | 341 | 359 | 464 | 420 | 420 | 23 |
| hsa-miR-339-3p | 2226 | 606 | 610 | 725 | 721 | 707 | 442 |
| hsa-miR-339-5p | 413 | 186 | 163 | 178 | 203 | 206 | 211 |
| hsa-miR-33a | 1634 | 753 | 748 | 945 | 796 | 830 | 95 |
| hsa-miR-33a* | 223 | 15 | 12 | 16 | 16 | 14 | 9 |
| hsa-miR-33b | 385 | 46 | 47 | 67 | 59 | 52 | 58 |
| hsa-miR-33b* | 46 | 2 | 1 | 3 | 3 | 3 | 2 |
| hsa-miR-340 | 0 | 1628 | 1439 | 1189 | 1024 | 1805 | 891 |
| hsa-miR-340* | 0 | 170 | 162 | 157 | 184 | 161 | 38 |
| hsa-miR-342-3p | 1703 | 1869 | 1713 | 1975 | 2067 | 1940 | 2239 |
| hsa-miR-342-5p | 185 | 148 | 166 | 164 | 193 | 170 | 329 |
| hsa-miR-345 | 4 | 269 | 289 | 274 | 273 | 276 | 235 |
| hsa-miR-346 | 0 | 9 | 12 | 12 | 13 | 4 | 3 |
| hsa-miR-34a | 0 | 1016 | 1070 | 1335 | 1289 | 1090 | 1240 |
| hsa-miR-34a* | 0 | 10 | 6 | 8 | 6 | 10 | 9 |
| hsa-miR-34b | 0 | 93 | 81 | 100 | 104 | 99 | 9 |
| hsa-miR-34b* | 0 | 84 | 103 | 103 | 118 | 118 | 6 |
| hsa-miR-34c-3p | 0 | 128 | 137 | 153 | 174 | 151 | 17 |

TABLE 7-continued

| | Human RNA pool adaptors | | | | | | Breast |
|---|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-34c-5p | 1 | 2391 | 2526 | 2797 | 2763 | 2601 | 217 |
| hsa-miR-361-3p | 300 | 272 | 276 | 340 | 317 | 287 | 269 |
| hsa-miR-361-5p | 600 | 1507 | 1558 | 1786 | 1855 | 1606 | 1375 |
| hsa-miR-362-3p | 0 | 49 | 48 | 64 | 65 | 58 | 16 |
| hsa-miR-362-5p | 0 | 193 | 164 | 182 | 181 | 185 | 43 |
| hsa-miR-363 | 0 | 1302 | 1223 | 1382 | 1458 | 1472 | 157 |
| hsa-miR-363* | 0 | 0 | 1 | 1 | 3 | 3 | 1 |
| hsa-miR-365 | 2549 | 1375 | 1221 | 1388 | 1441 | 1463 | 2373 |
| hsa-miR-365* | 0 | 10 | 10 | 6 | 17 | 13 | 62 |
| hsa-miR-367 | 0 | 1 | 2 | 3 | 2 | 1 | 0 |
| hsa-miR-367* | 0 | 0 | 0 | 0 | 0 | 0 | 0 |
| hsa-miR-369-3p | 9 | 577 | 532 | 764 | 701 | 636 | 208 |
| hsa-miR-369-5p | 0 | 100 | 98 | 130 | 119 | 114 | 68 |
| hsa-miR-370 | 0 | 61 | 63 | 54 | 60 | 50 | 7 |
| hsa-miR-371-3p | 0 | 3 | 1 | 0 | 3 | 2 | 0 |
| hsa-miR-371-5p | 0 | 10 | 13 | 12 | 15 | 10 | 0 |
| hsa-miR-372 | 0 | 34 | 33 | 39 | 40 | 35 | 0 |
| hsa-miR-373 | 0 | 33 | 20 | 41 | 20 | 22 | 0 |
| hsa-miR-373* | 0 | 2 | 0 | 3 | 1 | 3 | 0 |
| hsa-miR-374a | 1642 | 4464 | 5594 | 8500 | 9392 | 5156 | 2047 |
| hsa-miR-374a* | 23689 | 5542 | 5001 | 6338 | 6354 | 6298 | 3692 |
| hsa-miR-374b | 543 | 3517 | 2589 | 3518 | 3701 | 4095 | 3002 |
| hsa-miR-374b* | 154 | 105 | 87 | 105 | 123 | 120 | 35 |
| hsa-miR-375 | 1 | 1319 | 1356 | 1703 | 1480 | 1624 | 638 |
| hsa-miR-376a | 0 | 87 | 66 | 76 | 89 | 73 | 27 |
| hsa-miR-376a* | 0 | 128 | 121 | 166 | 130 | 146 | 53 |
| hsa-miR-376b | 0 | 103 | 82 | 114 | 112 | 105 | 25 |
| hsa-miR-376c | 0 | 1684 | 1503 | 1867 | 1742 | 1787 | 643 |
| hsa-miR-377 | 0 | 558 | 361 | 555 | 569 | 632 | 122 |
| hsa-miR-377* | 0 | 2 | 3 | 8 | 6 | 6 | 4 |
| hsa-miR-378 | 1201524 | 154120 | 139944 | 167798 | 163364 | 166366 | 118921 |
| hsa-miR-378* | 219 | 224 | 214 | 319 | 297 | 265 | 163 |
| hsa-miR-378b | 3 | 2 | 4 | 4 | 7 | 4 | 4 |
| hsa-miR-378c | 15826 | 1643 | 1586 | 1821 | 1742 | 1796 | 1200 |
| hsa-miR-379 | 1 | 3016 | 2768 | 3255 | 3392 | 3458 | 1874 |
| hsa-miR-379* | 0 | 23 | 16 | 26 | 20 | 15 | 4 |
| hsa-miR-380 | 0 | 14 | 7 | 20 | 7 | 10 | 5 |
| hsa-miR-380* | 0 | 30 | 21 | 24 | 22 | 25 | 4 |
| hsa-miR-381 | 0 | 1429 | 1322 | 1397 | 1482 | 1589 | 443 |
| hsa-miR-382 | 0 | 135 | 142 | 129 | 154 | 159 | 79 |
| hsa-miR-383 | 0 | 55 | 74 | 56 | 64 | 79 | 29 |
| hsa-miR-384 | 0 | 0 | 0 | 0 | 0 | 0 | 0 |
| hsa-miR-409-3p | 0 | 92 | 99 | 143 | 114 | 123 | 57 |
| hsa-miR-409-5p | 0 | 27 | 29 | 57 | 36 | 36 | 16 |
| hsa-miR-410 | 0 | 94 | 102 | 105 | 91 | 118 | 15 |
| hsa-miR-411 | 2 | 823 | 809 | 981 | 1042 | 911 | 356 |
| hsa-miR-411* | 0 | 59 | 45 | 40 | 36 | 48 | 10 |
| hsa-miR-412 | 0 | 0 | 0 | 0 | 1 | 0 | 0 |
| hsa-miR-421 | 48 | 185 | 154 | 135 | 135 | 185 | 131 |
| hsa-miR-422a | 7 | 1 | 0 | 0 | 0 | 1 | 0 |
| hsa-miR-423-3p | 2241 | 2289 | 2145 | 2407 | 2539 | 2593 | 1694 |
| hsa-miR-423-5p | 11168 | 4665 | 3912 | 3296 | 2517 | 5015 | 4426 |
| hsa-miR-424 | 1 | 17513 | 16557 | 18944 | 17115 | 18702 | 4393 |
| hsa-miR-424* | 0 | 166 | 152 | 174 | 159 | 181 | 27 |
| hsa-miR-425 | 20272 | 5387 | 4390 | 5330 | 5548 | 5778 | 1961 |
| hsa-miR-425* | 463 | 181 | 166 | 241 | 248 | 219 | 224 |
| hsa-miR-4251 | 0 | 0 | 0 | 0 | 0 | 0 | 0 |
| hsa-miR-4252 | 0 | 0 | 0 | 0 | 0 | 0 | 0 |
| hsa-miR-4253 | 0 | 0 | 0 | 0 | 0 | 0 | 0 |
| hsa-miR-4254 | 0 | 0 | 1 | 0 | 0 | 1 | 0 |
| hsa-miR-4255 | 0 | 0 | 0 | 0 | 0 | 0 | 0 |
| hsa-miR-4256 | 0 | 0 | 0 | 0 | 0 | 0 | 0 |
| hsa-miR-4257 | 0 | 0 | 0 | 0 | 0 | 0 | 0 |
| hsa-miR-4258 | 0 | 0 | 0 | 0 | 0 | 0 | 0 |
| hsa-miR-4259 | 0 | 0 | 0 | 0 | 0 | 0 | 0 |
| hsa-miR-4260 | 0 | 0 | 0 | 0 | 0 | 0 | 0 |
| hsa-miR-4261 | 0 | 0 | 0 | 0 | 0 | 0 | 0 |
| hsa-miR-4262 | 0 | 0 | 0 | 0 | 0 | 0 | 0 |
| hsa-miR-4263 | 0 | 0 | 0 | 0 | 0 | 0 | 0 |
| hsa-miR-4264 | 0 | 0 | 0 | 0 | 0 | 0 | 0 |
| hsa-miR-4265 | 0 | 0 | 0 | 0 | 0 | 0 | 0 |
| hsa-miR-4266 | 0 | 0 | 0 | 0 | 0 | 0 | 0 |
| hsa-miR-4267 | 0 | 0 | 0 | 0 | 0 | 0 | 0 |
| hsa-miR-4268 | 0 | 0 | 0 | 0 | 0 | 0 | 0 |

TABLE 7-continued

|  | Human RNA pool adaptors | | | | | | Breast |
|---|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-4269 | 0 | 0 | 0 | 0 | 0 | 0 | 0 |
| hsa-miR-4270 | 0 | 0 | 0 | 0 | 0 | 0 | 0 |
| hsa-miR-4271 | 0 | 0 | 0 | 0 | 0 | 0 | 0 |
| hsa-miR-4272 | 0 | 0 | 0 | 0 | 0 | 0 | 0 |
| hsa-miR-4273 | 0 | 0 | 0 | 0 | 0 | 0 | 0 |
| hsa-miR-4274 | 0 | 0 | 0 | 0 | 0 | 0 | 0 |
| hsa-miR-4275 | 0 | 0 | 0 | 0 | 0 | 0 | 0 |
| hsa-miR-4276 | 0 | 0 | 0 | 0 | 0 | 0 | 0 |
| hsa-miR-4277 | 0 | 0 | 0 | 0 | 0 | 0 | 0 |
| hsa-miR-4278 | 0 | 0 | 0 | 0 | 0 | 0 | 0 |
| hsa-miR-4279 | 0 | 0 | 0 | 0 | 0 | 0 | 0 |
| hsa-miR-4280 | 0 | 0 | 0 | 0 | 0 | 0 | 0 |
| hsa-miR-4281 | 0 | 0 | 0 | 0 | 0 | 0 | 0 |
| hsa-miR-4282 | 0 | 0 | 0 | 0 | 0 | 0 | 0 |
| hsa-miR-4283 | 0 | 0 | 0 | 0 | 0 | 0 | 0 |
| hsa-miR-4284 | 38 | 97 | 85 | 83 | 79 | 110 | 311 |
| hsa-miR-4285 | 0 | 0 | 0 | 0 | 0 | 0 | 0 |
| hsa-miR-4286 | 63 | 95 | 91 | 111 | 101 | 93 | 131 |
| hsa-miR-4287 | 0 | 0 | 0 | 0 | 0 | 0 | 0 |
| hsa-miR-4288 | 0 | 0 | 0 | 0 | 0 | 0 | 0 |
| hsa-miR-4289 | 0 | 0 | 0 | 0 | 0 | 0 | 0 |
| hsa-miR-429 | 0 | 1694 | 1868 | 2088 | 2178 | 1959 | 1384 |
| hsa-miR-4290 | 0 | 0 | 0 | 0 | 0 | 0 | 0 |
| hsa-miR-4291 | 0 | 0 | 0 | 0 | 0 | 0 | 0 |
| hsa-miR-4292 | 0 | 0 | 0 | 0 | 0 | 0 | 0 |
| hsa-miR-4293 | 0 | 0 | 0 | 0 | 0 | 0 | 0 |
| hsa-miR-4294 | 0 | 0 | 0 | 0 | 0 | 0 | 0 |
| hsa-miR-4295 | 0 | 0 | 0 | 0 | 0 | 0 | 0 |
| hsa-miR-4296 | 0 | 0 | 0 | 0 | 1 | 0 | 0 |
| hsa-miR-4297 | 0 | 0 | 0 | 0 | 0 | 0 | 0 |
| hsa-miR-4298 | 0 | 0 | 0 | 0 | 0 | 0 | 0 |
| hsa-miR-4299 | 0 | 0 | 0 | 0 | 0 | 0 | 0 |
| hsa-miR-4300 | 0 | 0 | 0 | 0 | 0 | 0 | 0 |
| hsa-miR-4301 | 0 | 0 | 0 | 0 | 0 | 0 | 0 |
| hsa-miR-4302 | 0 | 0 | 0 | 0 | 0 | 0 | 0 |
| hsa-miR-4303 | 0 | 0 | 0 | 0 | 0 | 0 | 0 |
| hsa-miR-4304 | 0 | 0 | 0 | 0 | 0 | 0 | 0 |
| hsa-miR-4305 | 0 | 0 | 0 | 0 | 0 | 0 | 0 |
| hsa-miR-4306 | 0 | 0 | 0 | 0 | 0 | 0 | 0 |
| hsa-miR-4307 | 0 | 0 | 0 | 0 | 0 | 0 | 0 |
| hsa-miR-4308 | 0 | 0 | 0 | 0 | 0 | 0 | 0 |
| hsa-miR-4309 | 0 | 0 | 0 | 0 | 0 | 0 | 0 |
| hsa-miR-431 | 0 | 21 | 9 | 10 | 8 | 11 | 2 |
| hsa-miR-431* | 0 | 13 | 11 | 8 | 11 | 12 | 5 |
| hsa-miR-4310 | 0 | 0 | 0 | 0 | 0 | 0 | 0 |
| hsa-miR-4311 | 0 | 0 | 0 | 0 | 0 | 0 | 0 |
| hsa-miR-4312 | 0 | 0 | 0 | 0 | 0 | 0 | 0 |
| hsa-miR-4313 | 0 | 0 | 0 | 0 | 0 | 0 | 0 |
| hsa-miR-4314 | 0 | 0 | 0 | 0 | 0 | 0 | 0 |
| hsa-miR-4315 | 0 | 0 | 0 | 0 | 0 | 0 | 0 |
| hsa-miR-4316 | 0 | 0 | 0 | 0 | 0 | 0 | 0 |
| hsa-miR-4317 | 0 | 0 | 0 | 0 | 0 | 0 | 0 |
| hsa-miR-4318 | 0 | 0 | 0 | 0 | 0 | 0 | 0 |
| hsa-miR-4319 | 0 | 0 | 0 | 0 | 0 | 0 | 0 |
| hsa-miR-432 | 0 | 74 | 79 | 71 | 84 | 92 | 71 |
| hsa-miR-432* | 0 | 2 | 1 | 0 | 2 | 0 | 0 |
| hsa-miR-4320 | 0 | 0 | 0 | 0 | 0 | 0 | 0 |
| hsa-miR-4321 | 0 | 0 | 0 | 0 | 0 | 0 | 0 |
| hsa-miR-4322 | 0 | 0 | 0 | 0 | 0 | 0 | 0 |
| hsa-miR-4323 | 0 | 0 | 0 | 0 | 0 | 1 | 0 |
| hsa-miR-4324 | 0 | 0 | 0 | 0 | 0 | 0 | 0 |
| hsa-miR-4325 | 0 | 0 | 0 | 0 | 0 | 0 | 0 |
| hsa-miR-4326 | 24 | 4 | 6 | 3 | 5 | 5 | 2 |
| hsa-miR-4327 | 0 | 0 | 0 | 0 | 0 | 0 | 0 |
| hsa-miR-4328 | 0 | 2 | 7 | 7 | 3 | 6 | 0 |
| hsa-miR-4329 | 0 | 0 | 0 | 0 | 0 | 0 | 0 |
| hsa-miR-433 | 0 | 50 | 32 | 38 | 38 | 45 | 10 |
| hsa-miR-4330 | 0 | 0 | 0 | 0 | 0 | 0 | 0 |
| hsa-miR-448 | 0 | 1 | 1 | 0 | 0 | 1 | 0 |
| hsa-miR-449a | 10 | 679 | 644 | 797 | 884 | 758 | 13 |
| hsa-miR-449b | 2 | 108 | 94 | 129 | 111 | 149 | 5 |
| hsa-miR-449b* | 0 | 5 | 1 | 1 | 4 | 2 | 0 |
| hsa-miR-449c | 5 | 110 | 102 | 101 | 101 | 134 | 2 |
| hsa-miR-449c* | 0 | 0 | 0 | 0 | 0 | 0 | 0 |

TABLE 7-continued

|  | Human RNA pool adaptors | | | | | Breast |
|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-450a | 0 | 876 | 877 | 1040 | 1138 | 927 | 261 |
| hsa-miR-450b-3p | 0 | 3 | 4 | 0 | 8 | 3 | 2 |
| hsa-miR-450b-5p | 0 | 385 | 341 | 414 | 431 | 420 | 101 |
| hsa-miR-451 | 5 | 54380 | 51253 | 59248 | 61747 | 60268 | 25583 |
| hsa-miR-452 | 0 | 6482 | 5791 | 6960 | 6629 | 7039 | 19691 |
| hsa-miR-452* | 0 | 136 | 149 | 150 | 160 | 147 | 389 |
| hsa-miR-454 | 939 | 1874 | 1335 | 1717 | 1577 | 2044 | 615 |
| hsa-miR-454* | 6 | 5 | 8 | 14 | 7 | 8 | 3 |
| hsa-miR-455-3p | 0 | 1300 | 1114 | 1459 | 1285 | 1398 | 456 |
| hsa-miR-455-5p | 0 | 311 | 241 | 319 | 326 | 303 | 131 |
| hsa-miR-466 | 0 | 0 | 0 | 1 | 0 | 0 | 0 |
| hsa-miR-483-3p | 0 | 31 | 40 | 31 | 27 | 36 | 11 |
| hsa-miR-483-5p | 0 | 220 | 208 | 223 | 160 | 229 | 156 |
| hsa-miR-484 | 367 | 204 | 170 | 193 | 238 | 222 | 116 |
| hsa-miR-485-3p | 0 | 47 | 48 | 40 | 41 | 34 | 7 |
| hsa-miR-485-5p | 0 | 75 | 59 | 61 | 41 | 74 | 18 |
| hsa-miR-486-3p | 6 | 25 | 14 | 28 | 20 | 38 | 5 |
| hsa-miR-486-5p | 52 | 1057 | 1088 | 1112 | 1126 | 1079 | 435 |
| hsa-miR-487a | 0 | 43 | 35 | 55 | 40 | 57 | 14 |
| hsa-miR-487b | 3 | 213 | 209 | 231 | 266 | 225 | 56 |
| hsa-miR-488 | 0 | 21 | 28 | 23 | 40 | 24 | 10 |
| hsa-miR-488* | 0 | 0 | 0 | 3 | 4 | 2 | 0 |
| hsa-miR-489 | 0 | 54 | 46 | 29 | 35 | 45 | 46 |
| hsa-miR-490-3p | 0 | 89 | 93 | 107 | 99 | 105 | 0 |
| hsa-miR-490-5p | 0 | 100 | 74 | 97 | 90 | 82 | 1 |
| hsa-miR-491-3p | 19 | 3 | 8 | 4 | 7 | 7 | 1 |
| hsa-miR-491-5p | 22 | 53 | 48 | 65 | 37 | 61 | 65 |
| hsa-miR-492 | 0 | 0 | 0 | 3 | 0 | 1 | 0 |
| hsa-miR-493 | 0 | 82 | 80 | 75 | 104 | 94 | 10 |
| hsa-miR-493* | 0 | 201 | 190 | 248 | 207 | 198 | 23 |
| hsa-miR-494 | 4 | 212 | 200 | 227 | 210 | 196 | 167 |
| hsa-miR-495 | 0 | 197 | 201 | 231 | 248 | 267 | 62 |
| hsa-miR-496 | 0 | 6 | 5 | 7 | 8 | 12 | 1 |
| hsa-miR-497 | 1 | 737 | 729 | 811 | 815 | 831 | 1169 |
| hsa-miR-497* | 0 | 21 | 25 | 42 | 38 | 26 | 6 |
| hsa-miR-498 | 0 | 105 | 68 | 88 | 91 | 94 | 0 |
| hsa-miR-499-3p | 2 | 600 | 758 | 911 | 1002 | 652 | 12 |
| hsa-miR-499-5p | 7 | 1417 | 1293 | 1309 | 1223 | 1611 | 27 |
| hsa-miR-500 | 0 | 73 | 86 | 101 | 117 | 107 | 43 |
| hsa-miR-500* | 0 | 220 | 195 | 231 | 213 | 230 | 109 |
| hsa-miR-500b | 0 | 61 | 71 | 79 | 91 | 85 | 35 |
| hsa-miR-501-3p | 0 | 48 | 52 | 52 | 45 | 51 | 23 |
| hsa-miR-501-5p | 0 | 49 | 41 | 40 | 41 | 39 | 10 |
| hsa-miR-502-3p | 0 | 139 | 109 | 169 | 166 | 150 | 78 |
| hsa-miR-502-5p | 0 | 20 | 20 | 11 | 14 | 13 | 4 |
| hsa-miR-503 | 0 | 358 | 309 | 333 | 280 | 451 | 53 |
| hsa-miR-504 | 0 | 49 | 49 | 54 | 50 | 54 | 16 |
| hsa-miR-505 | 318 | 238 | 244 | 291 | 277 | 287 | 280 |
| hsa-miR-505* | 61 | 33 | 43 | 56 | 47 | 39 | 50 |
| hsa-miR-506 | 3 | 1390 | 1265 | 1292 | 1341 | 1382 | 2 |
| hsa-miR-507 | 0 | 77 | 93 | 85 | 111 | 95 | 0 |
| hsa-miR-508-3p | 5 | 5047 | 4957 | 5494 | 5780 | 5597 | 15 |
| hsa-miR-508-5p | 0 | 90 | 107 | 74 | 69 | 123 | 0 |
| hsa-miR-509-3-5p | 0 | 255 | 201 | 176 | 142 | 292 | 1 |
| hsa-miR-509-3p | 0 | 466 | 451 | 526 | 568 | 559 | 6 |
| hsa-miR-509-5p | 0 | 619 | 484 | 291 | 225 | 727 | 0 |
| hsa-miR-510 | 0 | 296 | 153 | 136 | 80 | 346 | 1 |
| hsa-miR-511 | 0 | 12 | 13 | 24 | 20 | 19 | 45 |
| hsa-miR-512-3p | 0 | 442 | 422 | 532 | 537 | 482 | 1 |
| hsa-miR-512-5p | 0 | 178 | 134 | 208 | 221 | 230 | 0 |
| hsa-miR-513a-3p | 0 | 72 | 46 | 47 | 50 | 79 | 0 |
| hsa-miR-513a-5p | 0 | 174 | 174 | 149 | 119 | 204 | 1 |
| hsa-miR-513b | 0 | 81 | 59 | 78 | 65 | 85 | 1 |
| hsa-miR-513c | 1 | 285 | 270 | 322 | 277 | 313 | 0 |
| hsa-miR-514 | 16 | 12019 | 10822 | 12656 | 13364 | 13113 | 15 |
| hsa-miR-514b-3p | 0 | 53 | 61 | 72 | 75 | 62 | 0 |
| hsa-miR-514b-5p | 0 | 235 | 202 | 167 | 92 | 279 | 0 |
| hsa-miR-515-3p | 0 | 240 | 221 | 307 | 255 | 262 | 2 |
| hsa-miR-515-5p | 0 | 1542 | 1362 | 1693 | 1677 | 1619 | 10 |
| hsa-miR-516a-3p | 0 | 21 | 21 | 19 | 18 | 16 | 0 |
| hsa-miR-516a-5p | 0 | 4667 | 4195 | 4189 | 4168 | 5181 | 12 |
| hsa-miR-516b | 0 | 2726 | 2424 | 2769 | 2772 | 3014 | 7 |
| hsa-miR-516b* | 0 | 21 | 21 | 19 | 18 | 16 | 0 |

TABLE 7-continued

| | Human RNA pool adaptors | | | | | Breast |
|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-517* | 0 | 149 | 157 | 193 | 189 | 157 | 0 |
| hsa-miR-517a | 0 | 2741 | 2416 | 2981 | 3028 | 2862 | 20 |
| hsa-miR-517b | 0 | 2741 | 2416 | 2981 | 3028 | 2862 | 20 |
| hsa-miR-517c | 0 | 698 | 612 | 729 | 771 | 715 | 1 |
| hsa-miR-518a-3p | 0 | 806 | 768 | 902 | 828 | 789 | 4 |
| hsa-miR-518a-5p | 0 | 134 | 99 | 157 | 157 | 123 | 1 |
| hsa-miR-518b | 0 | 1442 | 1360 | 1575 | 1500 | 1543 | 14 |
| hsa-miR-518c | 0 | 3938 | 2640 | 3417 | 3452 | 4221 | 16 |
| hsa-miR-518c* | 0 | 62 | 43 | 52 | 72 | 69 | 0 |
| hsa-miR-518d-3p | 0 | 16 | 21 | 34 | 24 | 26 | 0 |
| hsa-miR-518d-5p | 0 | 119 | 128 | 245 | 271 | 157 | 2 |
| hsa-miR-518e | 0 | 449 | 466 | 446 | 421 | 467 | 2 |
| hsa-miR-518e* | 0 | 1853 | 1674 | 2382 | 2278 | 2063 | 26 |
| hsa-miR-518f | 0 | 930 | 855 | 925 | 845 | 980 | 7 |
| hsa-miR-518f* | 0 | 90 | 102 | 147 | 155 | 120 | 2 |
| hsa-miR-519a | 0 | 1316 | 1191 | 1350 | 1357 | 1415 | 3 |
| hsa-miR-519a* | 0 | 1853 | 1674 | 2382 | 2278 | 2063 | 26 |
| hsa-miR-519b-3p | 0 | 161 | 144 | 167 | 152 | 189 | 4 |
| hsa-miR-519b-5p | 0 | 1853 | 1674 | 2382 | 2278 | 2063 | 26 |
| hsa-miR-519c-3p | 0 | 459 | 433 | 475 | 443 | 484 | 8 |
| hsa-miR-519c-5p | 0 | 1853 | 1674 | 2382 | 2278 | 2063 | 26 |
| hsa-miR-519d | 0 | 912 | 750 | 964 | 967 | 986 | 7 |
| hsa-miR-519e | 0 | 21 | 17 | 11 | 20 | 19 | 0 |
| hsa-miR-519e* | 0 | 69 | 34 | 47 | 47 | 67 | 0 |
| hsa-miR-520a-3p | 0 | 181 | 148 | 193 | 179 | 164 | 1 |
| hsa-miR-520a-5p | 0 | 236 | 209 | 264 | 256 | 269 | 1 |
| hsa-miR-520b | 0 | 156 | 132 | 181 | 155 | 172 | 4 |
| hsa-miR-520c-3p | 0 | 156 | 132 | 181 | 155 | 172 | 4 |
| hsa-miR-520c-5p | 0 | 119 | 128 | 245 | 271 | 157 | 2 |
| hsa-miR-520d-3p | 0 | 108 | 134 | 139 | 131 | 134 | 0 |
| hsa-miR-520d-5p | 0 | 88 | 60 | 98 | 75 | 92 | 1 |
| hsa-miR-520e | 0 | 19 | 15 | 20 | 17 | 15 | 0 |
| hsa-miR-520f | 0 | 303 | 275 | 314 | 321 | 332 | 17 |
| hsa-miR-520g | 0 | 696 | 730 | 941 | 899 | 809 | 12 |
| hsa-miR-520h | 0 | 945 | 985 | 1293 | 1214 | 1076 | 19 |
| hsa-miR-521 | 0 | 212 | 137 | 220 | 201 | 225 | 1 |
| hsa-miR-522 | 0 | 351 | 323 | 341 | 381 | 370 | 1 |
| hsa-miR-522* | 0 | 1853 | 1674 | 2382 | 2278 | 2063 | 26 |
| hsa-miR-523 | 0 | 1184 | 1243 | 1474 | 1434 | 1261 | 7 |
| hsa-miR-523* | 0 | 1853 | 1674 | 2382 | 2278 | 2063 | 26 |
| hsa-miR-524-3p | 0 | 147 | 112 | 132 | 104 | 176 | 2 |
| hsa-miR-524-5p | 0 | 152 | 173 | 179 | 197 | 188 | 6 |
| hsa-miR-525-3p | 0 | 571 | 547 | 692 | 584 | 529 | 1 |
| hsa-miR-525-5p | 0 | 368 | 353 | 400 | 383 | 384 | 3 |
| hsa-miR-526a | 0 | 119 | 128 | 245 | 271 | 157 | 2 |
| hsa-miR-526b | 0 | 602 | 491 | 683 | 564 | 599 | 2 |
| hsa-miR-526b* | 0 | 115 | 115 | 131 | 123 | 145 | 2 |
| hsa-miR-527 | 0 | 134 | 99 | 157 | 157 | 123 | 1 |
| hsa-miR-532-3p | 0 | 297 | 291 | 361 | 366 | 346 | 238 |
| hsa-miR-532-5p | 0 | 1094 | 973 | 1063 | 1106 | 1140 | 451 |
| hsa-miR-539 | 0 | 77 | 100 | 120 | 123 | 94 | 34 |
| hsa-miR-541 | 0 | 0 | 1 | 0 | 0 | 0 | 1 |
| hsa-miR-541* | 1 | 0 | 0 | 0 | 1 | 2 | 0 |
| hsa-miR-542-3p | 5 | 2302 | 2186 | 2577 | 2608 | 2393 | 594 |
| hsa-miR-542-5p | 0 | 244 | 264 | 263 | 260 | 260 | 72 |
| hsa-miR-543 | 0 | 31 | 47 | 34 | 41 | 30 | 6 |
| hsa-miR-544 | 0 | 1 | 2 | 5 | 4 | 5 | 1 |
| hsa-miR-544b | 1 | 0 | 0 | 0 | 0 | 0 | 0 |
| hsa-miR-545 | 15 | 1 | 6 | 7 | 7 | 14 | 2 |
| hsa-miR-545* | 16 | 3 | 12 | 11 | 11 | 7 | 11 |
| hsa-miR-548a-3p | 0 | 8 | 7 | 13 | 12 | 8 | 0 |
| hsa-miR-548a-5p | 0 | 2 | 0 | 1 | 2 | 1 | 1 |
| hsa-miR-548b-3p | 0 | 7 | 10 | 7 | 20 | 8 | 12 |
| hsa-miR-548b-5p | 0 | 0 | 1 | 2 | 5 | 8 | 3 |
| hsa-miR-548c-3p | 9 | 0 | 1 | 0 | 0 | 1 | 0 |
| hsa-miR-548c-5p | 6 | 20 | 23 | 28 | 29 | 24 | 9 |
| hsa-miR-548d-3p | 13 | 0 | 5 | 5 | 3 | 3 | 2 |
| hsa-miR-548d-5p | 37 | 23 | 30 | 45 | 45 | 32 | 6 |
| hsa-miR-548e | 258 | 30 | 32 | 18 | 17 | 41 | 6 |
| hsa-miR-548f | 109 | 4 | 4 | 7 | 10 | 5 | 2 |
| hsa-miR-548g | 1 | 0 | 0 | 0 | 0 | 0 | 0 |
| hsa-miR-548h | 0 | 0 | 0 | 2 | 3 | 1 | 0 |
| hsa-miR-548i | 0 | 7 | 8 | 12 | 10 | 12 | 1 |
| hsa-miR-548j | 63 | 15 | 18 | 14 | 26 | 10 | 7 |

TABLE 7-continued

| RNA miRNA | Human RNA pool adaptors | | | | | | Breast |
|---|---|---|---|---|---|---|---|
| | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-548k | 20 | 16 | 7 | 11 | 4 | 18 | 6 |
| hsa-miR-548l | 9 | 5 | 2 | 4 | 2 | 4 | 0 |
| hsa-miR-548m | 0 | 0 | 0 | 0 | 0 | 0 | 0 |
| hsa-miR-548n | 15 | 4 | 3 | 4 | 7 | 4 | 0 |
| hsa-miR-548o | 60 | 12 | 6 | 11 | 8 | 12 | 9 |
| hsa-miR-548p | 1 | 0 | 0 | 1 | 0 | 1 | 0 |
| hsa-miR-548q | 2 | 4 | 9 | 6 | 5 | 4 | 4 |
| hsa-miR-548s | 0 | 0 | 0 | 2 | 1 | 1 | 1 |
| hsa-miR-548t | 3 | 0 | 0 | 1 | 3 | 4 | 1 |
| hsa-miR-548u | 1 | 0 | 0 | 1 | 1 | 0 | 0 |
| hsa-miR-548v | 0 | 1 | 1 | 2 | 2 | 2 | 4 |
| hsa-miR-548w | 0 | 1 | 0 | 0 | 0 | 0 | 0 |
| hsa-miR-548x | 0 | 0 | 0 | 0 | 0 | 0 | 0 |
| hsa-miR-549 | 0 | 4 | 1 | 0 | 2 | 5 | 0 |
| hsa-miR-550 | 0 | 10 | 16 | 21 | 12 | 15 | 11 |
| hsa-miR-550* | 3 | 13 | 11 | 7 | 6 | 10 | 7 |
| hsa-miR-551a | 2 | 4 | 0 | 4 | 1 | 4 | 2 |
| hsa-miR-551b | 0 | 10 | 6 | 10 | 17 | 11 | 34 |
| hsa-miR-551b* | 0 | 1 | 1 | 2 | 2 | 2 | 0 |
| hsa-miR-552 | 2 | 4 | 2 | 4 | 2 | 2 | 0 |
| hsa-miR-553 | 0 | 0 | 0 | 0 | 0 | 0 | 0 |
| hsa-miR-554 | 0 | 0 | 0 | 0 | 0 | 0 | 0 |
| hsa-miR-555 | 0 | 0 | 0 | 0 | 0 | 0 | 0 |
| hsa-miR-556-3p | 0 | 0 | 1 | 1 | 3 | 1 | 3 |
| hsa-miR-556-5p | 0 | 17 | 9 | 13 | 9 | 6 | 9 |
| hsa-miR-557 | 0 | 0 | 0 | 0 | 0 | 0 | 0 |
| hsa-miR-558 | 0 | 0 | 0 | 0 | 0 | 0 | 0 |
| hsa-miR-559 | 0 | 1 | 0 | 2 | 1 | 0 | 0 |
| hsa-miR-561 | 0 | 2 | 1 | 2 | 2 | 2 | 0 |
| hsa-miR-562 | 0 | 0 | 0 | 0 | 0 | 0 | 0 |
| hsa-miR-563 | 0 | 0 | 0 | 0 | 0 | 0 | 0 |
| hsa-miR-564 | 0 | 0 | 0 | 1 | 0 | 0 | 0 |
| hsa-miR-566 | 0 | 0 | 0 | 0 | 0 | 0 | 0 |
| hsa-miR-567 | 0 | 0 | 0 | 0 | 0 | 0 | 0 |
| hsa-miR-568 | 0 | 0 | 0 | 0 | 0 | 0 | 0 |
| hsa-miR-569 | 0 | 0 | 0 | 0 | 0 | 0 | 0 |
| hsa-miR-570 | 8 | 10 | 15 | 9 | 10 | 11 | 15 |
| hsa-miR-571 | 0 | 0 | 0 | 0 | 0 | 0 | 0 |
| hsa-miR-572 | 0 | 1 | 0 | 0 | 0 | 0 | 0 |
| hsa-miR-573 | 198 | 0 | 1 | 0 | 0 | 0 | 0 |
| hsa-miR-574-3p | 0 | 729 | 814 | 1021 | 1042 | 847 | 702 |
| hsa-miR-574-5p | 0 | 133 | 123 | 136 | 124 | 121 | 169 |
| hsa-miR-575 | 0 | 0 | 0 | 0 | 0 | 0 | 0 |
| hsa-miR-576-3p | 125 | 34 | 55 | 58 | 61 | 43 | 31 |
| hsa-miR-576-5p | 75 | 120 | 94 | 113 | 107 | 136 | 44 |
| hsa-miR-577 | 1234 | 169 | 154 | 215 | 178 | 204 | 8 |
| hsa-miR-578 | 0 | 0 | 0 | 0 | 0 | 0 | 0 |
| hsa-miR-579 | 11 | 6 | 6 | 5 | 7 | 7 | 2 |
| hsa-miR-580 | 55 | 9 | 7 | 8 | 10 | 10 | 0 |
| hsa-miR-581 | 2 | 1 | 1 | 2 | 1 | 0 | 5 |
| hsa-miR-582-3p | 1484 | 121 | 118 | 137 | 145 | 135 | 26 |
| hsa-miR-582-5p | 592 | 149 | 183 | 177 | 151 | 163 | 35 |
| hsa-miR-583 | 0 | 0 | 0 | 0 | 0 | 0 | 0 |
| hsa-miR-584 | 0 | 108 | 96 | 109 | 111 | 104 | 22 |
| hsa-miR-585 | 0 | 39 | 24 | 30 | 46 | 31 | 12 |
| hsa-miR-586 | 0 | 0 | 0 | 0 | 0 | 0 | 0 |
| hsa-miR-587 | 0 | 0 | 0 | 0 | 0 | 0 | 0 |
| hsa-miR-588 | 0 | 0 | 0 | 0 | 0 | 0 | 0 |
| hsa-miR-589 | 635 | 46 | 59 | 54 | 62 | 71 | 49 |
| hsa-miR-589* | 85 | 8 | 5 | 8 | 5 | 3 | 6 |
| hsa-miR-590-3p | 650 | 373 | 395 | 381 | 399 | 415 | 178 |
| hsa-miR-590-5p | 333 | 859 | 660 | 849 | 758 | 905 | 275 |
| hsa-miR-591 | 0 | 0 | 0 | 0 | 0 | 0 | 0 |
| hsa-miR-592 | 1 | 20 | 14 | 22 | 26 | 15 | 0 |
| hsa-miR-593 | 0 | 0 | 0 | 0 | 0 | 0 | 0 |
| hsa-miR-593* | 0 | 0 | 0 | 0 | 0 | 0 | 0 |
| hsa-miR-595 | 0 | 0 | 0 | 0 | 0 | 0 | 0 |
| hsa-miR-596 | 0 | 0 | 0 | 0 | 0 | 0 | 0 |
| hsa-miR-597 | 2 | 5 | 3 | 5 | 2 | 2 | 2 |
| hsa-miR-598 | 2107 | 680 | 705 | 799 | 758 | 750 | 133 |
| hsa-miR-599 | 0 | 0 | 0 | 0 | 1 | 0 | 0 |
| hsa-miR-600 | 0 | 0 | 1 | 0 | 0 | 0 | 0 |
| hsa-miR-601 | 0 | 0 | 0 | 0 | 0 | 0 | 0 |
| hsa-miR-602 | 0 | 1 | 0 | 0 | 0 | 1 | 0 |

TABLE 7-continued

|  | Human RNA pool adaptors | | | | | | Breast |
|---|---|---|---|---|---|---|---|
| RNA miRNA | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-603 | 0 | 1 | 0 | 0 | 0 | 0 | 0 |
| hsa-miR-604 | 0 | 0 | 0 | 0 | 0 | 0 | 0 |
| hsa-miR-605 | 0 | 0 | 0 | 1 | 4 | 1 | 0 |
| hsa-miR-606 | 0 | 0 | 0 | 0 | 0 | 0 | 0 |
| hsa-miR-607 | 1 | 0 | 0 | 0 | 0 | 0 | 0 |
| hsa-miR-608 | 0 | 0 | 0 | 0 | 0 | 0 | 0 |
| hsa-miR-609 | 0 | 0 | 0 | 0 | 1 | 0 | 0 |
| hsa-miR-610 | 1 | 0 | 2 | 0 | 0 | 0 | 0 |
| hsa-miR-611 | 0 | 0 | 0 | 0 | 0 | 0 | 0 |
| hsa-miR-612 | 0 | 0 | 0 | 0 | 0 | 0 | 0 |
| hsa-miR-613 | 0 | 0 | 0 | 0 | 0 | 0 | 0 |
| hsa-miR-614 | 0 | 1 | 0 | 0 | 0 | 0 | 0 |
| hsa-miR-615-3p | 0 | 16 | 26 | 27 | 35 | 28 | 45 |
| hsa-miR-615-5p | 0 | 0 | 0 | 2 | 2 | 0 | 0 |
| hsa-miR-616 | 7 | 3 | 4 | 3 | 2 | 5 | 3 |
| hsa-miR-616* | 4 | 23 | 18 | 20 | 26 | 30 | 8 |
| hsa-miR-617 | 0 | 0 | 0 | 0 | 0 | 0 | 0 |
| hsa-miR-618 | 0 | 26 | 25 | 28 | 30 | 28 | 31 |
| hsa-miR-619 | 0 | 0 | 0 | 0 | 0 | 0 | 0 |
| hsa-miR-620 | 0 | 0 | 0 | 0 | 0 | 0 | 0 |
| hsa-miR-621 | 0 | 0 | 0 | 0 | 0 | 0 | 0 |
| hsa-miR-622 | 0 | 1 | 1 | 0 | 0 | 1 | 0 |
| hsa-miR-623 | 0 | 0 | 0 | 0 | 0 | 0 | 0 |
| hsa-miR-624 | 0 | 3 | 6 | 2 | 6 | 4 | 0 |
| hsa-miR-624* | 32 | 14 | 7 | 9 | 7 | 9 | 7 |
| hsa-miR-625 | 76 | 60 | 63 | 73 | 62 | 65 | 64 |
| hsa-miR-625* | 255 | 116 | 72 | 119 | 100 | 94 | 58 |
| hsa-miR-626 | 0 | 0 | 0 | 0 | 0 | 0 | 0 |
| hsa-miR-627 | 703 | 78 | 62 | 81 | 67 | 79 | 68 |
| hsa-miR-628-3p | 11 | 122 | 116 | 117 | 87 | 144 | 47 |
| hsa-miR-628-5p | 132 | 440 | 405 | 491 | 506 | 526 | 129 |
| hsa-miR-629 | 516 | 36 | 40 | 43 | 53 | 46 | 78 |
| hsa-miR-629* | 67 | 10 | 12 | 10 | 15 | 17 | 9 |
| hsa-miR-630 | 0 | 0 | 0 | 0 | 0 | 0 | 0 |
| hsa-miR-631 | 0 | 0 | 0 | 0 | 0 | 0 | 0 |
| hsa-miR-632 | 2 | 0 | 0 | 0 | 0 | 0 | 0 |
| hsa-miR-633 | 0 | 0 | 0 | 0 | 0 | 0 | 0 |
| hsa-miR-634 | 0 | 0 | 0 | 0 | 0 | 0 | 0 |
| hsa-miR-635 | 0 | 0 | 0 | 0 | 0 | 0 | 0 |
| hsa-miR-636 | 1 | 2 | 0 | 0 | 0 | 0 | 0 |
| hsa-miR-637 | 0 | 0 | 0 | 0 | 0 | 0 | 0 |
| hsa-miR-638 | 0 | 0 | 0 | 0 | 0 | 0 | 0 |
| hsa-miR-639 | 1 | 0 | 0 | 0 | 1 | 0 | 0 |
| hsa-miR-640 | 0 | 0 | 0 | 0 | 0 | 0 | 0 |
| hsa-miR-641 | 10 | 10 | 9 | 7 | 3 | 13 | 3 |
| hsa-miR-642 | 1 | 6 | 3 | 8 | 5 | 5 | 4 |
| hsa-miR-643 | 12 | 3 | 2 | 7 | 10 | 5 | 6 |
| hsa-miR-644 | 0 | 0 | 0 | 0 | 0 | 0 | 0 |
| hsa-miR-645 | 0 | 0 | 0 | 0 | 0 | 0 | 0 |
| hsa-miR-646 | 0 | 0 | 0 | 0 | 0 | 0 | 0 |
| hsa-miR-647 | 0 | 0 | 0 | 0 | 0 | 0 | 0 |
| hsa-miR-648 | 0 | 0 | 0 | 0 | 0 | 0 | 0 |
| hsa-miR-649 | 0 | 0 | 0 | 0 | 0 | 0 | 0 |
| hsa-miR-650 | 0 | 1 | 0 | 0 | 0 | 0 | 0 |
| hsa-miR-651 | 372 | 55 | 60 | 55 | 54 | 65 | 42 |
| hsa-miR-652 | 160 | 330 | 330 | 316 | 329 | 325 | 437 |
| hsa-miR-653 | 0 | 43 | 32 | 37 | 53 | 39 | 44 |
| hsa-miR-654-3p | 0 | 135 | 128 | 182 | 161 | 161 | 102 |
| hsa-miR-654-5p | 0 | 5 | 13 | 12 | 12 | 12 | 5 |
| hsa-miR-655 | 0 | 137 | 128 | 185 | 178 | 183 | 72 |
| hsa-miR-656 | 0 | 13 | 19 | 27 | 16 | 21 | 18 |
| hsa-miR-657 | 0 | 0 | 0 | 0 | 0 | 0 | 0 |
| hsa-miR-658 | 0 | 0 | 0 | 0 | 0 | 0 | 0 |
| hsa-miR-659 | 2 | 0 | 0 | 0 | 0 | 0 | 0 |
| hsa-miR-660 | 0 | 271 | 259 | 280 | 290 | 334 | 171 |
| hsa-miR-661 | 0 | 0 | 0 | 0 | 0 | 0 | 0 |
| hsa-miR-662 | 0 | 0 | 0 | 0 | 0 | 0 | 0 |
| hsa-miR-663 | 0 | 2 | 2 | 5 | 3 | 4 | 17 |
| hsa-miR-663b | 10 | 4 | 1 | 6 | 2 | 1 | 1 |
| hsa-miR-664 | 483 | 198 | 174 | 218 | 213 | 206 | 152 |
| hsa-miR-664* | 98 | 136 | 127 | 184 | 177 | 174 | 200 |
| hsa-miR-665 | 0 | 4 | 7 | 5 | 6 | 2 | 7 |
| hsa-miR-668 | 0 | 1 | 3 | 2 | 6 | 5 | 0 |
| hsa-miR-670 | 0 | 1 | 0 | 0 | 3 | 0 | 0 |

TABLE 7-continued

| RNA miRNA | Human RNA pool adaptors | | | | | | Breast |
|---|---|---|---|---|---|---|---|
| | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-671-3p | 25 | 6 | 4 | 7 | 8 | 6 | 3 |
| hsa-miR-671-5p | 529 | 151 | 163 | 167 | 155 | 149 | 183 |
| hsa-miR-675 | 0 | 8 | 7 | 11 | 2 | 7 | 5 |
| hsa-miR-675* | 0 | 255 | 247 | 323 | 283 | 247 | 115 |
| hsa-miR-7 | 3569 | 3622 | 2924 | 2472 | 1896 | 4096 | 257 |
| hsa-miR-708 | 0 | 1228 | 1437 | 1479 | 1584 | 1298 | 1056 |
| hsa-miR-708* | 0 | 68 | 48 | 79 | 76 | 72 | 35 |
| hsa-miR-7-1* | 295 | 64 | 57 | 58 | 57 | 35 | 22 |
| hsa-miR-711 | 0 | 0 | 0 | 0 | 0 | 0 | 0 |
| hsa-miR-718 | 0 | 0 | 0 | 0 | 0 | 0 | 0 |
| hsa-miR-7-2* | 0 | 12 | 5 | 9 | 6 | 7 | 4 |
| hsa-miR-720 | 154 | 188 | 204 | 273 | 188 | 188 | 30 |
| hsa-miR-744 | 862 | 707 | 698 | 750 | 701 | 733 | 628 |
| hsa-miR-744* | 20 | 27 | 21 | 32 | 24 | 15 | 11 |
| hsa-miR-758 | 0 | 5 | 7 | 7 | 8 | 6 | 2 |
| hsa-miR-759 | 0 | 0 | 0 | 0 | 0 | 0 | 0 |
| hsa-miR-760 | 1 | 5 | 9 | 4 | 6 | 6 | 10 |
| hsa-miR-761 | 0 | 0 | 0 | 0 | 0 | 0 | 0 |
| hsa-miR-762 | 0 | 0 | 0 | 0 | 0 | 0 | 0 |
| hsa-miR-764 | 0 | 0 | 0 | 0 | 0 | 0 | 0 |
| hsa-miR-765 | 0 | 3 | 1 | 3 | 3 | 6 | 1 |
| hsa-miR-766 | 229 | 87 | 73 | 93 | 89 | 110 | 29 |
| hsa-miR-767-3p | 0 | 2 | 0 | 0 | 1 | 0 | 0 |
| hsa-miR-767-5p | 0 | 3 | 10 | 7 | 11 | 5 | 0 |
| hsa-miR-769-3p | 91 | 5 | 6 | 10 | 8 | 6 | 3 |
| hsa-miR-769-5p | 4023 | 531 | 514 | 547 | 553 | 547 | 464 |
| hsa-miR-770-5p | 0 | 1 | 4 | 1 | 3 | 7 | 0 |
| hsa-miR-802 | 0 | 46 | 50 | 53 | 51 | 52 | 0 |
| hsa-miR-873 | 0 | 19 | 19 | 17 | 11 | 26 | 2 |
| hsa-miR-874 | 10 | 234 | 230 | 307 | 286 | 254 | 193 |
| hsa-miR-875-3p | 0 | 0 | 0 | 0 | 0 | 0 | 0 |
| hsa-miR-875-5p | 0 | 5 | 1 | 0 | 2 | 0 | 1 |
| hsa-miR-876-3p | 0 | 1 | 0 | 1 | 0 | 4 | 0 |
| hsa-miR-876-5p | 0 | 3 | 1 | 6 | 2 | 1 | 1 |
| hsa-miR-877 | 846 | 133 | 104 | 75 | 55 | 151 | 96 |
| hsa-miR-877* | 2 | 1 | 0 | 0 | 1 | 0 | 0 |
| hsa-miR-885-3p | 0 | 14 | 12 | 8 | 8 | 6 | 1 |
| hsa-miR-885-5p | 0 | 89 | 94 | 66 | 93 | 84 | 2 |
| hsa-miR-886-3p | 69 | 5 | 12 | 12 | 8 | 6 | 8 |
| hsa-miR-886-5p | 15314 | 661 | 618 | 705 | 721 | 710 | 1271 |
| hsa-miR-887 | 0 | 108 | 132 | 128 | 127 | 131 | 116 |
| hsa-miR-888 | 0 | 55 | 49 | 58 | 75 | 84 | 0 |
| hsa-miR-888* | 0 | 0 | 1 | 2 | 0 | 1 | 0 |
| hsa-miR-889 | 0 | 211 | 180 | 273 | 254 | 234 | 57 |
| hsa-miR-890 | 0 | 4 | 1 | 5 | 6 | 11 | 0 |
| hsa-miR-891a | 1 | 358 | 311 | 363 | 390 | 384 | 4 |
| hsa-miR-891b | 0 | 14 | 10 | 11 | 8 | 4 | 0 |
| hsa-miR-892a | 0 | 7 | 4 | 10 | 7 | 6 | 0 |
| hsa-miR-892b | 0 | 5 | 5 | 5 | 2 | 6 | 0 |
| hsa-miR-9 | 13310 | 10506 | 9814 | 11411 | 11015 | 11489 | 233 |
| hsa-miR-9* | 1880 | 2040 | 2327 | 2671 | 2670 | 2212 | 75 |
| hsa-miR-920 | 0 | 0 | 0 | 0 | 0 | 0 | 0 |
| hsa-miR-921 | 0 | 0 | 0 | 0 | 0 | 0 | 0 |
| hsa-miR-922 | 0 | 0 | 0 | 0 | 0 | 0 | 0 |
| hsa-miR-924 | 0 | 0 | 0 | 0 | 0 | 0 | 0 |
| hsa-miR-92a | 27036 | 4490 | 4235 | 4907 | 4803 | 4907 | 3961 |
| hsa-miR-92a-1* | 328 | 61 | 43 | 71 | 61 | 47 | 42 |
| hsa-miR-92a-2* | 0 | 0 | 2 | 1 | 1 | 0 | 0 |
| hsa-miR-92b | 65 | 508 | 522 | 615 | 602 | 591 | 314 |
| hsa-miR-92b* | 4 | 25 | 17 | 15 | 13 | 25 | 9 |
| hsa-miR-93 | 29354 | 5197 | 4866 | 5765 | 5546 | 5717 | 4574 |
| hsa-miR-93* | 25 | 39 | 37 | 39 | 37 | 38 | 71 |
| hsa-miR-933 | 0 | 0 | 0 | 0 | 0 | 1 | 0 |
| hsa-miR-934 | 0 | 101 | 149 | 198 | 206 | 145 | 49 |
| hsa-miR-935 | 1 | 74 | 104 | 125 | 114 | 94 | 9 |
| hsa-miR-936 | 0 | 0 | 0 | 0 | 0 | 0 | 0 |
| hsa-miR-937 | 1 | 0 | 2 | 0 | 0 | 0 | 0 |
| hsa-miR-938 | 0 | 0 | 0 | 0 | 0 | 0 | 0 |
| hsa-miR-939 | 8 | 1 | 0 | 0 | 0 | 0 | 0 |
| hsa-miR-940 | 7 | 4 | 7 | 8 | 5 | 10 | 4 |
| hsa-miR-941 | 244 | 145 | 116 | 136 | 116 | 173 | 43 |
| hsa-miR-942 | 75 | 8 | 12 | 12 | 11 | 8 | 3 |
| hsa-miR-943 | 1 | 0 | 0 | 0 | 0 | 0 | 2 |
| hsa-miR-944 | 1109 | 143 | 143 | 144 | 158 | 164 | 26 |

TABLE 7-continued

| RNA miRNA | Human RNA pool adaptors | | | | | | Breast |
|---|---|---|---|---|---|---|---|
| | Default (lane 1) | 8 × 8 (lane 2) | 16 × 4 (lane 3) | 32 × 2 (lane 4) | 64 × 1 (lane 5) | 8 × 8 (lane 6) | 8 × 8 (lane 7) |
| hsa-miR-95 | 57 | 3409 | 3489 | 3620 | 3782 | 3901 | 720 |
| hsa-miR-96 | 783 | 146 | 122 | 146 | 138 | 173 | 681 |
| hsa-miR-96* | 0 | 0 | 0 | 0 | 0 | 0 | 1 |
| hsa-miR-98 | 1602 | 2924 | 2956 | 3366 | 3559 | 3153 | 2291 |
| hsa-miR-99a | 692 | 23127 | 23513 | 27764 | 27299 | 25367 | 12696 |
| hsa-miR-99a* | 42 | 116 | 97 | 118 | 115 | 112 | 68 |
| hsa-miR-99b | 9 | 16328 | 14746 | 17477 | 16934 | 17389 | 6543 |
| hsa-miR-99b* | 0 | 52 | 58 | 73 | 42 | 55 | 51 |

TABLE 11

| miRNA | Read count-all |
|---|---|
| hsa-let-7a | 3263253 |
| hsa-let-7a* | 2627 |
| hsa-let-7a-2* | 130 |
| hsa-let-7b | 629946 |
| hsa-let-7b* | 2206 |
| hsa-let-7c | 586231 |
| hsa-let-7c* | 41 |
| hsa-let-7d | 80917 |
| hsa-let-7d* | 13259 |
| hsa-let-7e | 115027 |
| hsa-let-7e* | 774 |
| hsa-let-7f | 3480770 |
| hsa-let-7f-1* | 344 |
| hsa-let-7f-2* | 144 |
| hsa-let-7g | 729933 |
| hsa-let-7g* | 2239 |
| hsa-let-7i | 123591 |
| hsa-let-7i* | 3761 |
| hsa-miR-1 | 4827651 |
| hsa-miR-100 | 371538 |
| hsa-miR-100* | 359 |
| hsa-miR-101 | 1018648 |
| hsa-miR-101* | 4418 |
| hsa-miR-103 | 608126 |
| hsa-miR-103-2* | 301 |
| hsa-miR-103-as | 0 |
| hsa-miR-105 | 154 |
| hsa-miR-105* | 6 |
| hsa-miR-106a | 17036 |
| hsa-miR-106a* | 87 |
| hsa-miR-106b | 76043 |
| hsa-miR-106b* | 3665 |
| hsa-miR-107 | 5450 |
| hsa-miR-10a | 411798 |
| hsa-miR-10a* | 1392 |
| hsa-miR-10b | 671361 |
| hsa-miR-10b* | 4311 |
| hsa-miR-1178 | 0 |
| hsa-miR-1179 | 977 |
| hsa-miR-1180 | 351 |
| hsa-miR-1181 | 1 |
| hsa-miR-1182 | 0 |
| hsa-miR-1183 | 0 |
| hsa-miR-1184 | 0 |
| hsa-miR-1185 | 503 |
| hsa-miR-1193 | 3 |
| hsa-miR-1197 | 20 |
| hsa-miR-1200 | 0 |
| hsa-miR-1201 | 1283 |
| hsa-miR-1202 | 0 |
| hsa-miR-1203 | 0 |
| hsa-miR-1204 | 0 |
| hsa-miR-1205 | 0 |
| hsa-miR-1206 | 0 |
| hsa-miR-1207-3p | 0 |
| hsa-miR-1207-5p | 0 |
| hsa-miR-1208 | 0 |
| hsa-miR-122 | 71506 |

TABLE 11-continued

| miRNA | Read count-all |
|---|---|
| hsa-miR-122* | 881 |
| hsa-miR-1224-3p | 8 |
| hsa-miR-1224-5p | 212 |
| hsa-miR-1225-3p | 2 |
| hsa-miR-1225-5p | 12 |
| hsa-miR-1226 | 35 |
| hsa-miR-1226* | 11 |
| hsa-miR-1227 | 0 |
| hsa-miR-1228 | 10 |
| hsa-miR-1228* | 9 |
| hsa-miR-1229 | 15 |
| hsa-miR-1231 | 9 |
| hsa-miR-1233 | 5 |
| hsa-miR-1234 | 7 |
| hsa-miR-1236 | 0 |
| hsa-miR-1237 | 0 |
| hsa-miR-1238 | 1 |
| hsa-miR-124 | 14855 |
| hsa-miR-124* | 55 |
| hsa-miR-1243 | 28 |
| hsa-miR-1244 | 43 |
| hsa-miR-1245 | 23 |
| hsa-miR-1246 | 163980 |
| hsa-miR-1247 | 1190 |
| hsa-miR-1248 | 266 |
| hsa-miR-1249 | 348 |
| hsa-miR-1250 | 22 |
| hsa-miR-1251 | 956 |
| hsa-miR-1252 | 16 |
| hsa-miR-1253 | 0 |
| hsa-miR-1254 | 114 |
| hsa-miR-1255a | 204 |
| hsa-miR-1255b | 59 |
| hsa-miR-1256 | 17 |
| hsa-miR-1257 | 29 |
| hsa-miR-1258 | 38 |
| hsa-miR-1259 | 807 |
| hsa-miR-125a-3p | 820 |
| hsa-miR-125a-5p | 197714 |
| hsa-miR-125b | 407709 |
| hsa-miR-125b-1* | 966 |
| hsa-miR-125b-2* | 18552 |
| hsa-miR-126 | 2107272 |
| hsa-miR-126* | 279706 |
| hsa-miR-1260 | 16 |
| hsa-miR-1260b | 216 |
| hsa-miR-1261 | 0 |
| hsa-miR-1262 | 184 |
| hsa-miR-1263 | 2 |
| hsa-miR-1264 | 13 |
| hsa-miR-1265 | 5 |
| hsa-miR-1266 | 61 |
| hsa-miR-1267 | 2 |
| hsa-miR-1268 | 788 |
| hsa-miR-1269 | 157 |
| hsa-miR-1270 | 1259 |
| hsa-miR-1271 | 576 |
| hsa-miR-1272 | 3 |

TABLE 11-continued

| miRNA | Read count-all |
|---|---|
| hsa-miR-1273 | 0 |
| hsa-miR-1273c | 91 |
| hsa-miR-1273d | 9 |
| hsa-miR-127-3p | 27435 |
| hsa-miR-1274a | 15 |
| hsa-miR-1274b | 617 |
| hsa-miR-1275 | 746 |
| hsa-miR-127-5p | 4243 |
| hsa-miR-1276 | 36 |
| hsa-miR-1277 | 467 |
| hsa-miR-1278 | 34 |
| hsa-miR-1279 | 0 |
| hsa-miR-128 | 28463 |
| hsa-miR-1280 | 75 |
| hsa-miR-1281 | 0 |
| hsa-miR-1282 | 0 |
| hsa-miR-1283 | 3052 |
| hsa-miR-1284 | 12 |
| hsa-miR-1285 | 568 |
| hsa-miR-1286 | 6 |
| hsa-miR-1287 | 415 |
| hsa-miR-1288 | 3 |
| hsa-miR-1289 | 1 |
| hsa-miR-129* | 332 |
| hsa-miR-1290 | 6 |
| hsa-miR-1291 | 364 |
| hsa-miR-1292 | 518 |
| hsa-miR-1293 | 2 |
| hsa-miR-129-3p | 1131 |
| hsa-miR-1294 | 41 |
| hsa-miR-1295 | 27 |
| hsa-miR-129-5p | 4027 |
| hsa-miR-1296 | 785 |
| hsa-miR-1297 | 0 |
| hsa-miR-1298 | 246 |
| hsa-miR-1299 | 935 |
| hsa-miR-1301 | 608 |
| hsa-miR-1302 | 1 |
| hsa-miR-1303 | 133 |
| hsa-miR-1304 | 50 |
| hsa-miR-1305 | 55 |
| hsa-miR-1306 | 33 |
| hsa-miR-1307 | 6293 |
| hsa-miR-1308 | 7471 |
| hsa-miR-130a | 30830 |
| hsa-miR-130a* | 43 |
| hsa-miR-130b | 8344 |
| hsa-miR-130b* | 755 |
| hsa-miR-132 | 10033 |
| hsa-miR-132* | 1469 |
| hsa-miR-1321 | 2 |
| hsa-miR-1322 | 12 |
| hsa-miR-1323 | 40121 |
| hsa-miR-1324 | 0 |
| hsa-miR-133a | 199457 |
| hsa-miR-133b | 6363 |
| hsa-miR-134 | 3019 |
| hsa-miR-135a | 108493 |
| hsa-miR-135a* | 121 |
| hsa-miR-135b | 33044 |
| hsa-miR-135b* | 155 |
| hsa-miR-136 | 21356 |
| hsa-miR-136* | 5945 |
| hsa-miR-137 | 6124 |
| hsa-miR-138 | 16603 |
| hsa-miR-138-1* | 503 |
| hsa-miR-138-2* | 50 |
| hsa-miR-139-3p | 1864 |
| hsa-miR-139-5p | 19160 |
| hsa-miR-140-3p | 632569 |
| hsa-miR-140-5p | 99250 |
| hsa-miR-141 | 87549 |
| hsa-miR-141* | 1759 |
| hsa-miR-142-3p | 863170 |
| hsa-miR-142-5p | 40824 |
| hsa-miR-143 | 27191001 |
| hsa-miR-143* | 131103 |
| hsa-miR-144 | 13924 |

TABLE 11-continued

| miRNA | Read count-all |
|---|---|
| hsa-miR-144* | 141389 |
| hsa-miR-145 | 810044 |
| hsa-miR-145* | 32400 |
| hsa-miR-1468 | 68 |
| hsa-miR-1469 | 0 |
| hsa-miR-146a | 159091 |
| hsa-miR-146a* | 24 |
| hsa-miR-146b-3p | 431 |
| hsa-miR-146b-5p | 945206 |
| hsa-miR-147 | 0 |
| hsa-miR-1470 | 0 |
| hsa-miR-1471 | 0 |
| hsa-miR-147b | 90 |
| hsa-miR-148a | 1306692 |
| hsa-miR-148a* | 6159 |
| hsa-miR-148b | 188242 |
| hsa-miR-148b* | 7002 |
| hsa-miR-149 | 2802 |
| hsa-miR-149* | 49 |
| hsa-miR-150 | 26608 |
| hsa-miR-150* | 259 |
| hsa-miR-151-3p | 142414 |
| hsa-miR-151-5p | 135256 |
| hsa-miR-152 | 179559 |
| hsa-miR-153 | 3912 |
| hsa-miR-1537 | 22 |
| hsa-miR-1538 | 2 |
| hsa-miR-1539 | 0 |
| hsa-miR-154 | 758 |
| hsa-miR-154* | 270 |
| hsa-miR-155 | 162738 |
| hsa-miR-155* | 497 |
| hsa-miR-15a | 45924 |
| hsa-miR-15a* | 47 |
| hsa-miR-15b | 18241 |
| hsa-miR-15b* | 1885 |
| hsa-miR-16 | 434371 |
| hsa-miR-16-1* | 327 |
| hsa-miR-16-2* | 1409 |
| hsa-miR-17 | 176460 |
| hsa-miR-17* | 12954 |
| hsa-miR-181a | 345345 |
| hsa-miR-181a* | 4960 |
| hsa-miR-181a-2* | 4066 |
| hsa-miR-181b | 49597 |
| hsa-miR-181c | 6636 |
| hsa-miR-181c* | 1044 |
| hsa-miR-181d | 4815 |
| hsa-miR-182 | 97847 |
| hsa-miR-182* | 5 |
| hsa-miR-1825 | 0 |
| hsa-miR-1826 | 3477 |
| hsa-miR-1827 | 1 |
| hsa-miR-183 | 22483 |
| hsa-miR-183* | 92 |
| hsa-miR-184 | 4415 |
| hsa-miR-185 | 13309 |
| hsa-miR-185* | 199 |
| hsa-miR-186 | 148992 |
| hsa-miR-186* | 433 |
| hsa-miR-187 | 790 |
| hsa-miR-187* | 57 |
| hsa-miR-188-3p | 43 |
| hsa-miR-188-5p | 633 |
| hsa-miR-18a | 14206 |
| hsa-miR-18a* | 302 |
| hsa-miR-18b | 147 |
| hsa-miR-18b* | 17 |
| hsa-miR-190 | 13151 |
| hsa-miR-1908 | 14 |
| hsa-miR-1909 | 1 |
| hsa-miR-1909* | 0 |
| hsa-miR-190b | 526 |
| hsa-miR-191 | 347191 |
| hsa-miR-191* | 185 |
| hsa-miR-1910 | 2 |
| hsa-miR-1911 | 149 |
| hsa-miR-1911* | 1 |

TABLE 11-continued

| miRNA | Read count-all |
|---|---|
| hsa-miR-1912 | 21 |
| hsa-miR-1913 | 2 |
| hsa-miR-1914 | 1 |
| hsa-miR-1914* | 1 |
| hsa-miR-1915 | 2 |
| hsa-miR-1915* | 0 |
| hsa-miR-192 | 915301 |
| hsa-miR-192* | 1029 |
| hsa-miR-193a-3p | 3073 |
| hsa-miR-193a-5p | 4589 |
| hsa-miR-193b | 29643 |
| hsa-miR-193b* | 1332 |
| hsa-miR-194 | 338472 |
| hsa-miR-194* | 572 |
| hsa-miR-195 | 76407 |
| hsa-miR-195* | 464 |
| hsa-miR-196a | 8449 |
| hsa-miR-196a* | 33 |
| hsa-miR-196b | 20661 |
| hsa-miR-196b* | 27 |
| hsa-miR-197 | 15658 |
| hsa-miR-1972 | 0 |
| hsa-miR-1973 | 128 |
| hsa-miR-1975 | 44554 |
| hsa-miR-1976 | 89 |
| hsa-miR-1979 | 42616 |
| hsa-miR-198 | 2 |
| hsa-miR-199a-3p | 267443 |
| hsa-miR-199a-5p | 58426 |
| hsa-miR-199b-3p | 267443 |
| hsa-miR-199b-5p | 15208 |
| hsa-miR-19a | 28904 |
| hsa-miR-19a* | 27 |
| hsa-miR-19b | 117578 |
| hsa-miR-19b-1* | 545 |
| hsa-miR-19b-2* | 2 |
| hsa-miR-200a | 30201 |
| hsa-miR-200a* | 735 |
| hsa-miR-200b | 52688 |
| hsa-miR-200b* | 4943 |
| hsa-miR-200c | 427036 |
| hsa-miR-200c* | 127 |
| hsa-miR-202 | 6243 |
| hsa-miR-202* | 91648 |
| hsa-miR-203 | 73346 |
| hsa-miR-204 | 8758 |
| hsa-miR-205 | 121249 |
| hsa-miR-205* | 21 |
| hsa-miR-2052 | 0 |
| hsa-miR-2053 | 0 |
| hsa-miR-2054 | 0 |
| hsa-miR-206 | 239800 |
| hsa-miR-208a | 457 |
| hsa-miR-208b | 3831 |
| hsa-miR-20a | 261873 |
| hsa-miR-20a* | 4565 |
| hsa-miR-20b | 14523 |
| hsa-miR-20b* | 181 |
| hsa-miR-21 | 6223972 |
| hsa-miR-21* | 4482 |
| hsa-miR-210 | 14772 |
| hsa-miR-211 | 31 |
| hsa-miR-2110 | 1305 |
| hsa-miR-2113 | 0 |
| hsa-miR-2114 | 93 |
| hsa-miR-2114* | 11 |
| hsa-miR-2115 | 46 |
| hsa-miR-2115* | 85 |
| hsa-miR-2116 | 32 |
| hsa-miR-2116* | 33 |
| hsa-miR-2117 | 0 |
| hsa-miR-212 | 317 |
| hsa-miR-214 | 13273 |
| hsa-miR-214* | 2118 |
| hsa-miR-215 | 848606 |
| hsa-miR-216a | 260 |
| hsa-miR-216b | 705 |
| hsa-miR-217 | 754 |
| hsa-miR-218 | 22992 |
| hsa-miR-218-1* | 624 |
| hsa-miR-218-2* | 26 |
| hsa-miR-219-1-3p | 108 |
| hsa-miR-219-2-3p | 26649 |
| hsa-miR-219-5p | 500 |
| hsa-miR-22 | 159941 |
| hsa-miR-22* | 12506 |
| hsa-miR-220a | 0 |
| hsa-miR-220b | 0 |
| hsa-miR-220c | 0 |
| hsa-miR-221 | 44792 |
| hsa-miR-221* | 17403 |
| hsa-miR-222 | 94321 |
| hsa-miR-222* | 430 |
| hsa-miR-223 | 37671 |
| hsa-miR-223* | 1142 |
| hsa-miR-224 | 8474 |
| hsa-miR-224* | 438 |
| hsa-miR-2276 | 105 |
| hsa-miR-2277 | 30 |
| hsa-miR-2278 | 12 |
| hsa-miR-2355 | 80 |
| hsa-miR-23a | 243206 |
| hsa-miR-23a* | 23 |
| hsa-miR-23b | 210543 |
| hsa-miR-23b* | 231 |
| hsa-miR-24 | 1502194 |
| hsa-miR-24-1* | 3733 |
| hsa-miR-24-2* | 6950 |
| hsa-miR-25 | 33806 |
| hsa-miR-25* | 649 |
| hsa-miR-26a | 1986940 |
| hsa-miR-26a-1* | 62 |
| hsa-miR-26a-2* | 834 |
| hsa-miR-26b | 482254 |
| hsa-miR-26b* | 679 |
| hsa-miR-27a | 267030 |
| hsa-miR-27a* | 745 |
| hsa-miR-27b | 673420 |
| hsa-miR-27b* | 8575 |
| hsa-miR-28-3p | 52126 |
| hsa-miR-28-5p | 60747 |
| hsa-miR-2861 | 0 |
| hsa-miR-2909 | 0 |
| hsa-miR-296-3p | 116 |
| hsa-miR-296-5p | 465 |
| hsa-miR-297 | 0 |
| hsa-miR-298 | 0 |
| hsa-miR-299-3p | 427 |
| hsa-miR-299-5p | 860 |
| hsa-miR-29a | 758430 |
| hsa-miR-29a* | 4199 |
| hsa-miR-29b | 224003 |
| hsa-miR-29b-1* | 332 |
| hsa-miR-29b-2* | 1741 |
| hsa-miR-29c | 50309 |
| hsa-miR-29c* | 5043 |
| hsa-miR-300 | 0 |
| hsa-miR-301a | 1455 |
| hsa-miR-301b | 289 |
| hsa-miR-302a | 34 |
| hsa-miR-302a* | 132 |
| hsa-miR-302b | 81 |
| hsa-miR-302b* | 2 |
| hsa-miR-302c | 11 |
| hsa-miR-302c* | 0 |
| hsa-miR-302d | 23 |
| hsa-miR-302d* | 0 |
| hsa-miR-302e | 0 |
| hsa-miR-302f | 0 |
| hsa-miR-3065-3p | 1456 |
| hsa-miR-3065-5p | 1144 |
| hsa-miR-3074 | 18 |
| hsa-miR-30a | 2082964 |
| hsa-miR-30a* | 90594 |
| hsa-miR-30b | 253420 |
| hsa-miR-30b* | 583 |

TABLE 11-continued

| miRNA | Read count-all |
|---|---|
| hsa-miR-30c | 363593 |
| hsa-miR-30c-1* | 432 |
| hsa-miR-30c-2* | 5633 |
| hsa-miR-30d | 1167397 |
| hsa-miR-30d* | 1597 |
| hsa-miR-30e | 888607 |
| hsa-miR-30e* | 96423 |
| hsa-miR-31 | 11912 |
| hsa-miR-31* | 370 |
| hsa-miR-3115 | 19 |
| hsa-miR-3116 | 5 |
| hsa-miR-3117 | 116 |
| hsa-miR-3118 | 1 |
| hsa-miR-3119 | 0 |
| hsa-miR-3120 | 8 |
| hsa-miR-3121 | 21 |
| hsa-miR-3122 | 4 |
| hsa-miR-3123 | 0 |
| hsa-miR-3124 | 46 |
| hsa-miR-3125 | 32 |
| hsa-miR-3126-3p | 5 |
| hsa-miR-3126-5p | 7 |
| hsa-miR-3127 | 53 |
| hsa-miR-3128 | 30 |
| hsa-miR-3129 | 81 |
| hsa-miR-3130-3p | 1 |
| hsa-miR-3130-5p | 31 |
| hsa-miR-3131 | 9 |
| hsa-miR-3132 | 7 |
| hsa-miR-3133 | 18 |
| hsa-miR-3134 | 12 |
| hsa-miR-3135 | 4 |
| hsa-miR-3136 | 15 |
| hsa-miR-3137 | 0 |
| hsa-miR-3138 | 22 |
| hsa-miR-3139 | 9 |
| hsa-miR-3140 | 19 |
| hsa-miR-3141 | 9 |
| hsa-miR-3142 | 0 |
| hsa-miR-3143 | 9 |
| hsa-miR-3144-3p | 6 |
| hsa-miR-3144-5p | 11 |
| hsa-miR-3145 | 13 |
| hsa-miR-3146 | 34 |
| hsa-miR-3147 | 0 |
| hsa-miR-3148 | 1 |
| hsa-miR-3149 | 27 |
| hsa-miR-3150 | 1 |
| hsa-miR-3151 | 2 |
| hsa-miR-3152 | 1 |
| hsa-miR-3153 | 0 |
| hsa-miR-3154 | 129 |
| hsa-miR-3155 | 2 |
| hsa-miR-3156 | 1 |
| hsa-miR-3157 | 22 |
| hsa-miR-3158 | 221 |
| hsa-miR-3159 | 6 |
| hsa-miR-3160 | 4 |
| hsa-miR-3161 | 11 |
| hsa-miR-3162 | 1 |
| hsa-miR-3163 | 21 |
| hsa-miR-3164 | 60 |
| hsa-miR-3165 | 0 |
| hsa-miR-3166 | 2 |
| hsa-miR-3167 | 6 |
| hsa-miR-3168 | 4 |
| hsa-miR-3169 | 0 |
| hsa-miR-3170 | 5 |
| hsa-miR-3171 | 2 |
| hsa-miR-3172 | 729 |
| hsa-miR-3173 | 9 |
| hsa-miR-3174 | 21 |
| hsa-miR-3175 | 10 |
| hsa-miR-3176 | 59 |
| hsa-miR-3177 | 63 |
| hsa-miR-3178 | 0 |
| hsa-miR-3179 | 23 |
| hsa-miR-3180-3p | 14 |
| hsa-miR-3180-5p | 10 |
| hsa-miR-3181 | 5 |
| hsa-miR-3182 | 11 |
| hsa-miR-3183 | 1 |
| hsa-miR-3184 | 2 |
| hsa-miR-3185 | 0 |
| hsa-miR-3186-3p | 0 |
| hsa-miR-3186-5p | 1 |
| hsa-miR-3187 | 25 |
| hsa-miR-3188 | 118 |
| hsa-miR-3189 | 2 |
| hsa-miR-3190-3p | 22 |
| hsa-miR-3190-5p | 22 |
| hsa-miR-3191 | 5 |
| hsa-miR-3192 | 11 |
| hsa-miR-3193 | 7 |
| hsa-miR-3194 | 52 |
| hsa-miR-3195 | 6 |
| hsa-miR-3196 | 10 |
| hsa-miR-3197 | 0 |
| hsa-miR-3198 | 1 |
| hsa-miR-3199 | 62 |
| hsa-miR-32 | 25140 |
| hsa-miR-32* | 301 |
| hsa-miR-3200 | 515 |
| hsa-miR-3201 | 0 |
| hsa-miR-3202 | 28 |
| hsa-miR-320a | 111802 |
| hsa-miR-320b | 8719 |
| hsa-miR-320c | 5424 |
| hsa-miR-320d | 5980 |
| hsa-miR-320e | 241 |
| hsa-miR-323-3p | 662 |
| hsa-miR-323-5p | 8 |
| hsa-miR-323b-3p | 216 |
| hsa-miR-323b-5p | 2 |
| hsa-miR-324-3p | 1220 |
| hsa-miR-324-5p | 2258 |
| hsa-miR-325 | 0 |
| hsa-miR-326 | 199 |
| hsa-miR-328 | 2414 |
| hsa-miR-329 | 1531 |
| hsa-miR-330-3p | 4705 |
| hsa-miR-330-5p | 751 |
| hsa-miR-331-3p | 1768 |
| hsa-miR-331-5p | 637 |
| hsa-miR-335 | 38506 |
| hsa-miR-335* | 7818 |
| hsa-miR-337-3p | 3906 |
| hsa-miR-337-5p | 4909 |
| hsa-miR-338-3p | 8532 |
| hsa-miR-338-5p | 5359 |
| hsa-miR-339-3p | 10563 |
| hsa-miR-339-5p | 2593 |
| hsa-miR-33a | 13217 |
| hsa-miR-33a* | 371 |
| hsa-miR-33b | 1119 |
| hsa-miR-33b* | 78 |
| hsa-miR-340 | 28380 |
| hsa-miR-340* | 2305 |
| hsa-miR-342-3p | 24621 |
| hsa-miR-342-5p | 2668 |
| hsa-miR-345 | 3394 |
| hsa-miR-346 | 108 |
| hsa-miR-34a | 13143 |
| hsa-miR-34a* | 92 |
| hsa-miR-34b | 1191 |
| hsa-miR-34b* | 1105 |
| hsa-miR-34c-3p | 1826 |
| hsa-miR-34c-5p | 38125 |
| hsa-miR-361-3p | 3940 |
| hsa-miR-361-5p | 21423 |
| hsa-miR-362-3p | 739 |
| hsa-miR-362-5p | 2360 |
| hsa-miR-363 | 16685 |
| hsa-miR-363* | 24 |
| hsa-miR-365 | 20092 |
| hsa-miR-365* | 205 |

TABLE 11-continued

| miRNA | Read count-all |
|---|---|
| hsa-miR-367 | 15 |
| hsa-miR-367* | 0 |
| hsa-miR-369-3p | 6883 |
| hsa-miR-369-5p | 1237 |
| hsa-miR-370 | 726 |
| hsa-miR-371-3p | 22 |
| hsa-miR-371-5p | 132 |
| hsa-miR-372 | 421 |
| hsa-miR-373 | 280 |
| hsa-miR-373* | 16 |
| hsa-miR-374a | 51385 |
| hsa-miR-374a* | 114379 |
| hsa-miR-374b | 39066 |
| hsa-miR-374b* | 1323 |
| hsa-miR-375 | 22890 |
| hsa-miR-376a | 1004 |
| hsa-miR-376a* | 1912 |
| hsa-miR-376b | 1253 |
| hsa-miR-376c | 27443 |
| hsa-miR-377 | 4408 |
| hsa-miR-377* | 75 |
| hsa-miR-378 | 4360229 |
| hsa-miR-378* | 2959 |
| hsa-miR-378b | 33 |
| hsa-miR-378c | 43898 |
| hsa-miR-379 | 46853 |
| hsa-miR-379* | 210 |
| hsa-miR-380 | 122 |
| hsa-miR-380* | 491 |
| hsa-miR-381 | 18003 |
| hsa-miR-382 | 2040 |
| hsa-miR-383 | 829 |
| hsa-miR-384 | 0 |
| hsa-miR-409-3p | 1561 |
| hsa-miR-409-5p | 477 |
| hsa-miR-410 | 1428 |
| hsa-miR-411 | 12443 |
| hsa-miR-411* | 534 |
| hsa-miR-412 | 1 |
| hsa-miR-421 | 2693 |
| hsa-miR-422a | 11 |
| hsa-miR-423-3p | 37223 |
| hsa-miR-423-5p | 83406 |
| hsa-miR-424 | 209609 |
| hsa-miR-424* | 2020 |
| hsa-miR-425 | 77674 |
| hsa-miR-425* | 3099 |
| hsa-miR-4251 | 0 |
| hsa-miR-4252 | 0 |
| hsa-miR-4253 | 0 |
| hsa-miR-4254 | 4 |
| hsa-miR-4255 | 0 |
| hsa-miR-4256 | 0 |
| hsa-miR-4257 | 0 |
| hsa-miR-4258 | 0 |
| hsa-miR-4259 | 0 |
| hsa-miR-4260 | 0 |
| hsa-miR-4261 | 0 |
| hsa-miR-4262 | 0 |
| hsa-miR-4263 | 0 |
| hsa-miR-4264 | 0 |
| hsa-miR-4265 | 0 |
| hsa-miR-4266 | 0 |
| hsa-miR-4267 | 0 |
| hsa-miR-4268 | 0 |
| hsa-miR-4269 | 0 |
| hsa-miR-4270 | 0 |
| hsa-miR-4271 | 0 |
| hsa-miR-4272 | 0 |
| hsa-miR-4273 | 0 |
| hsa-miR-4274 | 0 |
| hsa-miR-4275 | 0 |
| hsa-miR-4276 | 0 |
| hsa-miR-4277 | 0 |
| hsa-miR-4278 | 0 |
| hsa-miR-4279 | 0 |
| hsa-miR-4280 | 0 |
| hsa-miR-4281 | 0 |
| hsa-miR-4282 | 0 |
| hsa-miR-4283 | 0 |
| hsa-miR-4284 | 1392 |
| hsa-miR-4285 | 0 |
| hsa-miR-4286 | 1480 |
| hsa-miR-4287 | 0 |
| hsa-miR-4288 | 0 |
| hsa-miR-4289 | 0 |
| hsa-miR-429 | 21310 |
| hsa-miR-4290 | 0 |
| hsa-miR-4291 | 0 |
| hsa-miR-4292 | 0 |
| hsa-miR-4293 | 0 |
| hsa-miR-4294 | 0 |
| hsa-miR-4295 | 0 |
| hsa-miR-4296 | 1 |
| hsa-miR-4297 | 0 |
| hsa-miR-4298 | 0 |
| hsa-miR-4299 | 0 |
| hsa-miR-4300 | 0 |
| hsa-miR-4301 | 0 |
| hsa-miR-4302 | 0 |
| hsa-miR-4303 | 0 |
| hsa-miR-4304 | 0 |
| hsa-miR-4305 | 0 |
| hsa-miR-4306 | 6 |
| hsa-miR-4307 | 0 |
| hsa-miR-4308 | 0 |
| hsa-miR-4309 | 0 |
| hsa-miR-431 | 128 |
| hsa-miR-431* | 145 |
| hsa-miR-4310 | 0 |
| hsa-miR-4311 | 0 |
| hsa-miR-4312 | 0 |
| hsa-miR-4313 | 0 |
| hsa-miR-4314 | 0 |
| hsa-miR-4315 | 0 |
| hsa-miR-4316 | 0 |
| hsa-miR-4317 | 0 |
| hsa-miR-4318 | 0 |
| hsa-miR-4319 | 0 |
| hsa-miR-432 | 1080 |
| hsa-miR-432* | 10 |
| hsa-miR-4320 | 0 |
| hsa-miR-4321 | 0 |
| hsa-miR-4322 | 0 |
| hsa-miR-4323 | 1 |
| hsa-miR-4324 | 0 |
| hsa-miR-4325 | 0 |
| hsa-miR-4326 | 73 |
| hsa-miR-4327 | 0 |
| hsa-miR-4328 | 27 |
| hsa-miR-4329 | 0 |
| hsa-miR-433 | 529 |
| hsa-miR-4330 | 0 |
| hsa-miR-448 | 8 |
| hsa-miR-449a | 8663 |
| hsa-miR-449b | 1369 |
| hsa-miR-449b* | 29 |
| hsa-miR-449c | 2070 |
| hsa-miR-449c* | 0 |
| hsa-miR-450a | 10118 |
| hsa-miR-450b-3p | 32 |
| hsa-miR-450b-5p | 4838 |
| hsa-miR-451 | 737681 |
| hsa-miR-452 | 104661 |
| hsa-miR-452* | 2187 |
| hsa-miR-454 | 16148 |
| hsa-miR-454* | 111 |
| hsa-miR-455-3p | 14394 |
| hsa-miR-455-5p | 3633 |
| hsa-miR-466 | 3 |
| hsa-miR-483-3p | 395 |
| hsa-miR-483-5p | 3635 |
| hsa-miR-484 | 2717 |
| hsa-miR-485-3p | 545 |
| hsa-miR-485-5p | 1942 |
| hsa-miR-486-3p | 296 |

TABLE 11-continued

| miRNA | Read count-all |
|---|---|
| hsa-miR-486-5p | 12961 |
| hsa-miR-487a | 707 |
| hsa-miR-487b | 3131 |
| hsa-miR-488 | 328 |
| hsa-miR-488* | 26 |
| hsa-miR-489 | 644 |
| hsa-miR-490-3p | 1085 |
| hsa-miR-490-5p | 906 |
| hsa-miR-491-3p | 97 |
| hsa-miR-491-5p | 761 |
| hsa-miR-492 | 6 |
| hsa-miR-493 | 1152 |
| hsa-miR-493* | 2341 |
| hsa-miR-494 | 2613 |
| hsa-miR-495 | 2968 |
| hsa-miR-496 | 93 |
| hsa-miR-497 | 9453 |
| hsa-miR-497* | 249 |
| hsa-miR-498 | 1074 |
| hsa-miR-499-3p | 7353 |
| hsa-miR-499-5p | 16967 |
| hsa-miR-500 | 1116 |
| hsa-miR-500* | 3156 |
| hsa-miR-500b | 907 |
| hsa-miR-501-3p | 736 |
| hsa-miR-501-5p | 546 |
| hsa-miR-502-3p | 1821 |
| hsa-miR-502-5p | 188 |
| hsa-miR-503 | 5056 |
| hsa-miR-504 | 637 |
| hsa-miR-505 | 3599 |
| hsa-miR-505* | 598 |
| hsa-miR-506 | 16376 |
| hsa-miR-507 | 840 |
| hsa-miR-508-3p | 76162 |
| hsa-miR-508-5p | 1212 |
| hsa-miR-509-3-5p | 3903 |
| hsa-miR-509-3p | 7241 |
| hsa-miR-509-5p | 9245 |
| hsa-miR-510 | 1916 |
| hsa-miR-511 | 277 |
| hsa-miR-512-3p | 5968 |
| hsa-miR-512-5p | 1757 |
| hsa-miR-513a-3p | 544 |
| hsa-miR-513a-5p | 2002 |
| hsa-miR-513b | 1058 |
| hsa-miR-513c | 3568 |
| hsa-miR-514 | 156995 |
| hsa-miR-514b-3p | 711 |
| hsa-miR-514b-5p | 2112 |
| hsa-miR-515-3p | 2866 |
| hsa-miR-515-5p | 18861 |
| hsa-miR-516a-3p | 263 |
| hsa-miR-516a-5p | 56271 |
| hsa-miR-516b | 32784 |
| hsa-miR-516b* | 263 |
| hsa-miR-517* | 1742 |
| hsa-miR-517a | 34727 |
| hsa-miR-517b | 34727 |
| hsa-miR-517c | 8109 |
| hsa-miR-518a-3p | 8007 |
| hsa-miR-518a-5p | 1202 |
| hsa-miR-518b | 16097 |
| hsa-miR-518c | 33419 |
| hsa-miR-518c* | 610 |
| hsa-miR-518d-3p | 262 |
| hsa-miR-518d-5p | 1426 |
| hsa-miR-518e | 5542 |
| hsa-miR-518e* | 17339 |
| hsa-miR-518f | 10142 |
| hsa-miR-518f* | 1041 |
| hsa-miR-519a | 16658 |
| hsa-miR-519a* | 17339 |
| hsa-miR-519b-3p | 2282 |
| hsa-miR-519b-5p | 17339 |
| hsa-miR-519c-3p | 5238 |
| hsa-miR-519c-5p | 17339 |
| hsa-miR-519d | 9568 |
| hsa-miR-519e | 190 |
| hsa-miR-519e* | 494 |
| hsa-miR-520a-3p | 2395 |
| hsa-miR-520a-5p | 2644 |
| hsa-miR-520b | 1691 |
| hsa-miR-520c-3p | 1691 |
| hsa-miR-520c-5p | 1426 |
| hsa-miR-520d-3p | 1408 |
| hsa-miR-520d-5p | 841 |
| hsa-miR-520e | 205 |
| hsa-miR-520f | 3634 |
| hsa-miR-520g | 7961 |
| hsa-miR-520h | 10836 |
| hsa-miR-521 | 2359 |
| hsa-miR-522 | 4224 |
| hsa-miR-522* | 17339 |
| hsa-miR-523 | 16402 |
| hsa-miR-523* | 17339 |
| hsa-miR-524-3p | 1566 |
| hsa-miR-524-5p | 1943 |
| hsa-miR-525-3p | 7310 |
| hsa-miR-525-5p | 4442 |
| hsa-miR-526a | 1426 |
| hsa-miR-526b | 6191 |
| hsa-miR-526b* | 1651 |
| hsa-miR-527 | 1202 |
| hsa-miR-532-3p | 3688 |
| hsa-miR-532-5p | 14360 |
| hsa-miR-539 | 1024 |
| hsa-miR-541 | 13 |
| hsa-miR-541* | 9 |
| hsa-miR-542-3p | 30135 |
| hsa-miR-542-5p | 2681 |
| hsa-miR-543 | 511 |
| hsa-miR-544 | 30 |
| hsa-miR-544b | 2 |
| hsa-miR-545 | 84 |
| hsa-miR-545* | 146 |
| hsa-miR-548a-3p | 133 |
| hsa-miR-548a-5p | 15 |
| hsa-miR-548b-3p | 102 |
| hsa-miR-548b-5p | 40 |
| hsa-miR-548c-3p | 18 |
| hsa-miR-548c-5p | 290 |
| hsa-miR-548d-3p | 46 |
| hsa-miR-548d-5p | 467 |
| hsa-miR-548e | 754 |
| hsa-miR-548f | 220 |
| hsa-miR-548g | 1 |
| hsa-miR-548h | 18 |
| hsa-miR-548i | 106 |
| hsa-miR-548j | 242 |
| hsa-miR-548k | 210 |
| hsa-miR-548l | 56 |
| hsa-miR-548m | 0 |
| hsa-miR-548n | 55 |
| hsa-miR-548o | 231 |
| hsa-miR-548p | 5 |
| hsa-miR-548q | 79 |
| hsa-miR-548s | 11 |
| hsa-miR-548t | 19 |
| hsa-miR-548u | 4 |
| hsa-miR-548v | 46 |
| hsa-miR-548w | 3 |
| hsa-miR-548x | 0 |
| hsa-miR-549 | 26 |
| hsa-miR-550 | 183 |
| hsa-miR-550* | 125 |
| hsa-miR-551a | 28 |
| hsa-miR-551b | 129 |
| hsa-miR-551b* | 31 |
| hsa-miR-552 | 61 |
| hsa-miR-553 | 0 |
| hsa-miR-554 | 0 |
| hsa-miR-555 | 0 |
| hsa-miR-556-3p | 24 |
| hsa-miR-556-5p | 141 |
| hsa-miR-557 | 0 |

TABLE 11-continued

| miRNA | Read count-all |
|---|---|
| hsa-miR-558 | 0 |
| hsa-miR-559 | 6 |
| hsa-miR-561 | 24 |
| hsa-miR-562 | 0 |
| hsa-miR-563 | 0 |
| hsa-miR-564 | 1 |
| hsa-miR-566 | 0 |
| hsa-miR-567 | 0 |
| hsa-miR-568 | 0 |
| hsa-miR-569 | 0 |
| hsa-miR-570 | 146 |
| hsa-miR-571 | 0 |
| hsa-miR-572 | 1 |
| hsa-miR-573 | 199 |
| hsa-miR-574-3p | 10204 |
| hsa-miR-574-5p | 1628 |
| hsa-miR-575 | 0 |
| hsa-miR-576-3p | 683 |
| hsa-miR-576-5p | 1574 |
| hsa-miR-577 | 3344 |
| hsa-miR-578 | 0 |
| hsa-miR-579 | 63 |
| hsa-miR-580 | 150 |
| hsa-miR-581 | 17 |
| hsa-miR-582-3p | 3511 |
| hsa-miR-582-5p | 2439 |
| hsa-miR-583 | 0 |
| hsa-miR-584 | 1494 |
| hsa-miR-585 | 436 |
| hsa-miR-586 | 0 |
| hsa-miR-587 | 0 |
| hsa-miR-588 | 0 |
| hsa-miR-589 | 1443 |
| hsa-miR-589* | 155 |
| hsa-miR-590-3p | 5086 |
| hsa-miR-590-5p | 11304 |
| hsa-miR-591 | 0 |
| hsa-miR-592 | 269 |
| hsa-miR-593 | 0 |
| hsa-miR-593* | 0 |
| hsa-miR-595 | 0 |
| hsa-miR-596 | 0 |
| hsa-miR-597 | 33 |
| hsa-miR-598 | 10797 |
| hsa-miR-599 | 2 |
| hsa-miR-600 | 9 |
| hsa-miR-601 | 0 |
| hsa-miR-602 | 3 |
| hsa-miR-603 | 5 |
| hsa-miR-604 | 0 |
| hsa-miR-605 | 28 |
| hsa-miR-606 | 0 |
| hsa-miR-607 | 1 |
| hsa-miR-608 | 0 |
| hsa-miR-609 | 2 |
| hsa-miR-610 | 4 |
| hsa-miR-611 | 0 |
| hsa-miR-612 | 0 |
| hsa-miR-613 | 0 |
| hsa-miR-614 | 2 |
| hsa-miR-615-3p | 341 |
| hsa-miR-615-5p | 4 |
| hsa-miR-616 | 57 |
| hsa-miR-616* | 196 |
| hsa-miR-617 | 0 |
| hsa-miR-618 | 356 |
| hsa-miR-619 | 0 |
| hsa-miR-620 | 0 |
| hsa-miR-621 | 0 |
| hsa-miR-622 | 10 |
| hsa-miR-623 | 0 |
| hsa-miR-624 | 47 |
| hsa-miR-624* | 142 |
| hsa-miR-625 | 791 |
| hsa-miR-625* | 1449 |
| hsa-miR-626 | 0 |
| hsa-miR-627 | 1704 |
| hsa-miR-628-3p | 1869 |
| hsa-miR-628-5p | 6569 |
| hsa-miR-629 | 1282 |
| hsa-miR-629* | 187 |
| hsa-miR-630 | 0 |
| hsa-miR-631 | 0 |
| hsa-miR-632 | 2 |
| hsa-miR-633 | 0 |
| hsa-miR-634 | 0 |
| hsa-miR-635 | 0 |
| hsa-miR-636 | 6 |
| hsa-miR-637 | 0 |
| hsa-miR-638 | 0 |
| hsa-miR-639 | 3 |
| hsa-miR-640 | 0 |
| hsa-miR-641 | 122 |
| hsa-miR-642 | 81 |
| hsa-miR-643 | 69 |
| hsa-miR-644 | 0 |
| hsa-miR-645 | 0 |
| hsa-miR-646 | 0 |
| hsa-miR-647 | 0 |
| hsa-miR-648 | 0 |
| hsa-miR-649 | 0 |
| hsa-miR-650 | 3 |
| hsa-miR-651 | 1075 |
| hsa-miR-652 | 4967 |
| hsa-miR-653 | 479 |
| hsa-miR-654-3p | 2161 |
| hsa-miR-654-5p | 151 |
| hsa-miR-655 | 1774 |
| hsa-miR-656 | 274 |
| hsa-miR-657 | 0 |
| hsa-miR-658 | 1 |
| hsa-miR-659 | 2 |
| hsa-miR-660 | 3414 |
| hsa-miR-661 | 0 |
| hsa-miR-662 | 0 |
| hsa-miR-663 | 60 |
| hsa-miR-663b | 44 |
| hsa-miR-664 | 3101 |
| hsa-miR-664* | 2320 |
| hsa-miR-665 | 65 |
| hsa-miR-668 | 53 |
| hsa-miR-670 | 5 |
| hsa-miR-671-3p | 92 |
| hsa-miR-671-5p | 2990 |
| hsa-miR-675 | 71 |
| hsa-miR-675* | 2472 |
| hsa-miR-7 | 66615 |
| hsa-miR-708 | 16305 |
| hsa-miR-708* | 1017 |
| hsa-miR-7-1* | 976 |
| hsa-miR-711 | 0 |
| hsa-miR-718 | 0 |
| hsa-miR-7-2* | 86 |
| hsa-miR-720 | 2724 |
| hsa-miR-744 | 10452 |
| hsa-miR-744* | 248 |
| hsa-miR-758 | 89 |
| hsa-miR-759 | 0 |
| hsa-miR-760 | 95 |
| hsa-miR-761 | 0 |
| hsa-miR-762 | 0 |
| hsa-miR-764 | 0 |
| hsa-miR-765 | 46 |
| hsa-miR-766 | 1204 |
| hsa-miR-767-3p | 5 |
| hsa-miR-767-5p | 72 |
| hsa-miR-769-3p | 163 |
| hsa-miR-769-5p | 11515 |
| hsa-miR-770-5p | 26 |
| hsa-miR-802 | 486 |
| hsa-miR-873 | 305 |
| hsa-miR-874 | 2982 |
| hsa-miR-875-3p | 0 |
| hsa-miR-875-5p | 15 |
| hsa-miR-876-3p | 25 |
| hsa-miR-876-5p | 19 |

TABLE 11-continued

| miRNA | Read count-all |
|---|---|
| hsa-miR-877 | 2724 |
| hsa-miR-877* | 9 |
| hsa-miR-885-3p | 173 |
| hsa-miR-885-5p | 906 |
| hsa-miR-886-3p | 168 |
| hsa-miR-886-5p | 27435 |
| hsa-miR-887 | 1793 |
| hsa-miR-888 | 666 |
| hsa-miR-888* | 7 |
| hsa-miR-889 | 3236 |
| hsa-miR-890 | 111 |
| hsa-miR-891a | 4506 |
| hsa-miR-891b | 94 |
| hsa-miR-892a | 87 |
| hsa-miR-892b | 49 |
| hsa-miR-9 | 165442 |
| hsa-miR-9* | 29721 |
| hsa-miR-920 | 0 |
| hsa-miR-921 | 1 |
| hsa-miR-922 | 0 |
| hsa-miR-924 | 0 |
| hsa-miR-92a | 85398 |
| hsa-miR-92a-1* | 1103 |
| hsa-miR-92a-2* | 6 |
| hsa-miR-92b | 6766 |
| hsa-miR-92b* | 391 |
| hsa-miR-93 | 95298 |
| hsa-miR-93* | 475 |
| hsa-miR-933 | 2 |
| hsa-miR-934 | 1197 |
| hsa-miR-935 | 926 |
| hsa-miR-936 | 0 |
| hsa-miR-937 | 6 |
| hsa-miR-938 | 0 |
| hsa-miR-939 | 13 |
| hsa-miR-940 | 71 |
| hsa-miR-941 | 2312 |
| hsa-miR-942 | 172 |
| hsa-miR-943 | 3 |
| hsa-miR-944 | 3294 |
| hsa-miR-95 | 47301 |
| hsa-miR-96 | 3084 |
| hsa-miR-96* | 2 |
| hsa-miR-98 | 43595 |
| hsa-miR-99a | 314406 |
| hsa-miR-99a* | 1328 |
| hsa-miR-99b | 212576 |
| hsa-miR-99b* | 900 |

What is claimed is:

1. A method of preparing a target nucleic acid for sequencing comprising the steps of:
   a) ligating a 3' adaptor to the target nucleic acid, wherein the 3' adaptor consists of the nucleotide sequence of SEQ ID NO:66 or is an extended 3' adaptor comprising the nucleotide sequence of SEQ ID NO:66 with one or more nucleotides added to the 5' end;
   b) ligating a 5' adaptor to the 3' adaptor-target nucleic acid complex of step (a), wherein the 5' adaptor consists of the nucleotide sequence of SEQ ID NO:1 or is an extended 5' adaptor comprising the nucleotide sequence of SEQ ID NO:1 with one or more nucleotides added to the 3' end;
   c) reverse transcribing the 3' adaptor-target nucleic acid-5' adaptor ligation product of step (b);
   d) PCR amplifying the reverse transcribed ligation product of step (c); and
   e) gel purifying the amplified target nucleic acid;
   provided that at least one of steps (a) and (b) must utilize an extended 3' or 5' adaptor, respectively.

2. The method of claim 1, further comprising:
   f) sequencing the gel purified target nucleic acid of step (e).

3. The method of claim 2, wherein more than one 5' adaptor is utilized for step (b).

4. The method of claim 3, wherein step (b) utilizes a pool of 5' adaptors, said pool comprising 16 or more different nucleotide sequences each selected from the group consisting of SEQ ID NOs:2 to 65.

5. The method of claim 1, wherein more than one 3' adaptor is utilized for step (a).

6. The method of claim 1, wherein the target nucleic acid is a DNA or RNA molecule.

7. The method of claim 6, wherein the target nucleic acid is a smRNA.

* * * * *